United States Patent
Chou

(10) Patent No.: US 10,113,183 B2
(45) Date of Patent: *Oct. 30, 2018

(54) ADENO-ASSOCIATED VIRUS VECTORS FOR TREATMENT OF GLYCOGEN STORAGE DISEASE

(71) Applicant: The United States of America, as represented by the Secretary, Department of Health and Human Services, Washington, DC (US)

(72) Inventor: Janice J. Chou, North Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/493,622

(22) Filed: Apr. 21, 2017

(65) Prior Publication Data

US 2017/0233763 A1    Aug. 17, 2017

Related U.S. Application Data

(63) Continuation of application No. 15/038,979, filed as application No. PCT/US2014/067415 on Nov. 25, 2014, now Pat. No. 9,644,216.

(60) Provisional application No. 61/908,861, filed on Nov. 26, 2013.

(51) Int. Cl.
   C12N 15/86    (2006.01)
   A61K 48/00    (2006.01)
   C12N 9/16     (2006.01)
   C12N 7/00     (2006.01)

(52) U.S. Cl.
   CPC ............ *C12N 15/86* (2013.01); *A61K 48/005* (2013.01); *A61K 48/0008* (2013.01); *A61K 48/0066* (2013.01); *A61K 48/0075* (2013.01); *C12N 7/00* (2013.01); *C12N 9/16* (2013.01); *C12Y 301/03009* (2013.01); *C12N 2750/14143* (2013.01); *C12N 2830/008* (2013.01); *C12N 2830/42* (2013.01)

(58) Field of Classification Search
   None
   See application file for complete search history.

(56) References Cited

FOREIGN PATENT DOCUMENTS

EP    2 412 387    2/2012

OTHER PUBLICATIONS

Chou et al., "Glycogen storage disease type I and G6Pase-β deficiency: etiology and therapy," *Nat. Rev. Endocrinol.* vol. 6(12):676-688, 2010.
Chou and Mansfield, "Recombinant AAV-Directed Gene Therapy for Type I Glycogen Storage Diseases," *Expert Opin. Biol. Ther.*, vol. 11:1011-1024, 2011.
Daya and Berns, "Gene Therapy Using Adeno-Associated Virus Vectors," *Clin. Microbiol. Rev.*, vol. 21:583-593, 2008.
GenBank Accession No. NG_011808.1, deposited Apr. 10, 2009 (8 pages).
Ghosh et al., "Long-Term Correction of Murine Glycogen Storage Disease Type Ia by Recombinant Adeno-Associated Virus-1-Mediated Gene Transfer," *Gene Ther.*, vol. 13:321-329, 2006.
Grieger et al., "Packaging Capacity of Adeno-Associated Virus Serotypes: Impact of Larger Genomes on Infectivity and Postentry Steps," *J. Virol.*, vol. 79:9933-9944, 2005.
Koeberl et al., "AAV Vector-Mediated Reversal of Hypoglycemia in Canine and Murine Glycogen Storage Disease Type Ia," *Mol. Ther.*, vol. 16:665-672, 2008.
Lee et al., "Prevention of Hepatocellular Adenoma and Correction of Metabolic Abnormalities in Murine Glycogen Storage Disease Type Ia by Gene Therapy," *Hepatology*, vol. 56:1719-1729, 2012.
Lee et al., "The Upstream Enhancer Elements of the G6PC Promoter are Critical for Optimal G6PC Expression in Murine Glycogen Storage Disease Type Ia," *Mol. Genet. Metab.*, vol. 110:275-280, 2013.
Wu et al., "Optimization of Self-Complementary AAV Vectors for Liver-Directed Expression Results in Sustained Correction of Hemophilia B at Low Vector Dose," *Mol. Ther.*, vol. 16:280-289, 2008.
Yiu et al., "Complete Normalization of Hepatic G6PC Deficiency in Murine Glycogen Storage Disease Type Ia Using Gene Therapy," *Mol. Ther.*, vol. 18:1076-1084, 2010.

*Primary Examiner* — Catherine S Hibbert
(74) *Attorney, Agent, or Firm* — Klarquist Sparkman, LLP

(57) ABSTRACT

The present disclosure describes improved adeno-associated virus (AAV) vectors for gene therapy applications in the treatment of glycogen storage disease, particularly glycogen storage disease type Ia (GSD-Ia). Described are recombinant nucleic acid molecules, vectors and recombinant AAV that include a G6PC promoter/enhancer, a synthetic intron, a G6PC coding sequence (such as a wild-type or codon-optimized G6PC coding sequence), and stuffer nucleic acid sequence situated between the G6PC promoter/enhancer and the intron, as well as between the intron and the G6PC coding sequence. The recombinant AAVs disclosed herein exhibit highly efficient liver transduction and are capable of correcting metabolic abnormalities in an animal model of GSD-Ia.

20 Claims, 15 Drawing Sheets

Specification includes a Sequence Listing.

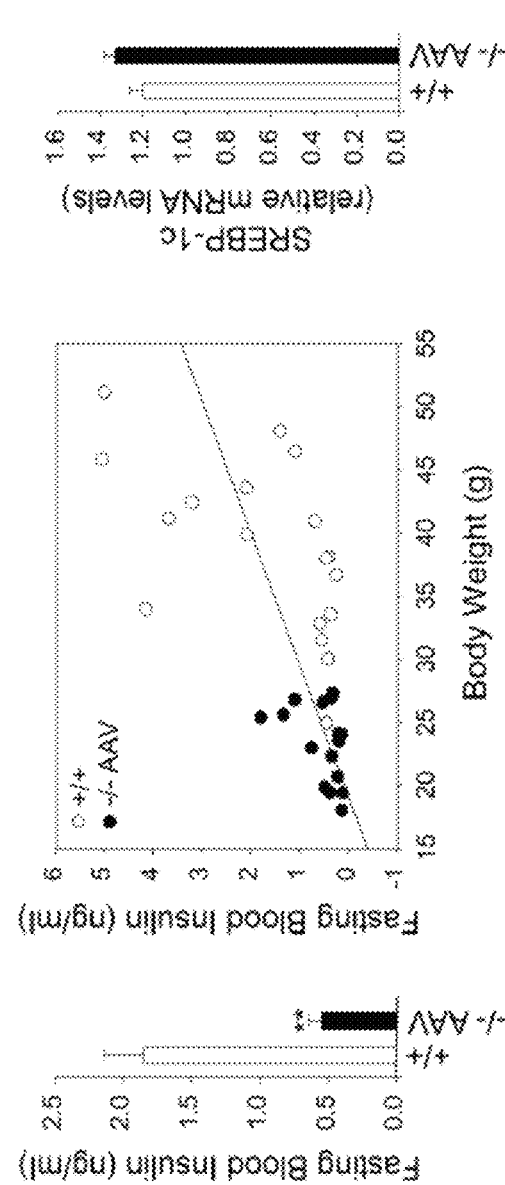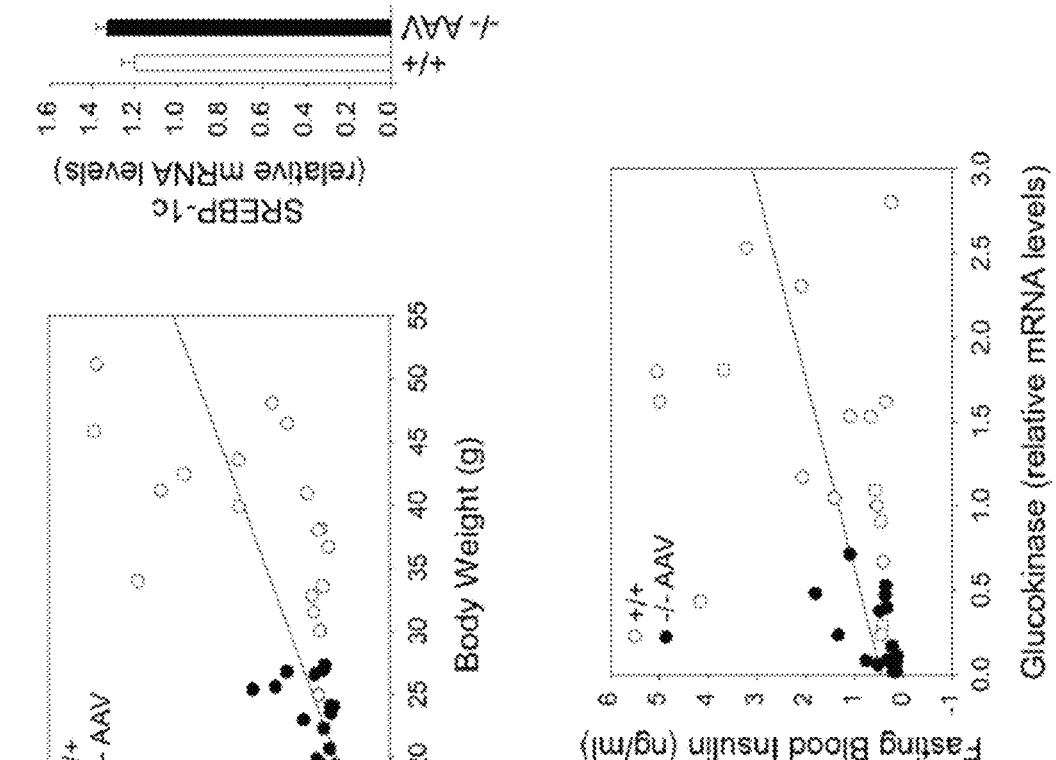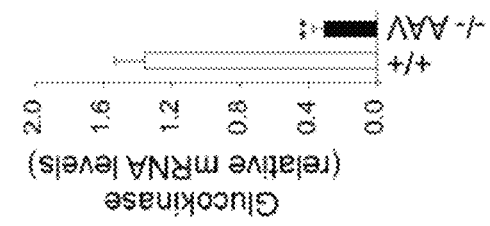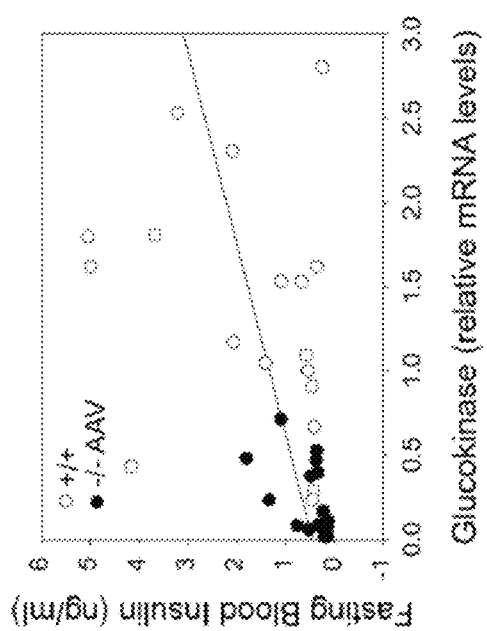
FIG. 5A
FIG. 5B
FIG. 5C

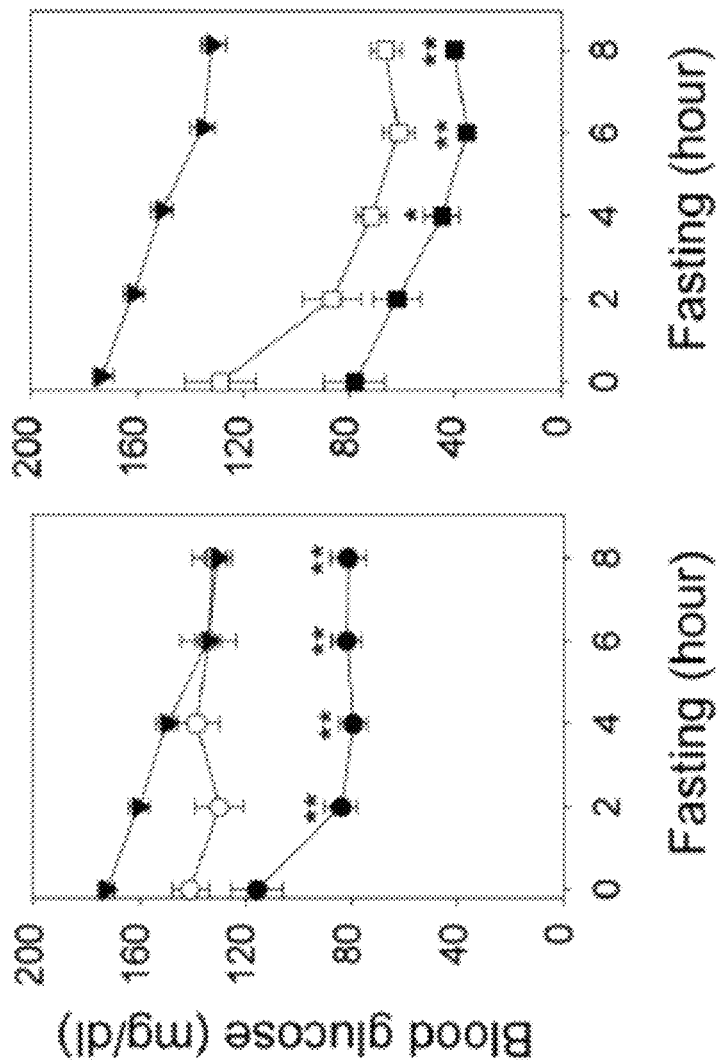
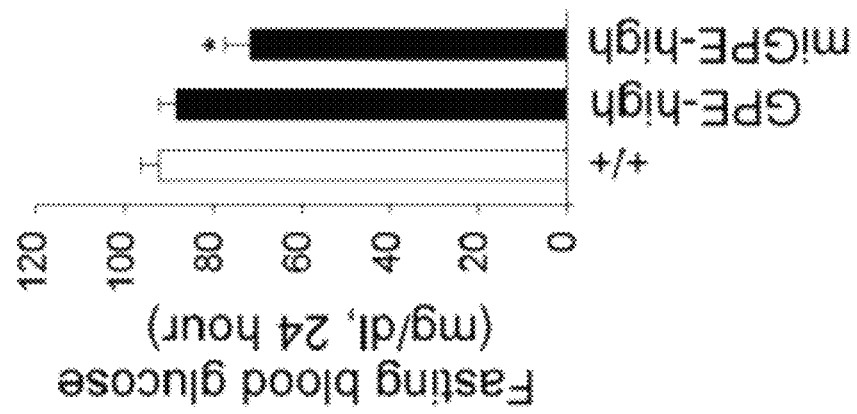
FIG. 8A
FIG. 8B

First line: canine G6Pase-α
Second line: human G6Pase-α

FIG. 10

Amino acid difference between human, mouse, rat and canine G6Pase-α:

| | Amino acid | Amino acid | Amino acid | Amino acid | Amino acid | Amino acid | Amino acid | Amino acid |
|---|---|---|---|---|---|---|---|---|
| Human | E3 (N) | Q54 (C1) | Q139 (C2) | S196 (H5) | H199 (C3) | Q242 (L3) | Q247 (L3) | L292 (H8) |
| mouse | E3 | K54 | R139 | S196 | H199 | K242 | R247 | F292 |
| Rat | E3 | Q54 | R139 | S196 | H199 | K242 | R247 | L292 |
| Dog | K3 | R54 | R139 | R196 | Q199 | R242 | R247 | F292 |

| | Amino acid | Amino acid | Amino acid | Amino acid | Amino acid | Amino acid | Amino acid | Amino acid |
|---|---|---|---|---|---|---|---|---|
| Human | S298 (H8) | A301 (H8) | V318 (L4) | V324 (H9) | V332 (H9) | Q347 (C) | L349 (C) | G350 (C) |
| mouse | C298 | A301 | V318 | I324 | T332 | R347 | L349 | G350 |
| Rat | C298 | A301 | I318 | I324 | T332 | R347 | L349 | G350 |
| Dog | C298 | V301 | T318 | T324 | A332 | R347 | F349 | D350 |

| | Amino acid | Amino acid |
|---|---|---|
| Human | H353 (C) | |
| mouse | H353 | |
| Rat | H353 | |
| Dog | D353 | |

H: helical domain (H1 to H9)
N- N-terminal domain
C: carboxyl terminal domain
L-loop: luminal loop (L1 to L4)
C-loop: cytoplasmic loop (C1 to C4)

ADENO-ASSOCIATED VIRUS VECTORS FOR TREATMENT OF GLYCOGEN STORAGE DISEASE

CROSS REFERENCE TO RELATED APPLICATIONS

This is a continuation of U.S. application Ser. No. 15/038,979, filed May 24, 2016, which is the U.S. National Stage of International Application No. PCT/US2014/067415, filed Nov. 25, 2014, published in English under PCT Article 21(2), which claims the benefit of U.S. Provisional Application No. 61/908,861, filed Nov. 26, 2013. The above-listed applications are herein incorporated by reference in their entirety.

FIELD

This disclosure concerns gene therapy vectors for the treatment of glycogen storage disease, particularly glycogen storage disease type Ia.

BACKGROUND

Glycogen storage disease type Ia (GSD-Ia or von Gierke disease, MIM232200) is caused by a deficiency in glucose-6-phosphatase-α (G6Pase-α), an enzyme that is expressed primarily in the liver, kidney, and intestine (Chou et al., *Nat Rev Endocrinol* 6:676-688, 2010). G6Pase-α, encoded by the G6PC gene, is a hydrophobic protein anchored in the endoplasmic reticulum (ER) by nine transmembrane helices (Chou et al., *Nat Rev Endocrinol* 6:676-688, 2010). This enzyme catalyzes the hydrolysis of glucose-6-phosphate (G6P) to glucose and phosphate in the terminal step of glycogenolysis and gluconeogenesis. Patients affected by GSD-Ia are unable to maintain glucose homeostasis and present with fasting hypoglycemia, growth retardation, hepatomegaly, nephromegaly, hyperlipidemia, hyperuricemia, and lactic academia (Chou et al., *Nat Rev Endocrinol* 6:676-688, 2010).

There is currently no cure for GSD-Ia. Hypoglycemia can be managed using dietary therapies (Greene et al., *N Engl J Med* 294:423-425, 1976; Chen et al., *N Engl J Med* 310:171-175, 1984) that enable patients to attain near normal growth and pubertal development. However, the longer term clinical complications, and their underlying pathological processes, remain uncorrected. One of the most significant chronic risks is hepatocellular adenoma (HCA), that develops in 70-80% of GSD-I patients over 25 years old (Chou et al., *Nat Rev Endocrinol* 6:676-688, 2010; Labrune et al., *J Pediatr Gastroenterol Nutr* 24:276-279, 1997; Rake et al., *Eur J Pediatr* 161(Suppl 1):S20-S34, 2002). HCAs in GSD-Ia patients are small, multiple, and nonencapsulated, with complications including local compression and intratumoral hemorrhage. In 10% of GSD-Ia patients, HCAs undergo malignant transformation to hepatocellular carcinoma (HCC) (Chou et al., *Nat Rev Endocrinol* 6:676-688, 2010; Rake et al., *Eur J Pediatr* 161(Suppl 1):S20-S34, 2002; Franco et al., *J Inherit Metab Dis* 28:153-162, 2005).

Gene therapy studies using recombinant adeno-associated virus (AAV) carrying G6Pase-α have been performed in animal models of GSD-Ia; these studies have demonstrated efficacy in the absence of toxicity (reviewed in Chou and Mansfield, *Expert Opin Biol Ther* 11:1011-1024, 2011). Previous studies using the mouse model of GSD-Ia have shown that recombinant AAV expressing G6Pase-α directed by the CBA promoter/CMV enhancer (Ghosh et al., *Gene Ther* 13:321-329, 2006), the canine G6PC promoter (Koeberl et al., *Gene Ther* 13:1281-1289, 2006), or the human G6PC promoter at nucleotides −298 to +128 of the G6PC 5' flanking region (Koeberl et al., *Mol Ther* 16:665-672, 2008) deliver the G6Pase-α transgene to the liver and achieve extended correction of this disorder. However, while these studies have shown promise, none have been capable of completely correcting hepatic G6Pase-α deficiency.

SUMMARY

Provided herein are recombinant nucleic acid molecules, adeno-associated virus (AAV) vectors and recombinant AAV that can be used in gene therapy applications for the treatment of glycogen storage disease, specifically GSD-Ia.

In some embodiments, the recombinant nucleic acid molecules include a G6PC promoter/enhancer, a synthetic intron, and the G6PC coding region, the latter optionally being codon-optimized for expression in human cells. The recombinant nucleic acid molecules further include stuffer nucleic acid sequence situated between the G6PC promoter/enhancer and the intron, as well as between the intron and the G6PC coding sequence. In particular non-limiting examples, the recombinant nucleic acid molecules comprise nucleotides 182-4441 of SEQ ID NO: 1 or nucleotides 182-4441 of SEQ ID NO: 3.

In some embodiments, the recombinant nucleic acid molecules further include 5' and 3' inverted terminal repeat (ITR) sequences. In some examples, the recombine ant nucleic acid molecules comprise nucleotides 17-4819 of SEQ ID NO: 1 or nucleotides 17-4819 of SEQ ID NO: 3. In other embodiments, the recombinant nucleic acid molecules comprise the complete vector nucleic acid sequences of SEQ ID NO: 1 or SEQ ID NO: 3.

Also provided are vectors comprising the recombinant nucleic acid molecules disclosed herein. In some embodiments, the vectors are AAV vectors, such as AAV8 vectors. Further provided are isolated host cells comprising the recombinant nucleic acid molecules or vectors disclosed herein. For example, the isolated host cells can be cells suitable for propagation of AAV.

Also provided herein are recombinant AAV (rAAV) comprising the recombinant nucleic acid molecules disclosed herein. Compositions comprising the rAAV are also provided by the present disclosure.

Further provided is a method of treating a subject diagnosed with a glycogen storage disease, comprising selecting a subject with glycogen storage disease type Ia (GSD-Ia) and administering to the subject a therapeutically effective amount of the rAAV, or compositions comprising the rAAV, disclosed herein.

The foregoing and other objects, features, and advantages of the invention will become more apparent from the following detailed description, which proceeds with reference to the accompanying figures.

BRIEF DESCRIPTION OF THE DRAWINGS

(FIG. 1A) Body weights of female G6pc$^{-/-}$ mice infused with $1.2 \times 10^{11}$ vg/mouse of AAV-GPE and their female G6pc$^{+/+}$/G6pc$^{+/-}$ littermates are shown. The age at infusion (2 days, 2 weeks or 4 weeks) is shown above the graph. (○), G6pc$^{+/+}$/G6pc$^{+/-}$ mice; (●), AAV-GPE-infused G6pc$^{-/-}$ mice. (FIG. 1B) Blood glucose, cholesterol, triglyceride, uric acid, and lactic acid levels of mice infused with AAV-GPE are shown.

Because of the similarities of the respective metabolites in each group, data shown are pooled data of age 6-24 weeks. (+/+& +/−), G6pc$^{+/+}$/G6pc$^{+/-}$, (−/−), G6pc$^{-/-}$, or (−/− GPE), G6pc$^{-/-}$ mice infused with AAV-GPE at age 2 days (n=36), 2 weeks (n=24), or 4 weeks (n=9). Data are presented as mean±SEM. *p<0.05, **p<0.005.

Figure 2A:
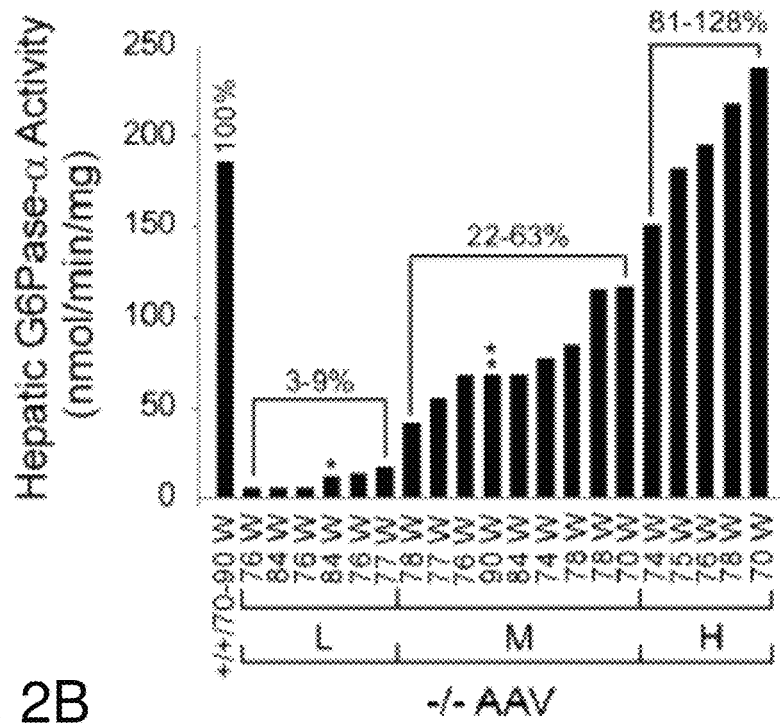
Figure 2B:
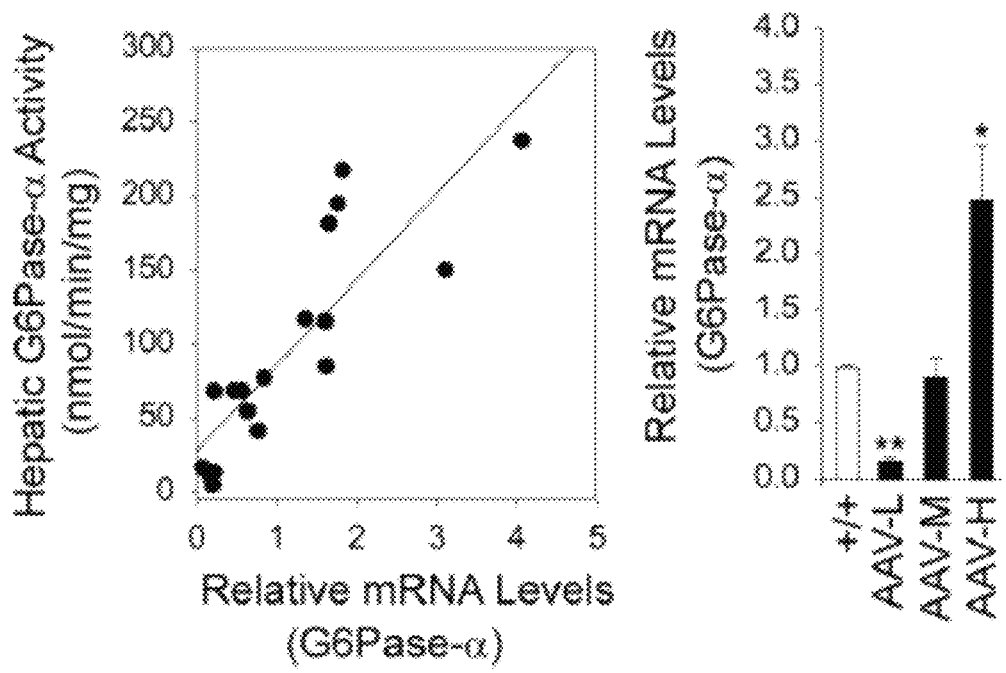

FIGS. 2A-2B are graphs showing hepatic G6Pase-α activity and mRNA expression in wild type and AAV-GPE-treated G6pc$^{-/-}$ mice following a 24-hour fast. Seven 2-week, 11 four-week, one 15-week (*) and one 30-week (**) old G6pc$^{-/-}$ mice were infused with varying doses of AAV-GPE; G6Pase-α activity and mRNA expression were evaluated when mice were 70-90 weeks of age. (FIG. 2A) Hepatic G6Pase-α activity is shown at the indicated ages in weeks (W). The mice are grouped based on their G6Pase-α activity relative to wild type activity as low (AAV-L), medium (AAV-M) and high (AAV-H). (FIG. 2B) Hepatic G6Pase-α mRNA expression and its relationship to G6Pase-α activity in AAV-GPE-treated G6pc$^{-/-}$ mice. Data are presented as mean±SEM. In FIG. 2B, *P<0.05, **P<0.005.

Figure 3A:
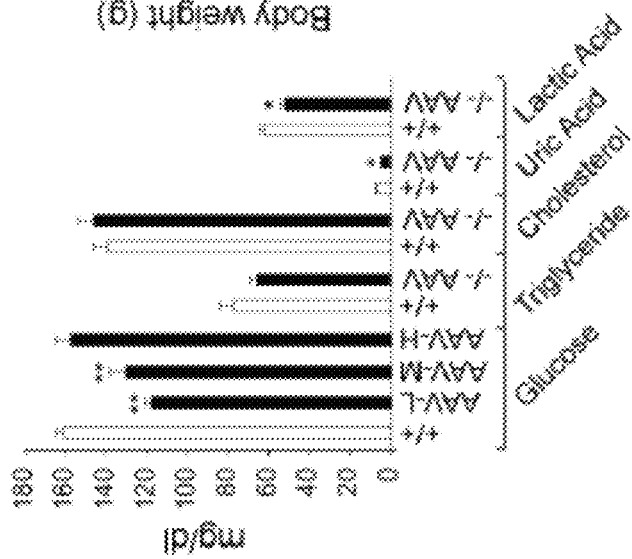
Figure 3B:
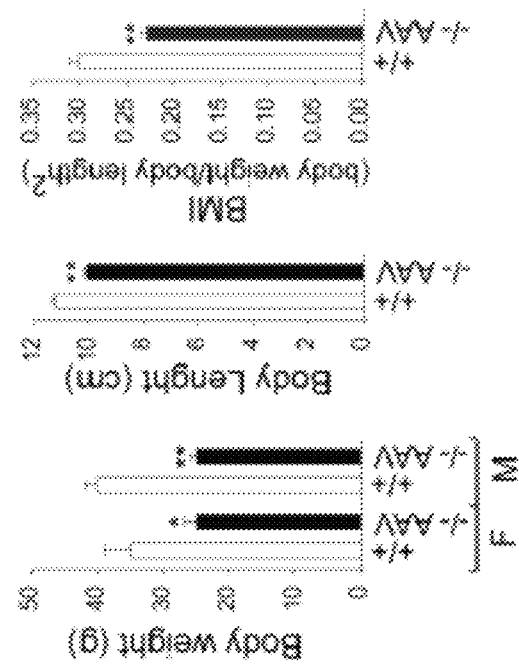
Figure 3C:
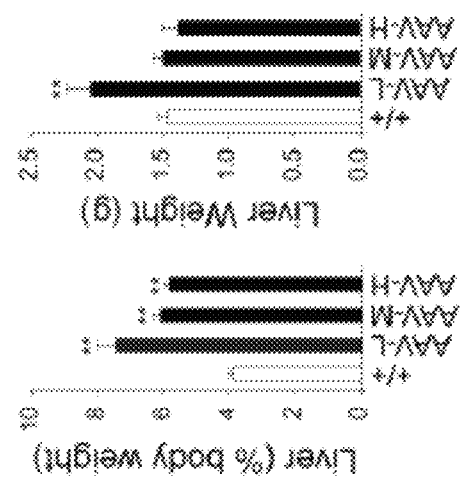

FIGS. 3A-3C are graphs showing the results of phenotype analysis of AAV-GPE-treated G6pc$^{-/-}$ $^{mice\ at\ age}$ 70 to 90 weeks. (FIG. 3A) Blood glucose, cholesterol, triglyceride, uric acid, and lactic acid levels. (FIG. 3B) Body weight, body length, and BMI. F, females; M, males. (FIG. 3C) Liver weight. Treatments are indicated as: (+/+), wild type mice; (−/− AAV), G6pc$^{-/-}$ mice infused with various dosages of AAV-GPE. AAV-L (n=6), AAV-M (n=9), and AAV-H (n=5) are AAV-GPE-treated G6pc$^{-/-}$ mice expressing 3-9% (low, L), 22-63% (medium, M), and 81-128% (high, H) normal hepatic G6Pase-α activity, respectively. Data are presented as mean±SEM. *P<0.05, **P<0.005.

Figure 4A:
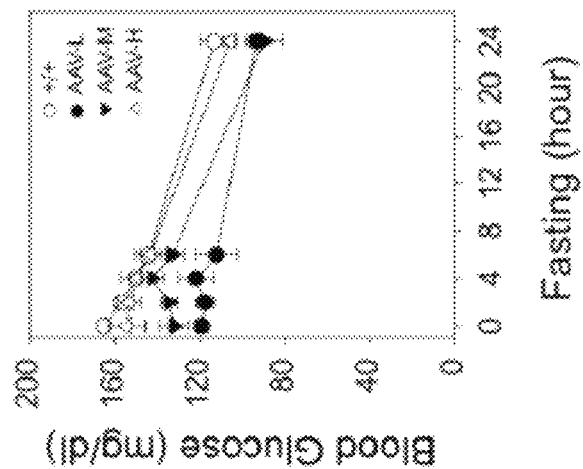
Figure 4B:
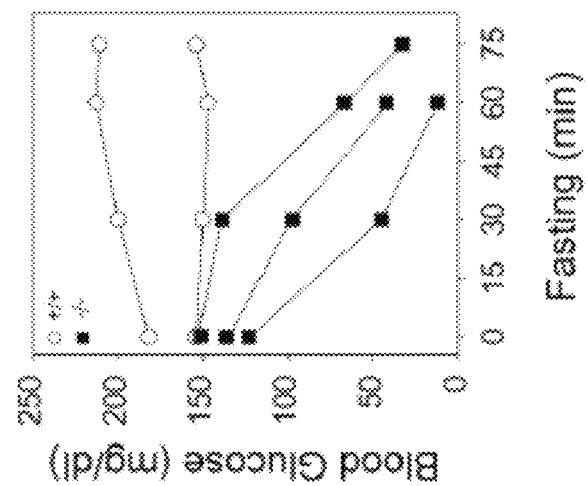
Figure 4C:
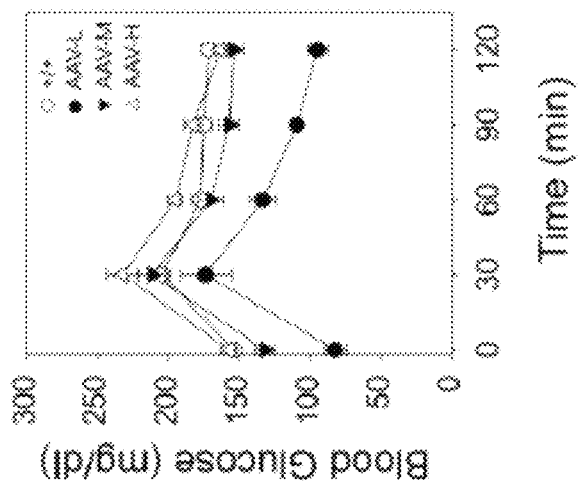

FIGS. 4A-4C are graphs showing fasting blood glucose and glucose tolerance profiles. (FIG. 4A) Fasting blood glucose profiles in wild type and AAV-GPE-treated G6pc$^{-/-}$ mice at age 70 to 90 weeks. (FIG. 4B) Fasting blood glucose profiles in untreated G6pc$^{-/-}$ mice at age 6-8 weeks. (FIG. 4C) Glucose tolerance profiles in wild type and AAV-GPE-treated G6pc$^{-/-}$ mice at age 70 to 90 weeks. Wild type or AAV-GPE-infused G6pc$^{-/-}$ mice were fasted for 6 hours, injected intraperitoneally with 2 mg/g of dextrose, and then sampled for blood every 30 minutes via the tail vein. Data are presented as mean±SEM. (+/+), wild type mice; (−/−), untreated G6pc$^{-/-}$ mice. AAV-L (n=6), AAV-M (n=9), and AAV-H (n=5) are AAV-GPE-treated G6pc$^{-/-}$ mice expression 3-9%, 22-63%, and 81-129% normal hepatic G6Pase-α activity, respectively.

FIGS. 5A-5C are graphs showing blood insulin and hepatic mRNA levels for SREBP-1c and glucokinase in 70 to 90 week-old wild type and AAV-GPE-treated G6pc$^{-/-}$ mice after 24 hours of fast. (FIG. 5A) Fasting blood insulin levels and their relationship to body weights of the animals. (FIG. 5B) Quantification of SREBP-1c mRNA by real-time RT-PCR. (FIG. 5C) Quantification of glucokinase mRNA and the relationship of fasting blood insulin to hepatic glucokinase mRNA levels. (+/+, ○), wild type mice (n=20); (−/− AAV, ●) AAV-GPE-treated G6pc$^{-/-}$ mice (n=20). Data are presented as mean±SEM. **P<0.005.

FIGS. 6A-6D are graphs showing the results of biochemical analyses in 12-week-old wild type, rAAV-GPE- and rAAV-miGPE-treated G6pc−/− mice. rAAV-GPE and rAAV-miGPE are rAAV vectors expressing human G6Pase directed by the 2864-bp of the human G6PC promoter/enhancer (GPE) and the 382-bp minimal human G6PC promoter/enhancer (miGPE), respectively. (FIG. 6A) Hepatic microsomal G6Pase-α activity and its relationship to vector genome copy numbers. (FIG. 6B) Growth curve. (FIG. 6C) BMI values. (FIG. 6D) Blood glucose levels. GPE-high, high dose rAAV-GPE-treated (○); miGPE-high, high dose rAAV-miGPE-treated (●); GPE-low, low dose rAAV-GPE-treated (□); miGPE-low, low dose rAAV-miGPE-treated (■) G6pc−/− mice; (+/+), wild type (▼) mice. Data are mean±SEM. *P<0.05.

Figure 7C:
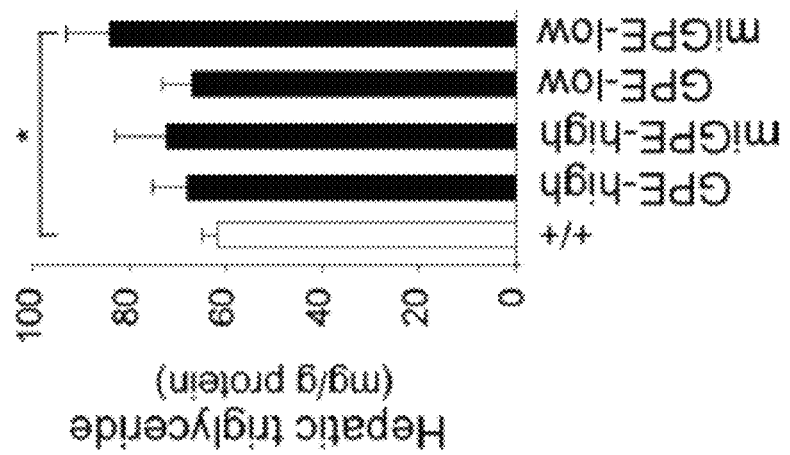
Figure 7B:
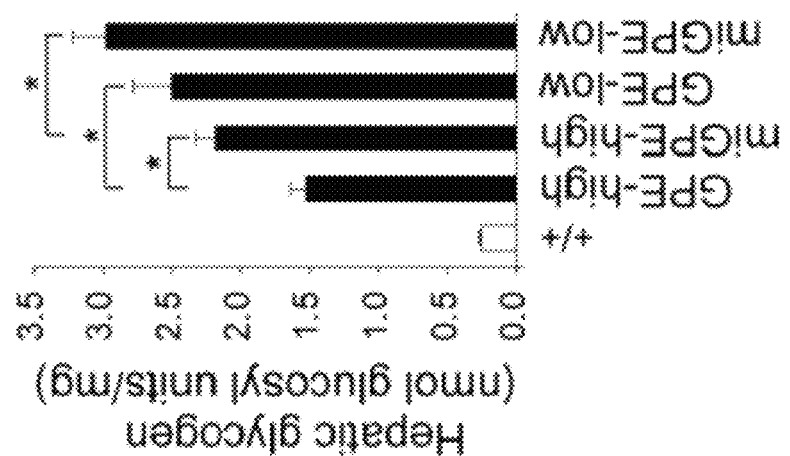
Figure 7A:

FIGS. 7A-7C are graphs showing the results of phenotypic analyses in 12-week-old wild type, rAAV-GPE- and rAAV-miGPE-treated G6pc−/− mice. (FIG. 7A) Liver weight. (FIG. 7B) Hepatic glycogen contents. (FIG. 7C) Hepatic triglyceride contents. GPE-high (n=6), high dose rAAV-GPE-treated; miGPE-high (n=6), high dose rAAV-miGPE-treated; GPE-low (n=6), low dose rAAV-GPE-treated; miGPE-low (n=6), low dose rAAV-miGPE-treated G6pc−/− mice; (+/+), wild type mice. Data are mean±SEM. *P<0.05.

Figure 8C:
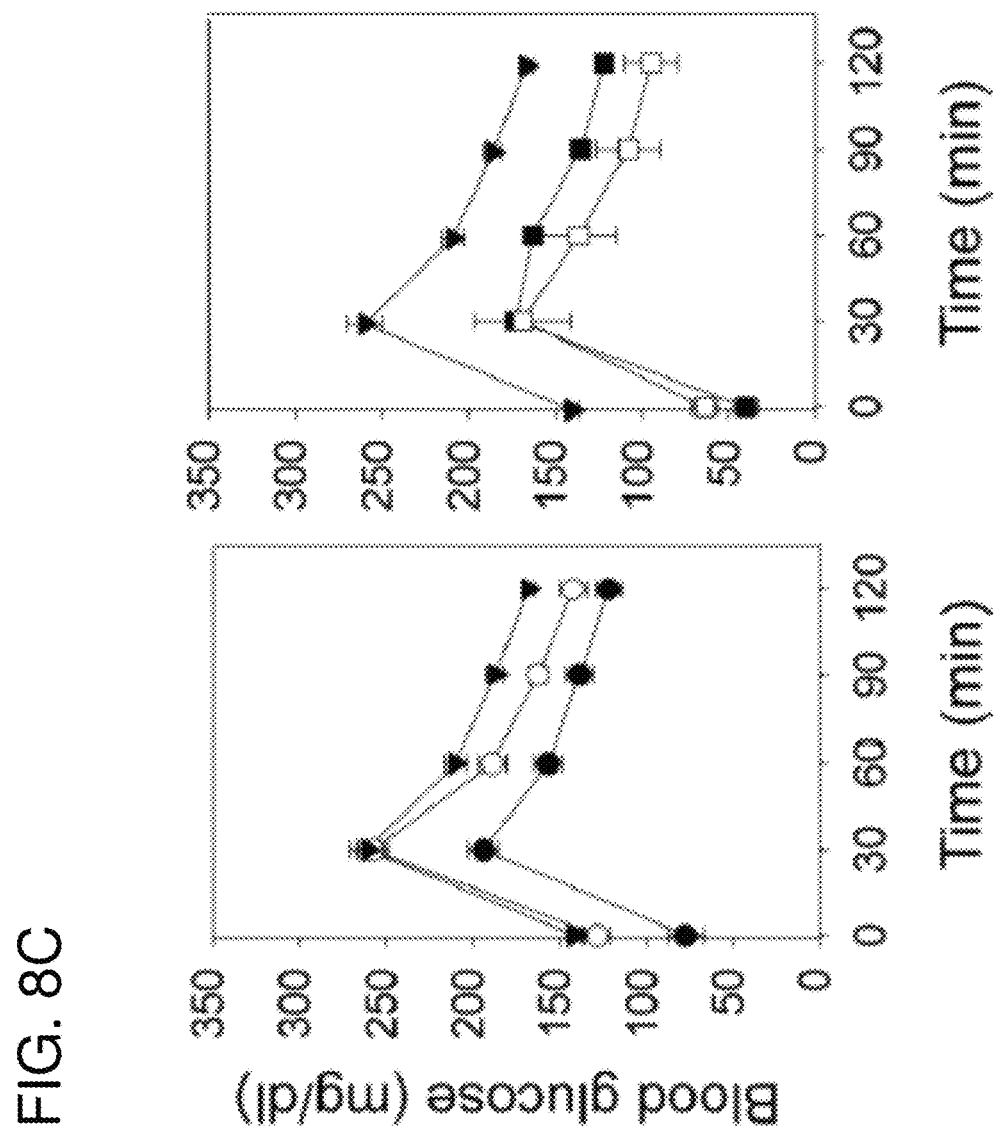

FIGS. 8A-8C are graphs showing fasting blood glucose and glucose tolerance profiles in 12-week-old wild type, rAAV-GPE- and rAAV-miGPE-treated G6pc−/− mice. (FIG. 8A) Fasting blood glucose profiles. (FIG. 8B) Blood glucose levels following a 24-hour fast. (FIG. 8C) Glucose tolerance profiles. GPE-high (n=6), high dose rAAV-GPE-treated (○); miGPE-high (n=6), high dose rAAV-miGPE-treated (●); GPE-low (n=6), low dose rAAV-GPE-treated (□); miGPE-low (n=6), low dose rAAV-miGPE-treated (■) G6pc−/− mice; (+/+), wild type mice (n=24) (▼). Data are mean±SEM. *P<0.05, **P<0.005.

Figure 9:
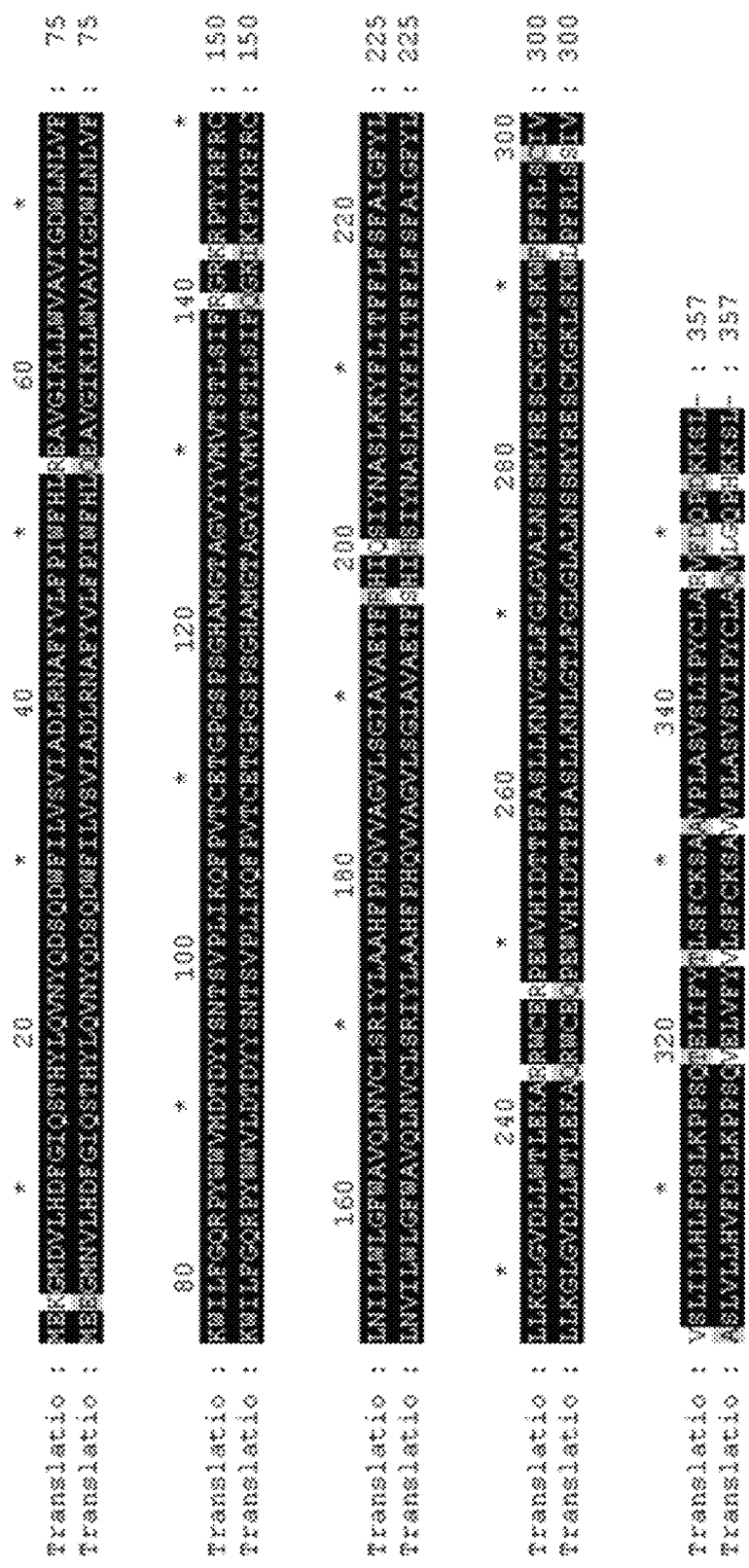

FIG. 9 is an alignment of the canine (SEQ ID NO: 10) and human (SEQ ID NO: 4) G6Pase-α protein sequences.

FIG. 10 is a table showing the amino acid differences between human, mouse, rat and canine G6Pase-α.

Figure 11:
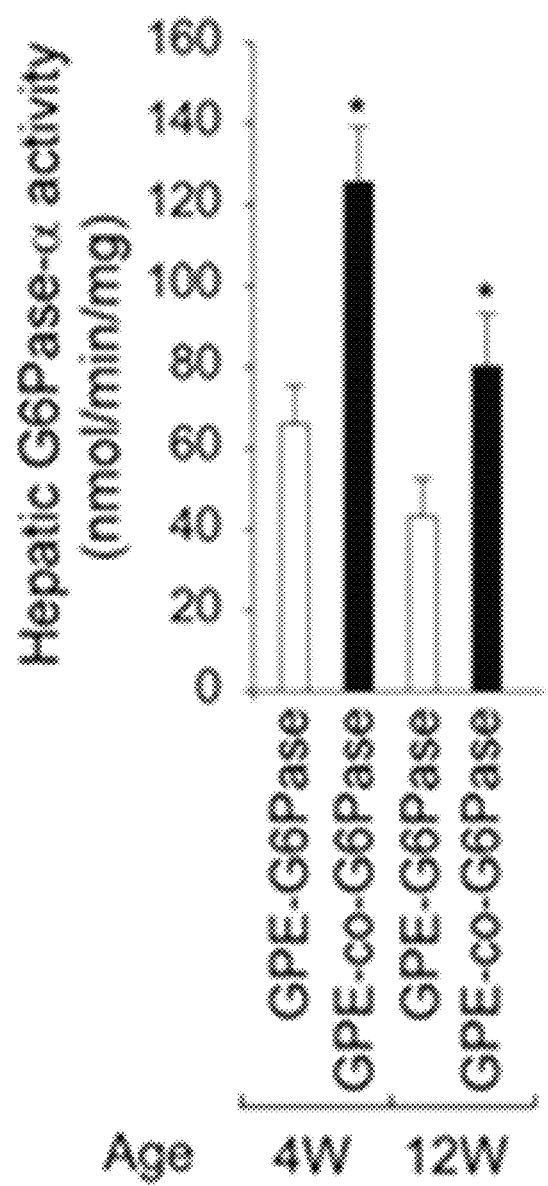

FIG. 11 is a graph showing hepatic G6Pase activity in GSD-Ia mice transduced with rAAV. GSD-Ia mice were transduced with a rAAV8 vector ($10^{13}$ vg/kg) expressing either the native or the codon-optimized (co) human G6Pase directed by the GPE promoter/enhancer. Hepatic G6Pase activity in 12-week old mice was 165.4±18.2 nmol/min/mg.

Figure 12:
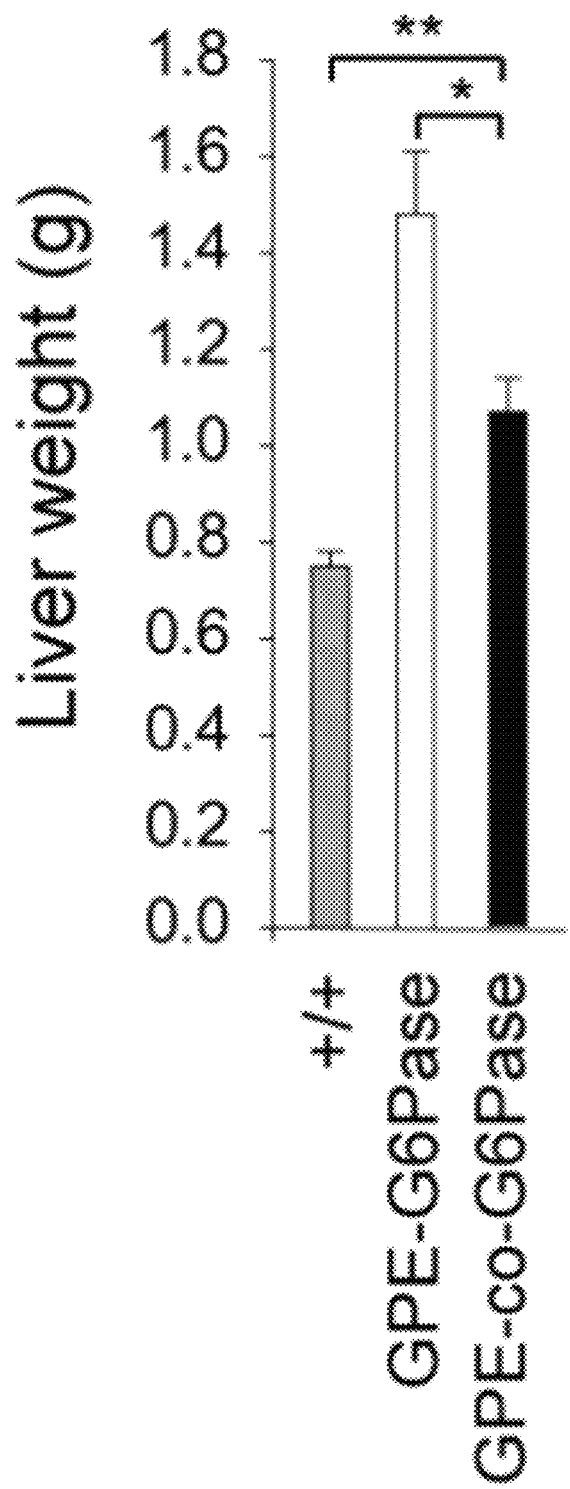

FIG. 12 is a graph showing liver weight in 12-week old wild type (+/+) and rAAV-treated GSD-Ia mice.

Figure 13B:
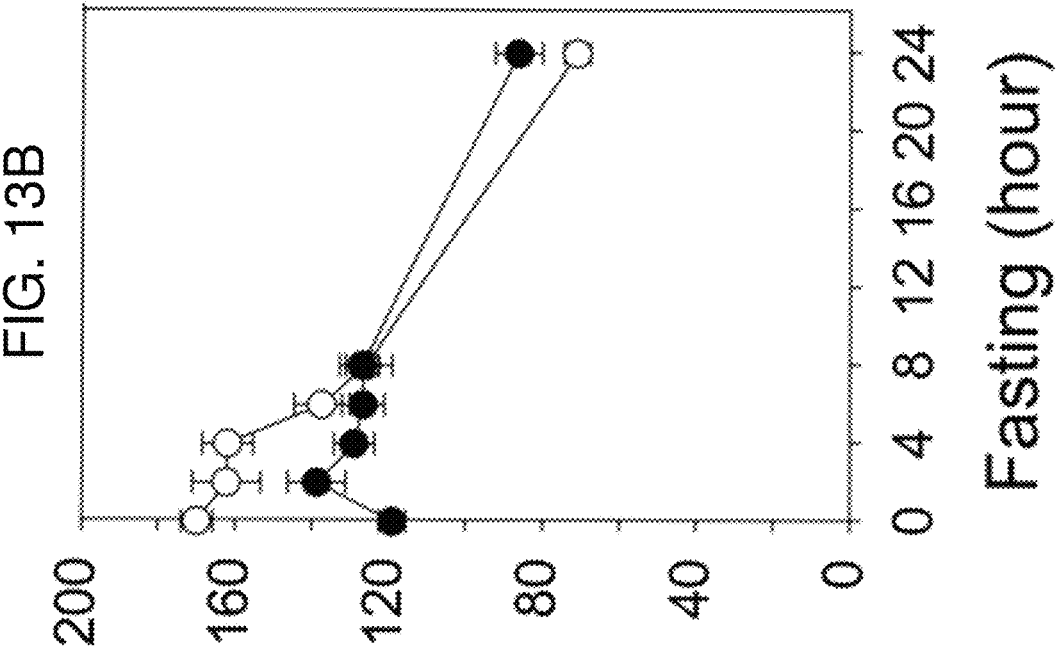
Figure 13A:
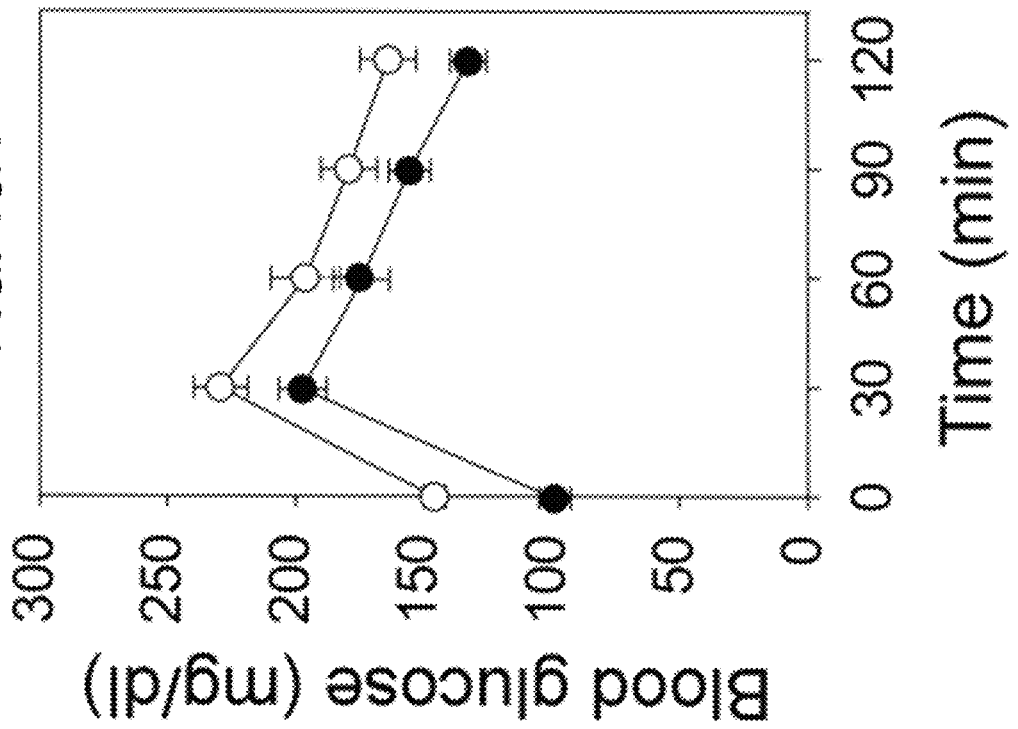

FIGS. 13A and 13B are graphs showing glucose tolerance fasting blood glucose profiles, respectively, in 12-week old wild type (○) and rAAV8-GPE-co-G6Pase-treated GSD-Ia (●) mice.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 13, 2017, 39.8 KB, which is incorporated by reference herein. In the accompanying Sequence Listing:

SEQ ID NO: 1 is the nucleotide sequence of the UF11-GPE-G6PC plasmid, including the following features:
 ITR—nucleotides 17-163
 G6PC promoter/enhancer—nucleotides 182-3045
 Stuffer—nucleotides 3051-3184
 Intron—nucleotides 3185-3321
 Stuffer—nucleotides 3322-3367
 G6PC coding sequence—nucleotides 3368-4441
 ITR—nucleotides 4674-4819

SEQ ID NO: 2 is the nucleotide sequence of the UF11-K29-G6PC plasmid, including the following features:
  ITR—nucleotides 17-163
  G6PC promoter/enhancer—nucleotides 182-3045
  Intron—nucleotides 3052-3188
  G6PC coding sequence—nucleotides 3202-4275
  ITR—nucleotides 4508-4653

SEQ ID NO: 3 is the nucleotide sequence of the UF11-GPE-co-G6PC plasmid, including the following features:
  ITR—nucleotides 17-163
  G6PC promoter/enhancer—nucleotides 182-3045
  Stuffer—nucleotides 3051-3184
  Intron—nucleotides 3185-3321
  Stuffer—nucleotides 3322-3367
  G6PC coding sequence—nucleotides 3368-4441
  ITR—nucleotides 4674-4819

SEQ ID NO: 4 is the amino acid sequence of the human G6PC protein.

SEQ ID NOs: 5-8 are primer sequences.

SEQ ID NO: 9 is the nucleotide sequence of canine G6PC.

SEQ ID NO: 10 is the amino acid sequence of canine G6PC.

DETAILED DESCRIPTION

I. Abbreviations
  AAV adeno-associated virus
  BMI body mass index
  CBA chicken β-actin
  CMV cytomegalovirus
  ELISA enzyme linked immunosorbent assay
  G6P glucose-6-phosphate
  G6PC glucose-6-phosphatase, catalytic subunit
  G6PT glucose-6-phosphate transporter
  GPE G6PC promoter/enhancer
  GSD glycogen storage disease
  H&E hematoxylin & eosin
  HCA hepatocellular adenoma
  HCC hepatocellular carcinoma
  ITR inverted terminal repeat
  ORF open reading frame
  rAAV recombinant AAV
  vg viral genomes
  vp viral particles II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 11 recognized serotypes of AAV (AAV1-11).

Administration/Administer: To provide or give a subject an agent, such as a therapeutic agent (e.g. a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Enhancer: A nucleic acid sequence that increases the rate of transcription by increasing the activity of a promoter.

G6PC: A gene located on human chromosome 17q21 that encodes glucose-6-phosphatase-α (G6Pase-α). G6Pase-α is a 357 amino acid hydrophobic protein having 9 helices that anchor it in the endoplasmic reticulum (Chou et al., *Nat Rev Endocrinol* 6:676-688, 2010). The G6Pase-α protein catalyzes the hydrolysis of glucose 6-phosphate to glucose and phosphate in the terminal step of gluconeogenesis and glycogenolysis and is a key enzyme in glucose homeostasis. Mutations in the G6PC gene cause glycogen storage disease type Ia (GSD-Ia), which is a metabolic disorder characterized by severe fasting hypoglycemia associated with the accumulation of glycogen and fat in the liver and kidneys.

Glycogen storage disease (GSD): A group of diseases that result from defects in the processing of glycogen synthesis or breakdown within muscles, liver and other tissues. GSD can either be genetic or acquired. Genetic GSD is caused by any inborn error of metabolism involved in these processes. There are currently 11 recognized glycogen storage diseases (GSD type I, II, III, IV, V, VI, VII, IX, XI, XII and XIII). GSD-I consists of two autosomal recessive disorders, GSD-Ia and GSD-Ib (Chou et al., *Nat Rev Endocrinol* 6:676-688, 2010). GSD-Ia results from a deficiency in glucose-6-phosphatase-α. Deficiencies in the glucose-6-phosphate transporter (G6PT) are responsible for GSD-Ib.

Glycogen storage disease type Ia (GSD-Ia): Also known as von Gierke disease, GSD-Ia is the most common glycogen storage disease, having an incidence of about 1 in 100,000 live births. GSD-Ia is a genetic disease resulting from deficiency of the enzyme glucose-6-phosphatase-α (G6Pase-α). Deficiency in G6Pase-α impairs the ability of the liver to produce free glucose from glycogen and from gluconeogenesis. Patients affected by GSD-Ia are unable to maintain glucose homeostasis and present with fasting hypoglycemia, growth retardation, hepatomegaly, nephromegaly, hyperlipidemia, hyperuricemia, and lactic academia (Chou et al., *Nat Rev Endocrinol* 6:676-688, 2010). There is currently no cure for GSD-Ia.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are essential cis components for generating AAV integrating vectors.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as GSD-Ia) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements which can be located as much as several thousand base pairs from the start site of transcription.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule (such as a recombinant nucleic acid molecule encoding G6Pase-α) has been packaged.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Stuffer sequence: Refers to a sequence of nucleotides contained within a larger nucleic acid molecule (such as a vector) that is typically used to create desired spacing between two nucleic acid features (such as between a promoter and a coding sequence), or to extend a nucleic acid molecule so that it is of a desired length. Stuffer sequences do not contain protein coding information and can be of unknown/synthetic origin and/or unrelated to other nucleic acid sequences within a larger nucleic acid molecule.

Subject: Living multi-cellular vertebrate organisms, a category that includes human and non-human mammals.

Synthetic: Produced by artificial means in a laboratory, for example a synthetic nucleic acid can be chemically synthesized in a laboratory.

Therapeutically effective amount: A quantity of a specified pharmaceutical or therapeutic agent (e.g. a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein are recombinant nucleic acid molecules, AAV vectors and recombinant AAV that can be used in gene therapy applications for the treatment of glycogen storage disease, specifically GSD-Ia.

The recombinant nucleic acid molecules include a G6PC promoter/enhancer (GPE), a synthetic intron, and the G6PC coding region. The G6PC coding region is optionally codon-optimized for expression in human cells. The recombinant nucleic acid molecules further include stuffer nucleic acid sequence situated between the G6PC promoter/enhancer and the intron, as well as between the intron and the G6PC coding sequence. The recombinant nucleic acid molecules can further include 5' and 3' inverted terminal repeat (ITR) sequences when encompassed within an AAV vector.

It is disclosed herein that a G6Pase-α expressing recombinant AAV with the G6PC promoter/enhancer (AAV-GPE) is significantly more efficient in directing in vivo hepatic transgene expression than another G6Pase-α expressing recombinant AAV having an alternative promoter/enhancer (i.e. the chicken β-actin promoter/CMV enhancer). Over a 24-week study period, G6PC-deficient mice (a model for GSD-Ia) treated with AAV-GPE exhibited complete normalization of hepatic G6PC deficiency as evidenced by normal levels of blood glucose, blood metabolites, hepatic glycogen and hepatic fat (see Example 1 and Yiu et al., *Mol Ther* 18:1076-1084, 2010). Furthermore, a longer-term study of AAV-GPE-treated G6pc$^{-/-}$ mice demonstrated that gene therapy mediated by AAV-GPE was efficacious for at least 70-90 weeks in mice expressing more than 3% hepatic G6Pase-α. In particular, AAV-GPE-treated mice exhibited normal hepatic fat storage, normal blood metabolite and glucose tolerance profiles, reduced fasting blood insulin levels, and had no evidence of hepatic abnormalities, such as hepatocellular adenoma (see Example 2 and Lee et al., *Hepatology* 56:1719-1729, 2012).

Further disclosed herein is the finding that the upstream enhancer elements of the G6PC promoter are critical for optimal G6PC expression in an animal model of GSD-Ia. Specifically, it is demonstrated that treatment with AAV-GPE, which comprises the G6PC promoter/enhancer at nucleotides −2684 to −1 (relative to the G6PC start site) produces significantly higher levels of hepatic G6Pase-α expression, achieved greater reduction in hepatic glycogen accumulation, and led to a better toleration of fasting in a mouse model of GSD-Ia, compared to a G6Pase-α expressing recombinant AAV containing only a 383 bp minimal G6PC promoter/enhancer (see Example 3 and Lee et al., *Mol Genet Metab.* 110(3):275-280, 2013).

Also disclosed herein is the finding that stuffer nucleotide sequences present between the G6PC promoter/enhancer and the intron, as well as between the intron and the G6PC coding sequence, are important for liver transduction and expression of G6Pase-α. In particular, recombinant AAV produced from plasmid UF11-K29-G6PC (SEQ ID NO: 2) which lacks the stuffer sequences, exhibited G6Pase activity of 7.3 nmol/min/mg. In comparison, recombinant AAV produced from plasmid UF11-GPE-G6PC (SEQ ID NO: 1) exhibited G6Pase activity of 33.0 nmol/min/mg (see Example 4). The present disclosure provides the first description of the stuffer sequences present in the AAV vectors set forth herein as SEQ ID NO: 1 and SEQ ID NO: 3.

In addition, data disclosed herein demonstrates that codon-optimization of the G6PC coding sequence increases efficiency of translation approximately 1.5- to 2.5-fold, resulting in significantly greater G6Pase-α expression in the liver following administration of AAV-co-GPE (containing a codon-optimized G6PC nucleic acid sequence), compared with administration of AAV-GPE, which encodes wild-type G6PC (see Example 5).

Taken together, these results indicate that recombinant AAV comprising the G6PC promoter/enhancer at nucleotides −2684 to −1, a synthetic intron, stuffer sequences flanking the intron, and the G6PC coding region (wild-type or codon-optimized) are critical features for efficient hepatic transgene expression and treatment of GSD-Ia in vivo.

Provided herein are recombinant nucleic acid molecules comprising a nucleotide sequence that is at least 80%, at least 85%, at least 90%, at least 95%, at least 96%, at least 97%, at least 98% or at least 99% identical to nucleotides 182-4441 of SEQ ID NO: 1 or nucleotides 182-4441 of SEQ ID NO: 3. For example, the nucleic acid molecule may contain nucleotide substitutions within the G6PC coding region, such as for codon optimization. As another example, the G6PC coding region may be a G6PC from a different species, such as canine G6PC or a codon-optimized (for expression in humans) version of canine G6PC. In some examples, the G6PC coding region set forth as nucleotides 182-3045 SEQ ID NO: 1 or nucleotides 182-3045 of SEQ ID NO: 3 is replaced with the canine G6PC coding sequence (SEQ ID NO: 9). Alternatively, the human G6PC coding region of SEQ ID NO: 1 or SEQ ID NO: 3 can contain nucleotide substitutions that result in coding changes at residues that differ between the canine and human G6PC protein sequences. For example, nucleotide substitutions can be introduced to result in coding changes at residues 3, 54, 139, 196, 199, 242, 247, 292, 298, 301, 318, 324, 332, 347, 349, 350 and/or 353 of the human G6PC protein (SEQ ID NO: 4). FIG. 9 shows an alignment of the human and canine G6Pase-α protein sequences and FIG. 10 provides a table showing the amino acid differences between human, mouse, rat and canine G6Pase-α. The present disclosure contemplates nucleotide substitutions that alter the amino acid sequence at any of the residues listed in FIG. 10.

In other instances, nucleotide substitutions may be present in the stuffer sequence or in the sequence of the synthetic intron. Nucleotide substitutions are also likely to be tolerated within the vector sequence, such as vector sequence downstream (i.e. 3' to) the 3' ITR, or between the 5' ITR and GPE, or between the G6PC coding region and the 3' ITR. In some embodiments, the recombinant nucleic acid molecules comprise nucleotides 182-4441 of SEQ ID NO: 1 or nucleotides 182-4441 of SEQ ID NO: 3. These recombinant nucleic acid molecules include the sequence of the G6PC promoter/enhancer at nucleotides −2684 to −1, a synthetic intron, stuffer sequences flanking the intron, and the G6PC coding region. SEQ ID NO: 1 includes a wild-type G6PC coding sequence, while SEQ ID NO: 3 includes a codon-optimized G6PC coding sequence.

In some embodiments, the recombinant nucleic acid molecules further include 3' and 5' ITR sequences. Thus, provided are recombinant nucleic acid molecules comprising a nucleotide sequence that is at least 80%, at least 85%, at least 90%, at least 95%, at least 96%, at least 97%, at least 98% or at least 99% identical to nucleotides 17-4819 of SEQ ID NO: 1 or nucleotides 17-4819 of SEQ ID NO: 3. In some embodiments, the recombinant nucleic acid molecules comprise nucleotides 17-4819 of SEQ ID NO: 1 or nucleotides 17-4819 of SEQ ID NO: 3. In particular non-limiting examples, the recombinant nucleic acid molecules comprise the complete sequence of SEQ ID NO: 1 (the UF11-GPE-G6PC plasmid used to generate AAV-GPE) or SEQ ID NO: 3 (the UF11-GPE-co-G6PC plasmid used to generate codon-optimized AAV-co-GPE). In other examples, the recombinant nucleic acid molecules comprise a nucleotide sequence that is at least 80%, at least 85%, at least 90%, at least 95%, at least 96%, at least 97%, at least 98% or at least 99% identical to SEQ ID NO: 1 or SEQ ID NO: 3.

In other embodiments, provided is a recombinant nucleic acid molecule comprising a nucleotide sequence that is at least 80%, at least 85%, at least 90%, at least 95%, at least 96%, at least 97%, at least 98% or at least 99% identical to nucleotides 182-4275 of SEQ ID NO: 2. In some examples, the recombinant nucleic molecule comprises nucleotides 182-4275 of SEQ ID NO: 2. In some examples, the recombinant nucleic acid molecule comprises a nucleotide sequence that is at least 80%, at least 85%, at least 90%, at least 95%, at least 96%, at least 97%, at least 98% or at least 99% identical to nucleotides 17-4653 of SEQ ID NO: 2. In some examples, the recombinant nucleic acid molecule comprises nucleotides 17-4653 of SEQ ID NO: 2. In specific non-limiting examples, the recombinant nucleic acid molecule comprises the complete sequence of SEQ ID NO: 2 (the UF11-K29-G6PC plasmid that lacks stuffer sequence). In other examples, the recombinant nucleic acid molecule comprises a nucleotide sequence that is at least 80%, at least 85%, at least 90%, at least 95%, at least 96%, at least 97%, at least 98% or at least 99% identical to SEQ ID NO: 2.

Further provided are vectors comprising the recombinant nucleic acid molecules disclosed herein. In some embodiments, the vector is an AAV vector. The AAV serotype can be any suitable serotype for delivery of transgenes to a subject. In some examples, the AAV vector is a serotype 8 AAV (AAV8). In other examples the AAV vector is a serotype 1, 2, 3, 4, 5, 6, 7, 9, 10, 11 or 12 vector (i.e. AAV1, AAV2, AAV3, AAV4, AAV5, AAV6, AAV7, AAV9, AAV10, AAV11 or AAV12). In yet other examples, the AAV vector is a hybrid of two or more AAV serotypes (such as, but not limited to AAV2/1, AAV2/7, AAV2/8 or AAV2/9). The selection of AAV serotype will depend in part on the cell type(s) that are targeted for gene therapy. For treatment of GSD-Ia, the liver and kidney are the relevant target organs.

Also provided herein are isolated host cells comprising the recombinant nucleic acid molecules or vectors disclosed herein. For example, the isolated host cell can be a cell (or cell line) appropriate for production of recombinant AAV (rAAV). In some examples, the host cell is a mammalian cell, such as a HEK-293, BHK, Vero, RD, HT-1080, A549, Cos-7, ARPE-19, or MRC-5 cell.

Further provided are rAAV comprising a recombinant nucleic acid molecule disclosed herein. In some embodiments, the rAAV is rAAV8 and/or rAAV2. However, the AAV serotype can be any other suitable AAV serotype, such as AAV1, AAV2, AAV3, AAV4, AAV5, AAV6, AAV7, AAV9, AAV10, AAV11 or AAV12, or a hybrid of two or more AAV serotypes (such as, but not limited to AAV2/1, AAV2/7, AAV2/8 or AAV2/9). Compositions comprising a rAAV disclosed herein and a pharmaceutically acceptable carrier are also provided by the present disclosure. In some embodiments, the compositions are formulated for intravenous or intramuscular administration. Suitable pharmaceutical formulations for administration of rAAV can be found, for example, in U.S. Patent Application Publication No. 2012/0219528.

Further provided are methods of treating a subject diagnosed with a glycogen storage disease, comprising selecting a subject with GSD-Ia and administering to the subject a therapeutically effective amount of a rAAV (or a composition comprising a rAAV) disclosed herein. In some embodiments, the rAAV is administered intravenously.

In some embodiments, the rAAV is administered at a dose of about $1 \times 10^{11}$ to about $1 \times 10^{14}$ viral particles (vp)/kg. In some examples, the rAAV is administered at a dose of about $1 \times 10^{12}$ to about $8 \times 10^{13}$ vp/kg. In other examples, the rAAV is administered at a dose of about $1 \times 10^{13}$ to about $6 \times 10^{13}$ vp/kg. In specific non-limiting examples, the rAAV is administered at a dose of at least about $1 \times 10^{11}$, at least about $5 \times 10^{11}$, at least about $1 \times 10^{12}$, at least about $5 \times 10^{12}$, at least about $1 \times 10^{13}$, at least about $5 \times 10^{13}$, or at least about $1 \times 10^{14}$ vp/kg. In other non-limiting examples, the rAAV is administered at a dose of no more than about $5 \times 10^{11}$, no more than about $1 \times 10^{12}$, no more than about $5 \times 10^{12}$, no more than about $1 \times 10^{13}$, no more than about $5 \times 10^{13}$, or no more than about $1 \times 10^{14}$ vp/kg. In one non-limiting example, the rAAV is administered at a dose of about $1 \times 1012$ vp/kg. The rAAV can be administered in a single dose, or in multiple doses (such as 2, 3, 4, 5, 6, 7, 8, 9 or 10 doses) as needed for the desired therapeutic results.

IV. Recombinant AAV for Gene Therapy Applications

AAV belongs to the family *Parvoviridae* and the genus *Dependovirus*. AAV is a small, non-enveloped virus that packages a linear, single-stranded DNA genome. Both sense and antisense strands of AAV DNA are packaged into AAV capsids with equal frequency.

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21(4):583-593, 2008).

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008).

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, *Clin Microbiol Rev* 21(4):583-593, 2008).

Methods for producing rAAV suitable for gene therapy are well known in the art (see, for example, U.S. Patent Application Nos. 2012/0100606; 2012/0135515; 2011/0229971; and 2013/0072548; and Ghosh et al., *Gene Ther* 13(4):321-329, 2006), and can be utilized with the recombinant nucleic acid molecules and methods disclosed herein.

The following examples are provided to illustrate certain particular features and/or embodiments. These examples should not be construed to limit the disclosure to the particular features or embodiments described.

EXAMPLES

Example 1

Complete Normalization of Hepatic G6PC Deficiency of Glycogen Storage Disease Type Ia Using Gene Therapy This example describes a comparison of two AAV vectors expressing G6Pase-α, driven by two different promoters, in efficiency of hepatic gene delivery and expression of G6Pase-α in G6PC-deficient mice. The results demonstrate that the AAV vector with the G6PC promoter/enhancer (AAV-GPE) was more efficient in directing persistent in vivo hepatic transgene expression than the AAV vector with the chicken β-actin promoter/CMV enhancer (AAV-CBA). In addition, G6PC-deficient mice treated with AAV-GPE exhibited normal levels of blood glucose, blood metabolites, hepatic glycogen and hepatic fat.

Materials and Methods

Construction of pUF11-GPE-G6PC and preparation AAV vectors

The UF11-GPE-G6PC plasmid, containing human G6Pase-α under the control of the human G6PC promoter/enhancer was constructed by modifying pUF11-mG6Pase-α-CBA (Ghosh et al., *Gene Ther* 13:321-329, 2006) where the murine G6Pase-α is driven by the CBA promoter/CMV enhancer (Xu et al., *Hum Gene Ther* 12:563-573, 2001) as follows: The Tkp-neo fragment from pUF11-mG6Pase-α-CBA was excised by XhoI/SphI digestion, the remaining vector gel purified, polished with T4 DNA polymerase, then self-ligated to yield pUF11-mG6Pase-α-CBA-[Tkp-neo]$^{-/-}$. The mG6Pase-α, along with the CBA promoter/CMV enhancer, in pUF11-mG6Pase-α-CBA-[Tkp-neo]$^{-/-}$ was then substituted with the human G6Pase-α cDNA at 5'-SbfI and 3'-NotI sites, yielding pUF11-G6PC. PCR was then used to clone nucleotides −2864 to −1 of the G6PC 5'-flanking region containing the human G6PC promoter/enhancer. The PCR template was a bacterial artificial chromosome containing the human G6PC gene (Invitrogen Life Technologies, Carlsbad, Calif.) and the primer pairs were: 1S (5'-CCTTTGAGAATCCACGGTGT-3'; SEQ ID NO: 5) and 2AS (5'-CCTCATTTCCTTGGCACCTC-3'; SEQ ID NO: 6), that contain additional KpnI and XbaI sites at the 5' and 3' ends, respectively. The KpnI-XbaI fragment that contains the G6PC promoter/enhancer was then ligated into the KpnI-XbaI linearized pUF11-G6PC, to yield pUF11-G6PC-GPE-1. Next, PCR was used to clone the chimeric intron from the pCI vector (Promega, Madison, Wis.) using primer pair 3S (5'-AGGTAAGTATCAAGGTTACA-3'; SEQ ID NO: 7) and 4AS (5'-ACCTGTGGAGAGAAAGGCAA-3'; SEQ ID NO: 8) that contain additional SpeI and SbfI sites at the 5' and 3' ends, respectively. This chimeric intron was then ligated as a SpeI-SbfI fragment into the SpeI-SbfI linearized large fragment of pUF11-G6PC-GPE-I, to yield pUF11-GPE-G6PC (SEQ ID NO: 1). All constructs were verified by DNA sequencing.

AAV-GPE and AAV-CBA were produced using pUF11-GPE-G6PC and pUF11-mG6Pase-α-CBA, respectively, and generated, purified, and tittered as previously described (Ghosh et al., *Gene Ther* 13:321-329, 2006). Vector genome quantitation was performed using real-time PCR with primers and probes directed against the G6PC or the CBA promoter.

Infusion of G6pc$^{-/-}$ Mice with AAV Vectors

A glucose therapy, that consists of intraperitoneal injection of 25-100 µl of 15% glucose every 12 h, was administered to the G6pc$^{-/-}$ mice as described previously (Lei et al., Nat Genet 13:203-209, 1996). Mice that survived weaning were given unrestricted access to Mouse Chow (Zeigler Bros., Inc., Gardners, Pa.).

The AAV vector was infused into 2-day-old G6pc$^{-/-}$ mice via the temporal vein, and infused into 2- or 4-week-old G6pc$^{-/-}$ mice via the retro-orbital sinus. Age-matched G6pc$^{+/+}$/G6pc$^{+/-}$ as well as 4- to 6-week-old G6pc$^{-/-}$ mice were used as controls. For the virus-infused mice, glucose therapy was terminated immediately after infusion.

Glucose tolerance testing of 12- or 14-week-old AAV-GPE-infused G6pc$^{-/-}$ mice consisted of fasting for 6 hours prior to blood sampling, followed by the injection of 0.25 ml of 10% dextrose subcutaneously, and repeated blood sampling via the tail vein every 30 minutes for an additional 2 hours.

Phosphohydrolase Assays

Microsome isolation and phosphohydrolase assays were determined essentially as described previously (Lei et al., Nat Genet 13:203-209, 1996). Reaction mixtures (100 µl) contained 50 mM cacodylate buffer, pH 6.5, 10 mM G6P and appropriate amounts of microsomal preparations were incubated at 37° C. for 10 minutes. Disrupted microsomal membranes were prepared by incubating intact membranes in 0.2% deoxycholate for 20 minutes at 0° C. Non-specific phosphatase activity was estimated by pre-incubating disrupted microsomal preparations at pH 5 for 10 minutes at 37° C., to inactivate the acid labile G6Pase-α.

Enzyme histochemical analysis of G6Pase-α was performed by incubating 10 µm thick liver tissue sections for 10 minutes at room temperature in a solution containing 40 mM Tris-maleate pH 6.5, 10 mM G6P, 300 mM sucrose, and 3.6 mM lead nitrate (Teutsch, Prog Histochem Cytochem 14:1-92, 1981). The trapped lead phosphate was visualized following conversion to the brown colored lead sulfide (Teutsch, Prog Histochem Cytochem 14:1-92, 1981).

Phenotype Analyses

Blood samples were collected from the tail vein. Blood glucose, total cholesterol, and uric acid were analyzed using kits obtained from Thermo Electron (Louisville, Colo.). Triglycerides were measured with a kit from Sigma Diagnostics (St Louis, Mo.) and lactate measured by a kit from Trinity Biotech (St. Louis, Mo.).

For hematoxylin and eosin (H&E) and oil red O staining, liver sections were preserved in 10% neutral buffered formalin, and sectioned at 4-10 microns thickness. The stained sections were visualized using the Axioskop2 plus microscope and the AxioVision 4.5 software (Carl Zeiss, Thornwood, N.Y.). For quantitative histochemical measurement of lipid accumulation, the oil red O stain was converted into pixel density units using Adobe Photoshop CS3 (Adobe System Incorporated, San Jose, Calif.).

To determine the glycogen content of the liver, tissue was homogenized with HCl, boiled for 10 minutes, and neutralized with sodium acetate to a final pH of 4.5 (Teutsch, Prog Histochem Cytochem 14:1-92, 1981). The hydrolyzed tissue was then digested with amylo-α-1,4-α-1,6-glucosidase and the released glucose was measured using a kit obtained from Sigma Diagnostics. Glycogen content is reported as nmol glucosyl units per mg of hepatic protein.

Antibody Assays

Antibodies against human or murine G6Pase-α were detected by Western-blot analysis. Microsomal proteins from Ad-human G6Pase-α or Ad-mouse G6Pase-α infected COS-1 cells (Ghosh et al., J Biol Chem 277: 32837-32842, 2002) were resolved by electrophoresis through a 12% polyacrylamide-SDS gel and trans-blotted onto polyvinylidene fluoride membranes (Millipore, Bedford, Mass.). The membrane was placed in a Multiscreen Apparatus (Bio-Rad Laboratories, Hercules, Calif.) containing multiple channels. The membrane strip under each channel was incubated with a rabbit anti-human G6Pase-α serum (Ghosh et al., J Biol Chem 277: 32837-32842, 2002) diluted 1:3000, or serum samples from AAV-GPE-infused or AAV-CBA-infused animals diluted 1:200. Serum samples from untreated G6pc$^{-/-}$ and G6pc$^{+/+}$/G6pc$^{+/-}$ littermates diluted 1:200 were used as controls. After overnight incubation, the membrane strips were then incubated with horseradish peroxidase-conjugated goat anti-rabbit IgG or goat anti-mouse IgG (Kirkegarrd & Perry Laboratories, Gaithersburg, Md.). The immunocomplex was visualized by the chemiluminescent system using the SuperSignal™ West Pico Chemiluminescent substrate from Pierce (Rockford, Ill.).

CD8+ lymphocyte immunodetection

Mouse livers were snap frozen, embedded in O.C.T. (Sakura Finetek, Terrance, Calif.), and sectioned at 8 micron thickness. The sections were fixed in acetone for 10 minutes at −20° C., dried, washed with PBS, blocked with PBS containing 2% of BSA for 30 minutes, and incubated at 4° C. overnight with a rabbit polyclonal antibody against CD8 (Abcam Inc., Cambridge, Mass.) in PBS supplemented with 1% BSA. After washes with PBS, the sections were incubated for 1 hour at 25° C. in the dark with a goat anti-rat IgG antibody conjugated with Alexa Fluor® 488 (Invitrogen) dye. Following washes with PBS, the labeled cells were mounted with an anti-fade, water-based mounting medium containing DAPI (Vector Laboratories, Burlingame, Calif.) and visualized using the Axioskop2 plus fluorescence microscope (Carl Zeiss, Thornwood, N.Y.). The CD8+ cells were counted in ten randomly selected fields at 200-fold magnification and reported as the mean average.

Statistical Analysis

The unpaired t test was performed using the GraphPad Prism® Program, version 4 (GraphPad Software, San Diego, Calif.). Values were considered statistically significant at $p<0.05$.

Results

AAV-GPE Infusion Directs Long-Term Hepatic G6Pase-α Expression

To examine the in vivo impact of sequences upstream of nucleotides −298 of the human G6PC promoter element previously studied (Koeberl et al., Mol Ther 16:665-672, 2008), AAV-GPE, an AAV8 vector expressing human G6Pase-α under the control of nucleotides −2864 to −1 of the human G6PC 5'-flanking region, was constructed. Since there is no standard age at which to initiate AAV-mediated gene therapy in mice (Ghosh et al., Gene Ther 13:321-329, 2006; Koeberl et al., Gene Ther 13:1281-1289, 2006; Koeberl et al., Mol Ther 16:665-672, 2008) and there is evidence that the loss of efficiency and persistence of gene transfer is influenced by the increased rate of hepatocellular proliferation associated with liver growth (Cunningham et al., Mol Ther 16:1081-1088, 2008), G6pc$^{-/-}$ mice were infused at three different ages, 2-day-old, 2-week-old, or 4-week-old, and hepatic G6Pase-α expression was examined out to 24 weeks of age. Despite the difference in age, each group of mice was infused with the same dose of AAV-GPE ($1.2 \times 10^{11}$ viral genomes (vg)/mouse). Metabolic profiles of the infused animals were monitored during the 24-week study and all measurements compared to those of their G6pc$^{+/+}$/G6pc$^{+/-}$ littermates and 4 to 6 week-old untreated G6pc$^{-/-}$ mice.

GSD-Ia is an autosomal recessive disorder and previous studies have shown that the phenotype of the G6pc$^{+/+}$ and G6pc$^{+/-}$ littermates are indistinguishable and wild type (Lei et al., *Nat Genet* 13:203-209, 1996).

There were no premature deaths in the infused G6pc$^{-/-}$ animals for the duration of the 24-week study, regardless of the age of infusion. In G6pc$^{-/-}$ mice infused at age 2 days with AAV-GPE (1.2×10$^{11}$ vg/mouse, equivalent to 6×10$^{13}$ vg/kg), hepatic G6Pase-α activity was 77.6% of control activity at age 2 weeks, declining to 16.2% at age 4-weeks and 6.5% of control activity at age 6 weeks (Table 1). However, beyond 6 weeks the levels of hepatic G6Pase-α activity stabilized out to 24 weeks (Table 1). Therefore expression dropped 11.9-fold over the entire 24 week study, with most of the drop occurring within the first 6 weeks.

In contrast, in G6pc$^{-/-}$ mice infused at age 2 weeks with AAV-GPE (1.2×10$^{11}$ vg/mouse, equivalent to 1.5×10$^{13}$ vg/kg) hepatic G6Pase-α activity 2 weeks post-infusion (at age 4 weeks) was 2.4-fold higher than the activity in their G6pc$^{+/+}$/G6pc$^{+/-}$ littermates (Table 1), reaching 433.4±11.1 nmol/mg/min. While hepatic G6Pase-α activity did subsequently undergo a 2.6-fold decline between ages 4 to 6 weeks, it resulted in a near normal hepatic G6Pase-α activity (174.0±22.4 nmol/mg/min) being maintained from age 6 weeks on for the duration of the 24-week study (Table 1). Similarly, in G6pc$^{-/-}$ mice infused with AAV-GPE at age 4 weeks with the same dosage (1.2×10$^{11}$ vg/mouse, equivalent to 1×10$^{13}$ vg/kg) hepatic G6Pase-α activity at age 24 weeks was 335.6±40.2 nmol/min/mg, 1.9-fold higher than the activity in the control littermates (Table 1). These findings are consistent with the previous proposal (Cunningham et al., *Mol Ther* 16:1081-1088, 2008) that the loss of efficiency and persistence of gene transfer is influenced by the increased rate of hepatocellular proliferation associated with liver growth. Injections at later stages of development, when the rate of liver growth is lower, resulted in less gene expression loss.

The distribution of the G6Pase-α transgene expression in the liver was investigated. As expected, there was no stainable G6Pase-α activity in the liver sections of untreated G6pc$^{-/-}$ mice. In G6pc$^{+/+}$/G6pc$^{+/-}$ mice, enzyme histochemical analysis showed G6Pase-α distributed throughout the liver but with significantly higher levels in proximity to blood vessels.

In G6pc$^{-/-}$ mice infused at age 2 days with AAV-GPE, hepatic G6Pase-α activity was distributed throughout the liver at age 2 weeks. Unlike wild type mice, the expression was uneven with foci that stained stronger than in the control livers. The stained G6Pase-α activity markedly decreased from age 2 to 4 weeks, consistent with a 4.8-fold decline in phosphohydrolase activity (Table 1). Again, the stained G6Pase activity decreased and stabilized at age 6 weeks and older.

In G6pc$^{-/-}$ mice infused with AAV-GPE at age 2 or 4 weeks, enzyme histochemical analyses again showed that the G6Pase-α transgene was distributed throughout the liver with foci containing significantly higher levels of enzymatic activity. Again, G6Pase-α activities estimated by histochemical analyses were in agreement with quantitative phosphohydrolase assays (Table 1). In G6pc$^{-/-}$ mice infused with AAV-GPE at age 2 weeks, there were cells in the liver that stained less intensely than cells in the wild type livers. Therefore a normal pattern of hepatic G6Pase-α expression was not restored in AAV-GPE-infused mice despite exhibiting wild type G6Pase-α activity.

TABLE 1

Hepatic G6Pase activity in G6pc$^{-/-}$ mice infused with 1.2 × 10$^{11}$ vg/mouse of AAV-GPE

| Mice | Age weeks | Phosphohydrolase Activity nmol/mg/min | Relative Activity % | % (+/+ or +/−) Activity |
|---|---|---|---|---|
| +/+ or +/− (n = 16) | 2-24 | 178.1 ± 10.0 | | 100 |
| Infusion at age 2 days | | | | |
| −/−/AAV-GPE (n = 2) | 2 | 138.3 ± 22.6 | 100 | 77.6 |
| −/−/AAV-GPE (n = 4) | 4 | 28.8 ± 9.9 | 20.8 | 16.2 |
| −/−/AAV-GPE (n = 7) | 6-24 | 11.6 ± 5.0 | 8.4 | 6.5 |
| Infusion at age 2 weeks | | | | |
| −/−/AAV-GPE (n = 2) | 4 | 433.4 ± 11.1 | 100 | 243.3 |
| −/−/AAV-GPE (n = 2) | 6 | 156.1 ± 7.0 | 36.0 | 87.6 |
| −/−/AAV-GPE (n = 3) | 24 | 174.0 ± 22.4 | 40.1 | 97.7 |
| Infusion at age 4 weeks | | | | |
| −/−/AAV-GPE (n = 3) | 24 | 335.6 ± 40.2 | | 188.4 |

G6pc$^{-/-}$ (−/−) mice were infused with 1.2 × 10$^{11}$ vg/mouse of AAV-GPE at age 2 days, 2 weeks, or 4 weeks as described under MATERIALS and METHODS. Age-matched G6pc$^{+/+}$/G6pc$^{+/-}$ (+/+ & +/−) mice were used as positive controls and 4- to 6-week-old G6pc$^{-/-}$ (−/−) mice were used as negative controls. Values in the table have been corrected for background by subtracting the G6Pase-α activity (1.8 ± 0.2 nmol/min/mg) in the liver microsomes of untreated G6pc$^{-/-}$ mice from the respective results. Data are presented as mean ± SEM.

AAV-CBA Infusion Directs Lower Levels of Hepatic G6Pase-α Expression

The CBA promoter/CMV enhancer has been widely used to direct high levels of hepatic transgene expression (Xu et al., *Hum Gene Ther* 12:563-573, 2001). However, the CMV enhancer is known to be silenced by extensive CpG and non-CpG methylation (Brooks et al., *J Gene Med* 6:395-404, 2004; Mehta et al., *Gene* 428: 20-24, 2009). Previous in vivo experiments using AAV-CBA, an AAV8 vector expressing murine G6Pase-α under the control of the hybrid CBA promoter/CMV enhancer had shown poor expression (Ghosh et al., *Gene Ther* 13:321-329, 2006), possibly related to CMV promoter methylation. To compare the in vivo efficacy of hepatic gene transfer between AAV-CBA and AAV-GPE, G6pc$^{-/-}$ mice were infused with an increased dose of AAV-CBA at 4.8×10$^{11}$ vg/mouse in a similar manner to the AAV-GPE experiments—at ages 2 days and 2 weeks and followed to 24 weeks of age.

For G6pc$^{-/-}$ mice infused at 2 days of age, hepatic G6Pase-α activity at age 2 weeks was 2.8 fold higher in AAV-CBA-infused mice compared to AAV-GPE-infused mice (Tables 1 and 2), reflecting the 4-fold higher dosage of AAV-CBA infused. However, hepatic G6Pase-α activity in the neonatally AAV-CBA-infused animals declined rapidly to 20.6±1.1 nmol/mg/min at age 4 weeks (Table 2), an 18.6-fold decline in 2 weeks, compared to a 4.8-fold decline in neonatal G6pc$^{-/-}$ mice infused with AAV-GPE (Table 1). Since the CBA and GPE are in identical vector background, this finding suggests that the CBA promoter/CMV enhancer is less efficient in directing persistent in vivo hepatic transgene expression than the G6PC promoter/enhancer.

In G6pc$^{-/-}$ mice infused with 4.8×10$^{11}$ vg/mouse of AAV-CBA at age 2 weeks, hepatic G6Pase-α activity was 236.9±64.7 at age 4 weeks (Table 2), which was 1.83-fold lower than 4-week-old G6pc$^{-/-}$ mice infused at age 2 weeks with 1.2×10$^{11}$ vg/mouse of AAV-GPE (Table 1). Moreover, hepatic G6Pase-α activity continued to decline with the CBA vector from 55.7±2.7 nmol/mg/min at age 6 weeks to 38.1±1.7 nmol/mg/min at age 24 weeks (Table 2). This was in contrast to the levels expressed with the GPE vector that stabilized over this time period at near wild type levels (Table 1).

Enzyme histochemical analyses of AAV-CBA-infused animals showed that the activity staining was similar to those of the GPE vector, unevenly distributed with numerous foci that stained stronger than that in the control livers. But consistent with the quantitative phosphohydrolase assays (Table 2), the overall stain intensities were significantly lower with increasing age of the infused mice.

TABLE 2

Hepatic G6Pase activity in G6pc$^{-/-}$ mice infused with 4.8 × 10$^{11}$ vg/mouse of AAV-CBA

| Mice | Age weeks | Phosphohydrolase Activity nmol/mg/min | Relative Activity % | % (+/+ or +/−) Activity |
|---|---|---|---|---|
| +/+ or +/− (n = 16) | 2-24 | 178.1 ± 10.0 | | |
| Infusion at age 2 days | | | | |
| −/−/AAV-CBA (n = 2) | 2 | 382.3 ± 4.2 | 100 | 214.7 |
| −/−/AAV-CBA (n = 3) | 4 | 20.6 ± 1.1 | 5.4 | 11.6 |
| Infusion at age 2 weeks | | | | |
| −/−/AAV-CBA (n = 2) | 4 | 236.9 ± 64.7 | 100 | 133.0 |
| −/−/AAV-CBA (n = 2) | 6 | 55.7 ± 2.7 | 23.5 | 31.3 |
| −/−/AAV-CBA (n = 3) | 24 | 38.1 ± 1.7 | 16.1 | 21.4 |

G6pc$^{-/-}$ (−/−) mice were infused with 4.8 × 10$^{11}$ vg/mouse of AAV-CBA at age 2 days and 2 weeks as described under MATERIALS and METHODS. Age-matched G6pc$^{+/+}$/G6pc$^{+/-}$ (+/+ & +/−) mice were used as positive controls and 4- to 6-week-old G6pc$^{-/-}$ (−/−) mice were used as negative controls. Values in the table have been corrected for background by subtracting the G6Pase-α activity (1.8 ± 0.2 nmol/min/mg) in the liver microsomes of untreated G6pc$^{-/-}$ mice from the respective results. Data are presented as mean ± SEM.

AAV-GPE Infusion Corrects Pathological Manifestations of GSD-Ia

Figure 1A:
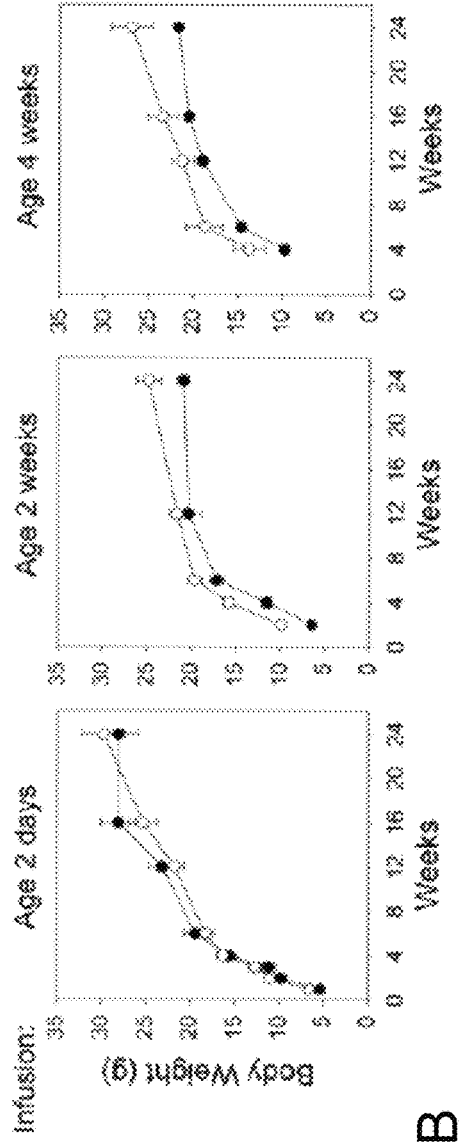
FIGS. 1A-1B are graphs showing the results of phenotype analysis of AAV-GPE-infused G6pc$^{-/-}$ mice.

G6pc$^{-/-}$ mice under glucose therapy are growth retarded and by 2 weeks of age their average body weight is approximately 60% of their G6pc$^{+/+}$/G6pc$^{+/-}$ littermates (Lei et al., Nat Genet 13:203-209, 1996). Neonatal G6pc$^{-/-}$ mice infused with AAV-GPE had a markedly improved growth rate and the body weights of the infused animals were comparable to the control mice (FIG. 1A). G6pc$^{-/-}$ mice infused at age 2 or 4 weeks with AAV-GPE exhibited a growth curve that paralleled their G6pc$^{+/+}$/G6pc$^{+/-}$ littermates but at lower values, consistent with the lower starting body weights of G6pc$^{-/-}$ mice before commencing gene therapy (FIG. 1A).

Figure 1B:
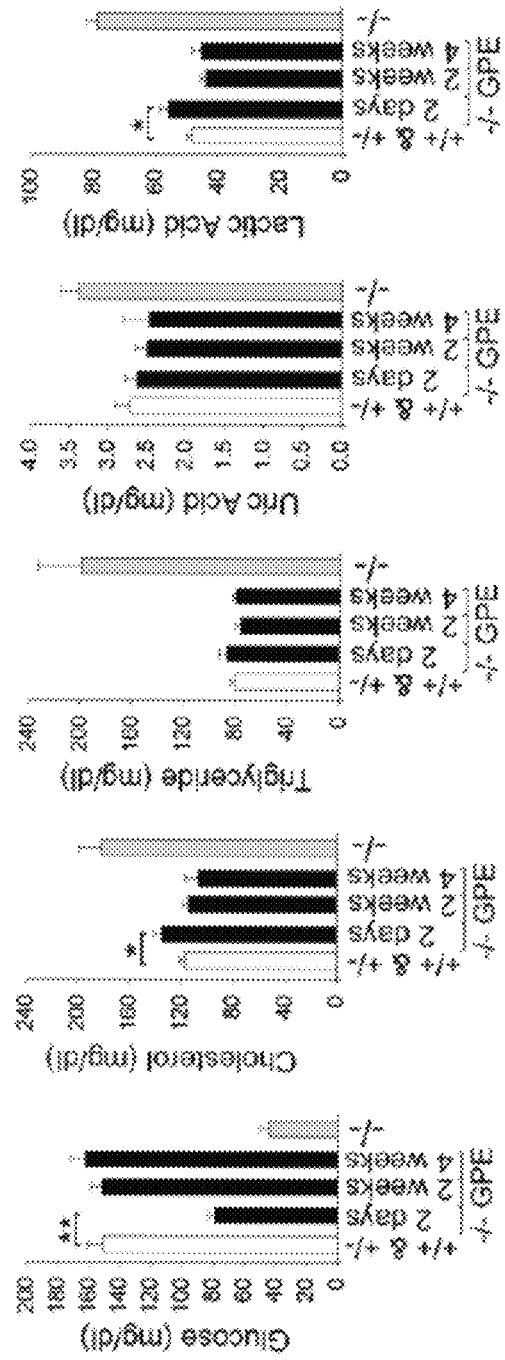

Under glucose therapy, the G6pc$^{-/-}$ mice continue to manifest hypoglycemia, hypercholesterolemia, hypertriglyceridemia, hyperuricemia, and lactic academia (Lei et al., Nat Genet 13:203-209, 1996; Kim et al., J Hepatol 48: 479-485, 2008). In contrast, the AAV-GPE-infused G6pc$^{-/-}$ mice had normal blood glucose profiles (FIG. 1B) and none of the infused animals suffered from the frequent hypoglycemic seizures typical of the untreated G6pc$^{-/-}$ mice (Lei et al., Nat Genet 13:203-209, 1996) and human GSD-Ia patients (Chou et al., Curr Mol Med 2:121-143, 2002). Blood glucose levels in neonatally infused G6pc$^{-/-}$ mice were significantly lower than their control littermates (FIG. 1B), suggesting that hepatic G6Pase-α activity restored to 6.5% of control levels is insufficient to maintain normal blood glucose profile. In contrast, blood glucose levels in G6pc$^{-/-}$ mice infused with AAV-GPE at age 2 or 4 weeks were indistinguishable from those in their control littermates (FIG. 1B). AAV-GPE infusion also normalized serum cholesterol, triglyceride, uric acid, and lactic acid levels, although neonatally infused G6pc$^{-/-}$ mice had slightly higher levels of blood cholesterol and lactic acid (FIG. 1B).

Hepatomegaly is another clinical presentation in GSD-Ia and is primarily caused by excess glycogen and lipid deposition (Chou et al., Curr Mol Med 2:121-143, 2002). No histological abnormality was observed in the liver tissue sections of the unaffected and AAV-GPE-transduced mice at age 24 weeks. Glycogen content in the liver of 24-week-old G6pc$^{+/+}$/G6pc$^{+/-}$ mice averaged 1.89±0.17 nmol glucosyl units per mg protein In neonatally AAV-GPE-infused animals the glycogen content at 24 weeks of age was significantly higher at 4.65±0.19 nmol glucosyl units per mg protein, indicative of the glycogen storage defect observed in GSD-Ia mice. In contrast, the mice receiving infusions at 2 or 4 weeks of age showed wild type levels of glycogen at 24 weeks of age, namely 1.61±0.39, and 1.65±0.19 nmol glucosyl units per mg protein, respectively, indicative of the absence of the characteristic histology of GSD-Ia disease at this stage of development.

Oil red O staining showed that the lipid contents in AAV-GPE-infused animals were similar to that in the G6pc$^{+/+}$/G6pc$^{+/-}$ littermates at age 24 weeks. For quantitative histochemical measurement, lipid imaged with Oil red O stain was converted into pixel density units using Adobe Photoshop. The density units in the liver of AAV-GPE-treated G6pc$^{-/-}$ mice were lower than those in the control mice (approximately 150 pixel density units/μm$^2$ compared with approximately 300 pixel density units/μm$^2$), although the difference was not statistically significant. Taken together, these results indicate AAV-GPE-infused G6pc$^{-/-}$ mice exhibited no histological abnormality and had normal glycogen and fat contents in the liver.

AAV-GPE-Infused G6pc$^{-/-}$ Mice Exhibit Normal Fasting Glucose and Glucose Tolerance Profile Fasting blood glucose levels were examined in 12- and 14-week-old G6pc$^{-/-}$ mice infused with AAV-GPE at age 2 and 4 weeks, respectively. Blood glucose levels in G6pc$^{+/+}$/G6pc$^{+/-}$ mice were unchanged after 6 hours of fasting. Importantly, blood glucose levels in G6pc$^{-/-}$ mice infused with AAV-GPE at either age 2 or 4 weeks were also unchanged after 6 hours of fasting, demonstrating that the infused G6pc$^{-/-}$ mice no longer suffer from fasting hypoglycemia, characteristics of GSD-Ia (Chou et al., Curr Mol Med 2:121-143, 2002). Similar fasting experiments with the untreated G6pc$^{-/-}$ mice resulted in rapid hypoglycemia followed by hypoglycemic seizures after only a short fast.

Studies have shown that over-expression of hepatic G6Pase-α may induce diabetes (Liu et al., Biochem Biophys Res Commun 205:680-686, 1994; Antinozzi et al., Annu Rev Nutr 19: 511-544, 1999; Clore et al., Diabetes 49:969-974, 2000). Since hepatic G6Pase-α activity in 24-week-old G6pc$^{-/-}$ mice infused at age 4 weeks with AAV-GPE was nearly 2-fold higher than the activity in their G6pc$^{+/+}$/G6pc$^{+/-}$ littermates, we conducted a glucose tolerance test in 14-week-old G6pc$^{-/-}$ mice infused at age 4 weeks with AAV-GPE. As a control, a glucose tolerance test was also performed in 12-week-old G6pc$^{-/-}$ mice infused at age 2 weeks with AAV-GPE. These animals exhibited wild type levels of hepatic G6Pase-α activity. Glucose tolerance profiles in the infused G6pc$^{-/-}$ mice were indistinguishable from that of control littermates.

Absence of Immune Response Against Human G6Pase-α

To determine whether a humoral response directed against human G6Pase-α is generated in the infused G6pc$^{-/-}$ mice, Western blot analysis was performed using sera from mice infused with AAV-GPE or AAV-CBA. As a positive control, a rabbit anti-human G6Pase-α antiserum that also recognizes murine G6Pase-α was used (Ghosh et al., J Biol Chem 277: 32837-32842, 2002). No antibodies directed against G6Pase-α were detected in any of the AAV-GPE-infused or AAV-CBA-infused G6pc$^{-/-}$ mice that lived to age 24 weeks. Furthermore, there were no endogenous antibodies directed against G6Pase-α present in the sera of G6pc$^{+/+}$/G6pc$^{+/-}$ littermates or untreated G6pc$^{-/-}$ mice.

AAV-CBA Infusion Elicits Increased Hepatic CD8+ Lymphocyte Infiltration

The absence of detectable antibodies against G6Pase-α in the liver of AAV-CBA-infused G6pc$^{-/-}$ mice suggests that a cell-mediated immune response to the G6Pase-α transgene is not the cause for the rapid decline in transgene expression directed by this vector. Another possibility is an inflammatory immune response elicited by the AAV-CBA vector. Therefore, hepatic CD8+ lymphocyte infiltration was examined 2 weeks following infusion of G6pc$^{-/-}$ mice with AAV-CBA or AAV-GPE. In 2- and 4-week-old wild type or G6pc$^{-/-}$ mice, hepatic CD8+ lymphocyte counts were low. In G6pc$^{-/-}$ mice infused with AAV-CBA or AAV-GPE at age 2 days, hepatic CD8+ lymphocyte counts at age 2 weeks were similar for each of the vector types and comparable to the counts in untreated 2-week-old wild type or G6pc$^{-/-}$ animals. In G6pc$^{-/-}$ mice infused with AAV-GPE at age 2 weeks, hepatic CD8+ lymphocyte counts remained low at age 4 weeks. In contrast, in G6pc$^{-/-}$ mice infused with AAV-CBA at age 2 weeks, hepatic CD8+ lymphocyte counts were markedly increased at age 4 weeks. The results suggest that an inflammatory response elicited by AAV-CBA may explain, at least in part, the rapid decline and low efficacy of hepatic G6Pase-α expression directed by the CBA promoter/CMV enhancer.

Example 2

Prevention of Hepatocellular Adenoma and Correction of Metabolic Abnormalities in Glycogen Storage Disease Type IA Using Gene Therapy This example describes studies to evaluate the efficacy of the AAV-GPE vector in a long-term study. Gene therapy mediated by the AAV-GPE vector in G6pc$^{-/-}$ mice was efficacious for at least 70-90 weeks in mice expressing more than 3% of wild-type hepatic G6Pase-α. The results demonstrated that AAV-GPE treated mice exhibit normal hepatic fat storage, normal blood metabolite and glucose tolerance profiles, reduced fasting blood insulin levels, and no evidence of hepatic abnormalities.

Materials and Methods

Infusion of G6pc$^{-/-}$ Mice with AAV-GPE

The AAV-GPE vector (as described in Example 1 and Yiu et al., Mol Ther 18:1076-1084, 2010) was infused into G6pc$^{-/-}$ mice (Lei et al., Nat Genet 13: 203-209, 1996) via the retro-orbital sinus. Age-matched G6pc$^{+/+}$/G6pc$^{+/-}$ as well as 6- to 10-week-old G6pc$^{-/-}$ mice were used as controls.

For the virus-infused mice, glucose therapy (Lei et al., Nat Genet 13: 203-209, 1996) was terminated immediately after infusion.

Glucose tolerance testing of mice consisted of fasting for 6 hours, prior to blood sampling, followed by intraperitoneal injection of a glucose solution at 2 mg/g body weight, and repeated blood sampling via the tail vein for 2 hours.

Phosphohydrolase and Microsomal G6P Uptake Assays

Microsome isolation, phosphohydrolase assays, enzyme histochemical analysis of G6Pase-α, and microsomal G6P uptake assays were performed as described previously (Yiu et al., Mol Ther 18:1076-1084, 2010; Lei et al., Nat Genet 13: 203-209, 1996).

Phenotype Analyses

Mice were first examined for hepatic nodules by ultrasound using the Vevo 2100 system (VisualSonics, Ontario, Canada) and blood samples were collected from the tail vein. Blood glucose, total cholesterol, and uric acid were analyzed using kits obtained from Thermo Electron (Louisville, Colo.); triglycerides, by a kit from Sigma Diagnostics (St Louis, Mo.); lactate, by a kit from Trinity Biotech (St. Louis, Mo.); and insulin, by an ultra-sensitive mouse insulin ELISA kit from Crystal Chem (Downers Grove, Ill.). Hepatic glycogen contents were measured as described previously (Yiu et al., Mol Ther 18:1076-1084, 2010). To determine hepatic triglyceride, glucose, and G6P contents, liver tissues were homogenized in RIPA buffer (50 mM Tris HCl, pH 8.0, 150 mM NaCl, 1% Triton X-100, 0.5% Na-deoxycholate, and 0.1% SDS) (Thermo Scientific, Rockford, Ill.), and triglycerides were measured using a kit from Sigma Diagnostics, glucose, by a kit from Thermo Electron, and G6P, by a kit from BioVision (Mountain View, Calif.).

For hematoxylin and eosin (H&E) and oil red O staining (Yiu et al., Mol Ther 18:1076-1084, 2010), liver sections were preserved in 10% neutral buffered formalin and sectioned at 4-10 microns thickness. The stained sections were visualized using the Axioskop2 plus microscope and the AxioVision 4.5 software (Carl Zeiss, Thornwood, N.Y.).

Quantitative Real-Time RT-PCR and Antibody Analysis

Total RNAs were isolated from liver tissues using the TRIzol™ Reagent (Invitrogen, Carlsbad, Calif.). The mRNA expression was quantified by real-time RT-PCR in an Applied Biosystems 7300 Real-Time PCR System using Applied Biosystems TaqMan probes (Foster City, Calif.). Data were analyzed using the Applied Biosystems SDS v1.3 software and normalized to β-actin RNA. Antibodies against human G6Pase-α were detected by Western-blot analysis as described previously (Yiu et al., Mol Ther 18:1076-1084, 2010).

Statistical Analysis

The unpaired t test was performed using the GraphPad Prism® Program, version 4 (San Diego, Calif.). Values were considered statistically significant at P<0.05.

Results

AAV-GPE Infusion Directs Long-Term Hepatic G6Pase-α Expression

Two- or four-week-old G6pc$^{-/-}$ mice (n=18) were infused with varying doses of AAV-GPE ($5 \times 10^{12}$ to $3 \times 10^{13}$ viral particles (vp)/kg) predicted to restore and maintain 3% to 100% of wild type hepatic G6Pase-α activity. One 15-week-old ($5 \times 10^{12}$ vp/kg) and one 30-week-old ($1 \times 10^{13}$ vp/kg) G6pc$^{-/-}$ mouse were also infused. The low survival rate of GSD-Ia mice under glucose therapy severely restricted the numbers of adult mice available to study (Lei et al., Nat Genet 13: 203-209, 1996). Metabolic and histological profiles of the 20 infused animals were monitored across 70-90 weeks and all measurements compared to those of their G6pc$^{+/+}$ and G6pc$^{+/-}$ littermates. The phenotype of both G6pc$^{+/+}$ and G6pc$^{+/-}$ mice are indistinguishable from wild type (Lei et al., Nat Genet 13: 203-209, 1996).

There were no premature deaths of the AAV-GPE-treated G6pc$^{-/-}$ mice. Hepatic G6Pase-α activity and glycogen content, were assessed in mice sacrificed after a 24 hour fast. The mean fasting hepatic G6Pase-α activity of 70- to 90-week-old wild type mice (n=20) was 185.8±12.7 nmol/mg/min (FIG. 2A). As planned, there was a range of hepatic G6Pase-α activities restored in the treated mice. Of the 20 AAV-GPE-treated G6pc$^{-/-}$ mice sacrificed at age 70 to 90 weeks, 6 mice had low levels (3% to 9% of wild type activity) of hepatic G6Pase-α activity and were designated AAV-L, 9 mice had medium levels (22% to 63% of wild type activity) of hepatic G6Pase-α activity, designated AAV-M, and 5 mice had high levels (81% to 128% of wild type activity) of hepatic G6Pase-α activity, designated AAV-H (FIG. 2A). Real-time RT-PCR analysis showed a linear relationship between hepatic G6Pase-α mRNA expression and G6Pase-α activity (FIG. 2B).

Enzyme histochemical analysis showed that G6Pase-α in wild type mice was distributed throughout the liver with significantly higher levels in proximity to blood vessels. There was no stainable G6Pase-α activity in the liver sections of untreated G6pc$^{-/-}$ mice. In AAV-GPE-treated G6pc$^{-/-}$ mice, G6Pase-α was also distributed throughout the liver but with foci, not related to blood vessels, containing markedly higher levels of enzymatic activity. The uneven distribution of hepatic G6Pase-α in the AAV-GPE-treated G6pc$^{-/-}$ mice suggests that a substantial proportion of hepatocytes harbored low or little G6Pase-α, including AAV-H livers expressing 81-128% of wild type G6Pase-α activity. Uniform hepatic G6Pase-α expression is not required for rescue of the GSD-Ia phenotype.

AAV-GPE Infusion Corrects Metabolic Abnormalities in GSD-Ia

GSD-Ia is characterized by hypoglycemia, hypercholesterolemia, hypertriglyceridemia, hyperuricemia, and lactic academia (Chou et al., *Nat Rev Endocrinol* 6:676-688, 2010). Blood glucose levels in AAV-H mice expressing wild type hepatic G6Pase-α activity were indistinguishable from those of the control littermates (FIG. 3A). AAV-M and AAV-L expressing 22-63% and 3-9% normal hepatic G6Pase-α activity, respectively also maintained a euglycemia (~100 mg/dl) state (Yoshizawa et al., *J Clin Invest* 119:2807-2817, 2009) but their blood glucose levels were consistently lower than the control littermates (FIG. 3A). All AAV-GPE-treated G6pc$^{-/-}$ mice exhibited normal serum profiles of cholesterol and triglyceride, while serum levels of uric acid and lactic acid in the treated G6pc$^{-/-}$ mice were lower than those in the control littermates (FIG. 3A).

The average body weights of female and male AAV-GPE-treated mice at age 70-90 weeks were 70% and 62%, respectively of their age- and sex-matched control mice (FIG. 3B). However, the average body lengths of the treated G6pc$^{-/-}$ mice were 90% of the controls (FIG. 3B). Consequently, body mass index (BMI) values (Bahary et al., *Proc Natl Acad Sci USA* 87:8642-8646, 1990) of AAV-GPE-treated G6pc$^{-/-}$ mice were significantly lower than those of the control littermates (FIG. 3B). While BMI values of both mouse groups signify normal growth (Bahary et al., *Proc Natl Acad Sci USA* 87:8642-8646, 1990), the AAV-GPE-treated G6pc$^{-/-}$ mice were considerably leaner. The liver weights in wild type mice were relatively constant (FIG. 3C). In AAV-GPE-infused mice, liver weights were inversely correlated to the hepatic G6Pase-α activity restored (FIG. 3C). When liver weights were expressed as percent of body weight, AAV-GPE-treated G6pc$^{-/-}$ mice had significantly higher values because of their lower body weights. However, when absolute liver weights were compared directly, there was no significant difference between AAV-M, AAV-H, and control littermates (FIG. 3C). AAV-L mice, however, continued exhibiting hepatomegaly. AAV-GPE delivers little or no transgene to the kidney (Yiu et al., *Mol Ther* 18:1076-1084, 2010). However, the infused mice expressing higher hepatic G6Pase-α activity had lower kidney weights, suggesting good hepatic metabolic control normalized nephromegaly.

Absence of Histological Abnormalities, Steatosis, or HCA in AAV-GPE-Infused G6pc$^{-/-}$ Livers To determine the presence of HCA nodules in AAV-GPE-treated G6pc$^{-/-}$ mice, ultrasound analysis was conducted, followed by extensive examination of the livers and histological analysis of liver biopsy samples, using 5 or more separate sections per liver. Ultrasound and morphological analyses detected no hepatic nodules in wild type (n=20) and AAV-GPE-transduced G6pc$^{-/-}$ (n=20) mice that lived to age 70-90 weeks. The AAV-GPE-treated G6pc$^{-/-}$ mice infused at age 2 or 4 weeks (n=18) exhibited no hepatic histological abnormalities except increased glycogen storage. The 84-week-old mouse infused at age 15 weeks, which expressed 6% of normal hepatic G6Pase-α activity, exhibited elevated glycogen storage and a few necrotic foci in one liver section. While most of the liver tissue sections of the 90-week-old mouse infused at age 30 weeks, which expressed 38% of normal hepatic G6Pase-α activity, exhibited no histological abnormalities, one liver section did have many necrotic foci. As necrotic foci are a characteristic hepatic pathology seen in untreated GSD-Ia mice age 6 weeks or older (Kim et al., *J Hepatol* 48: 479-485, 2008), it is quite likely that the necrotic foci had developed before initiation of gene therapy at age 15 or 30 weeks.

The livers of liver-specific G6pc-null mice were reported to develop HCA with marked steatosis (Mutel et al., *J Hepatol* 54:529-537, 2011). While a few wild type mice had increased hepatic fat storage, there was little or no fat storage in the livers of AAV-GPE-treated G6pc$^{-/-}$ mice. Moreover, hepatic triglyceride contents in AAV-GPE-treated G6pc$^{-/-}$ mice (n=20) were not statistically different from those in wild type mice. Oil red O staining confirmed that lipid contents in AAV-GPE-treated animals (n=20) were similar to that in the controls.

It has been well established that cyclooxygenase-2 (COX-2) is a marker that is over-expressed in many pre-malignant and malignant cancers, including HCC (Wu, *Cancer Treat Rev* 32:28-44, 2006). Quantitative RT-PCR analysis showed that similar levels of hepatic COX-2 message were expressed in AAV-GPE-treated G6pc$^{-/-}$ and control littermates.

AAV-GPE-Treated G6pc$^{-/-}$ Mice Exhibit Normal Fasting Glucose and Glucose Tolerance Profiles The mean blood glucose levels of wild type mice (n=20) before commencing fasting were 165.0±3.0 mg/dl (zero time) which decreased to 113.3±6.5 mg/dl after 24 hours of fasting (FIG. 4A). The fasting blood glucose profiles of AAV-L and AAV-M mice paralleled those of the control mice but blood glucose levels were consistently lower (FIG. 4A), while the fasting glucose profile of AAV-H mice was indistinguishable from that of the control mice. In sharp contrast, untreated G6pc$^{-/-}$ mice exhibited marked hypoglycemia within 60 to 75 minutes of fasting (FIG. 4B), a hallmark of GSD-Ia (Chou et al., *Nat Rev Endocrinol* 6:676-688, 2010). In summary, AAV-GPE-treated G6pc$^{-/-}$ mice no longer suffered from the fasting hypoglycemia characteristic of GSD-Ia (Chou et al., *Nat Rev Endocrinol* 6:676-688, 2010).

Blood glucose tolerance profiles in AAV-M and AAV-H mice were indistinguishable from those of wild-type littermates (FIG. 4C). In AAV-L mice, following intraperitoneal glucose injection, blood glucose levels declined at a faster rate than the wild type controls.

Reduced Fasting Blood Insulin Levels in AAV-GPE-Treated G6pc$^{-/-}$ Mice

Insulin signaling regulates hepatic glucose and lipid metabolism (Leavens and Birnbaum, *Crit Rev Biochem Mol Biol* 46:200-215, 2011). After 24 hours of fasting, blood insulin levels in 70-90-week-old wild type (n=20) and AAV-GPE-treated G6pc$^{-/-}$ mice (n=20) were 1.84±0.29 and 0.56±0.09 ng/ml, respectively (FIG. 5A). Both were within the normal range (de Luca et al., *J Clin Invest* 115:3484-

3493, 2005), although fasting blood insulin levels in the AAV-GPE-treated G6pc$^{-/-}$ mice were more close to the normal average values (de Luca et al., *J Clin Invest* 115: 3484-3493, 2005). While fasting blood insulin levels in AAV-GPE-treated G6pc$^{-/-}$ mice did not correlate with hepatic G6Pase-α restored, insulin levels in wild type and the treated G6pc$^{-/-}$ mice exhibited a linear relationship to their body weights (FIG. 5A).

The transcriptional effect of insulin is mediated by sterol regulatory element binding protein-1c (SREBP-1c) (Leavens and Birnbaum, *Crit Rev Biochem Mol Biol* 46:200-215, 2011). Quantitative RT-PCR analysis showed that similar levels of hepatic SREBP-1c transcripts were expressed in the 24-hour-fasted AAV-GPE-treated G6pc$^{-/-}$ and control mice (FIG. 5B). Glucokinase is a glucose sensor (Massa et al., *IUBMB Life* 63:1-6, 2011). Hepatic glucokinase activity decreases when blood insulin levels are low, as when fasting (Massa et al., *IUBMB Life* 63:1-6, 2011). As was seen with blood insulin, after 24 hours of fast, hepatic glucokinase transcripts in AAV-GPE-treated G6pc$^{-/-}$ mice were significantly lower than that in the control littermates (FIG. 5C). Interestingly, levels of hepatic glucokinase mRNA and fasting blood insulin exhibited a linear relationship in both wild-type and AAV-GPE-treated G6pc$^{-/-}$ mice (FIG. 5C).

Glucose Homeostasis in the Liver of AAV-GPE-Infused G6pc$^{-/-}$ Mice

During fasting, blood glucose homeostasis is maintained by endogenous glucose produced in the liver from hydrolysis of G6P by the G6PT/G6Pase-α complex in the terminal step of gluconeogenesis and glycogenolysis (Chou et al., *Nat Rev Endocrinol* 6:676-688, 2010). G6pc$^{-/-}$ mice, lacking a functional G6Pase-α, are incapable of producing endogenous glucose in the liver, kidney, or intestine. After 24 hours of fast, hepatic free glucose levels in wild type mice (n=20) were 389±17 nmol/mg protein and in AAV-L (n=6), AAV-M (n=9), and AAV-H (n=5) mice were 61%, 68% and 90%, respectively, of that in wild type mice. Intracellular G6P levels in the fasted AAV-L and AAV-M livers were 2.9- and 1.6-fold, respectively higher than wild type livers but intracellular G6P levels in the fasted AAV-H livers were statistically similar to that of wild type livers.

Hepatic G6P participates in several metabolic pathways, including glycogen synthesis, glycolysis, the pentose-phosphate pathway, in the cytoplasm and endogenous glucose production in the ER lumen. Hepatic expression of several key enzymes involved in the above mentioned pathways was examined in mice after a 24-hour fast. These included the cytosolic phosphoenolpyruvate carboxykinase (PEPCK-C) that catalyzes the first committed step in hepatic gluconeogenesis (Hanson and Reshef, *Biochimie* 85:1199-1205, 2003); fructose-1,6-bisphosphatase (FBPase-1) that converts fructose-1,6-bisphosphate to fructose-6-phosphate (Hers, *J Inherit Metab Dis* 13:395-410, 1990); phosphoglucomutase (PGMase) that catalyzes the reversible conversion of glucose-6-P and glucose-1-P in glycogenolysis and glycogen synthesis (Hers, *J Inherit Metab Dis* 13:395-410, 1990); phosphofructokianse-1 (PFK-1) that catalyzes the irreversible rate-limiting step in glycolysis by converting fructose-6-P to fructose-1,6-diphosphate (Hers, *J Inherit Metab Dis* 13:395-410, 1990); G6P dehydrogenase (G6PDH) that catalyzes the first reaction in the pentose-phosphate pathway by converting G6P to 6-phosphgluconolactone (Wamelink et al., *J Inherit Metab Dis* 31:703-717, 2008); and G6PT that transports cytoplasmic G6P into the ER lumen (Chou et al., *Nat Rev Endocrinol* 6:676-688, 2010).

Quantitative real-time RT-PCR analysis showed that in the fasted livers, PEPCK-C and PGMase transcripts were unchanged while FBPase-1 transcripts were increased in the AAV-GPE-treated G6pc$^{-/-}$ mice, compared to the controls. Both PFK-1 and G6PDH transcripts in AAL-L livers were increased although in AAV-M and AAV-H livers they were still statistically similar to that of wild type livers. Hepatic G6PT mRNA levels in the AAV-GPE-treated G6pc$^{-/-}$ mice were 2.2-fold higher than the wild-type controls, regardless of the levels of hepatic G6Pase-α activity restored. The G6PT-mediated hepatic microsomal G6P uptake activity is the rate-limiting in endogenous glucose production (Anion et al., *J Biol Chem* 251:6784-690, 1976), but is co-dependent upon G6Pase-α activity (Lei et al., *Nat Genet* 13: 203-209, 1996). Hepatic microsomes prepared from G6pc$^{-/-}$ mice, with an intact G6PT, exhibit markedly lower G6P uptake activity compared to wild type hepatic microsomes (Lei et al., *Nat Genet* 13: 203-209, 1996), which can be reversed if G6Pase-α activity is restored via gene transfer (Zingone et al., *J Biol Chem* 275:828-832, 2000). In AAV-L, AAV-M, and AAV-H livers, microsomal G6P uptake activities were 43%, 50%, and 72%, respectively of wild type activity, reflecting the increase in hepatic G6Pase-α activity (FIG. 2A) that paralleled hepatic free glucose levels.

Absence of Immune Response Against Human G6Pase-α

To determine whether a humoral response directed against human G6Pase-α is generated in the infused mice, Western blot analysis was performed using the sera obtained from the 70-90-week-old control and AAV-GPE-treated G6pc$^{-/-}$ mice. A monoclonal antibody against human G6Pase-α that also recognizes murine G6Pase-α (Yiu et al., *Mol Ther* 18:1076-1084, 2010) was used as a positive control. No antibodies directed against G6Pase-α were detected in any of the AAV-GPE-infused G6pc$^{-/-}$ or wild type control mice that lived to age 70 to 90 weeks.

Example 3

The Upstream Enhancer Elements of the G6PC Promoter are Critical for Optimal G6PC Expression in Glycogen Storage Disease Type Ia This example describes studies to further evaluate the efficacy of the AAV-GPE vector. AAV-GPE, which is a single-stranded vector comprising 2684 bp of the G6PC promoter/enhancer, was compared to AAV-miGPE, a double-stranded vector containing a 382 bp minimal G6PC promoter/enhancer. The results described in this example show that the AAV-GPE vector directed significantly higher levels of hepatic G6Pase-α expression, achieved greater reduction in hepatic glycogen accumulation, and led to a better toleration of fasting in GSD-Ia mice than the AAV-miGPE vector.

Materials and Methods

Infusion of G6pc−/− Mice with rAAV Vectors

All G6pc−/− mice were kept alive with glucose therapy (Lei et al., *Nat. Genet.* 13:203-209, 1996). The rAAV vectors were infused into 2-week-old G6pc−/− mice via the retro-orbital sinus. Age-matched G6pc+/+/G6pc+/− mice were used as controls. For rAAV vector-infused mice, glucose therapy was terminated immediately after infusion. All viral transductions were performed on 2-week-old G6pc−/− mice and the efficacy evaluated at age 12 weeks.

Phosphohydrolase Assays

Microsome isolation and phosphohydrolase assays were determined essentially as described previously (Lei et al., *Nat. Genet.* 13:203-209, 1996). For phosphohydrolase assays, reaction mixtures (100 µl) containing 50 mM cacodylate buffer, pH 6.5, 10 mM G6P and appropriate amounts of microsomal preparations were incubated at 30° C. for 10 minutes. Disrupted microsomal membranes were prepared by incubating intact membranes in 0.2% deoxycholate for 20 minutes at 0° C. Non-specific phosphatase activity was estimated by pre-incubating disrupted microsomal preparations at pH 5 for 10 minutes at 37° C., to inactivate the acid labile G6Pase-α.

Quantification of Vector DNA and mRNA

Total DNA from mouse tissues was isolated using the GenElute™ Mammalian Genomic DNA Miniprep Kits (Sigma-Aldrich, St Louis, Mo.) and total RNAs were isolated from mouse tissues using the TRIzol™ Reagent (Invitrogen, Carlsbad, Calif.). The vector genome numbers and mRNA expression were quantified by PCR and real-time RT-PCR, respectively in an Applied Biosystems 7300 Real-Time PCR System using Applied Biosystems TaqMan probes (Applied Biosystems, Foster City, Calif.). The vector genome numbers of human G6PC gene was normalized to mouse β-actin using TaqMan probe sets Hs00609178_m1 for G6PC and Mm00607939_s1 for β-actin. Plasmid DNA corresponding to 0.01 to 100 copies of human G6PC gene was used in a standard curve. To determine the vector genome copy number, the Ct values of sample were compared to the standard curve. G6PC mRNA expression was normalized to Rpl19 RNA using TaqMan® probe sets Hs00609178_m1 for G6PC and Mm02601633_g1 for Rpl19.

Phenotype Analyses

Blood glucose was analyzed using kits obtained from Thermo Electron (Louisville, Colo.). Hepatic glycogen and triglyceride contents were measured as described previously (see Examples 1 and 2, and Yiu et al., *Mol. Ther.* 18:1076-1084, 2010; Lee et al., *Hepatology* 56:1719-1729, 2012). To determine hepatic triglyceride, liver tissues were homogenized in RIPA buffer (50 mM Tris HCl, pH 8.0, 150 mM NaCl, 1% Triton X-100, 0.5% Na-deoxycholate, and 0.1% SDS) (Thermo Scientific, Rockford, Ill.), and triglycerides were measured using a kit from Sigma Diagnostics (St Louis, Mo.).

Glucose tolerance testing of mice consisted of fasting for 6 hours, prior to blood sampling, followed by intraperitoneal injection of a glucose solution at 2 mg/g body weight, and repeated blood sampling via the tail vein for 2 hours.

Statistical Analysis

The unpaired t test was performed using the GraphPad Prism® Program, version 4 (GraphPad Software Inc., San Diego, Calif.). Values were considered statistically significant at $p<0.05$.

Results

Hepatic G6Pase-α Expression in rAAV-GPE- or rAAV-miGPE-Treated G6pc−/− Mice

Studies were conducted to examine the efficacy of the rAAV-GPE (see Example 1 and Yiu et al., *Mol. Ther.* 18:1076-1084, 2010) and rAAV-miGPE (Koeberl et al., *Mol. Ther.* 16:665-672, 2008) vectors in treating G6pc−/− mice over 12-weeks. Each vector was used at two doses, $1\times10^{13}$ viral particles (vp)/kg (high dose) and $2\times10^{12}$ vp/kg (low dose) with 6 mice per group, at two different research centers. Similar results were obtained from both centers. While hepatic G6Pase-α activity in the transduced G6pc−/− mice represents the combined data from the two centers, other reported data are from a single study. Studies have shown that the efficiency and persistence of rAAV-mediated hepatic gene transfer are lower during early development because of the fast rate of hepatocellular proliferation associated with liver growth, which dilutes out the number of cells effectively infected with rAAV (Yiu et al., *Mol. Ther.* 18:1076-1084, 2010; Cunningham, *Mol. Ther.* 16:1081-1088, 2008). In this study, the rAAV vectors were administered to 2-week-old G6pc−/− mice when hepatocellular proliferation remains high. Consequently, hepatic G6Pase-α expression examined at age 12 weeks is significantly lower than that seen in adult mice infused with the same vector dosage. The best time of intervention in the human disease remains to be established.

Figure 6A:
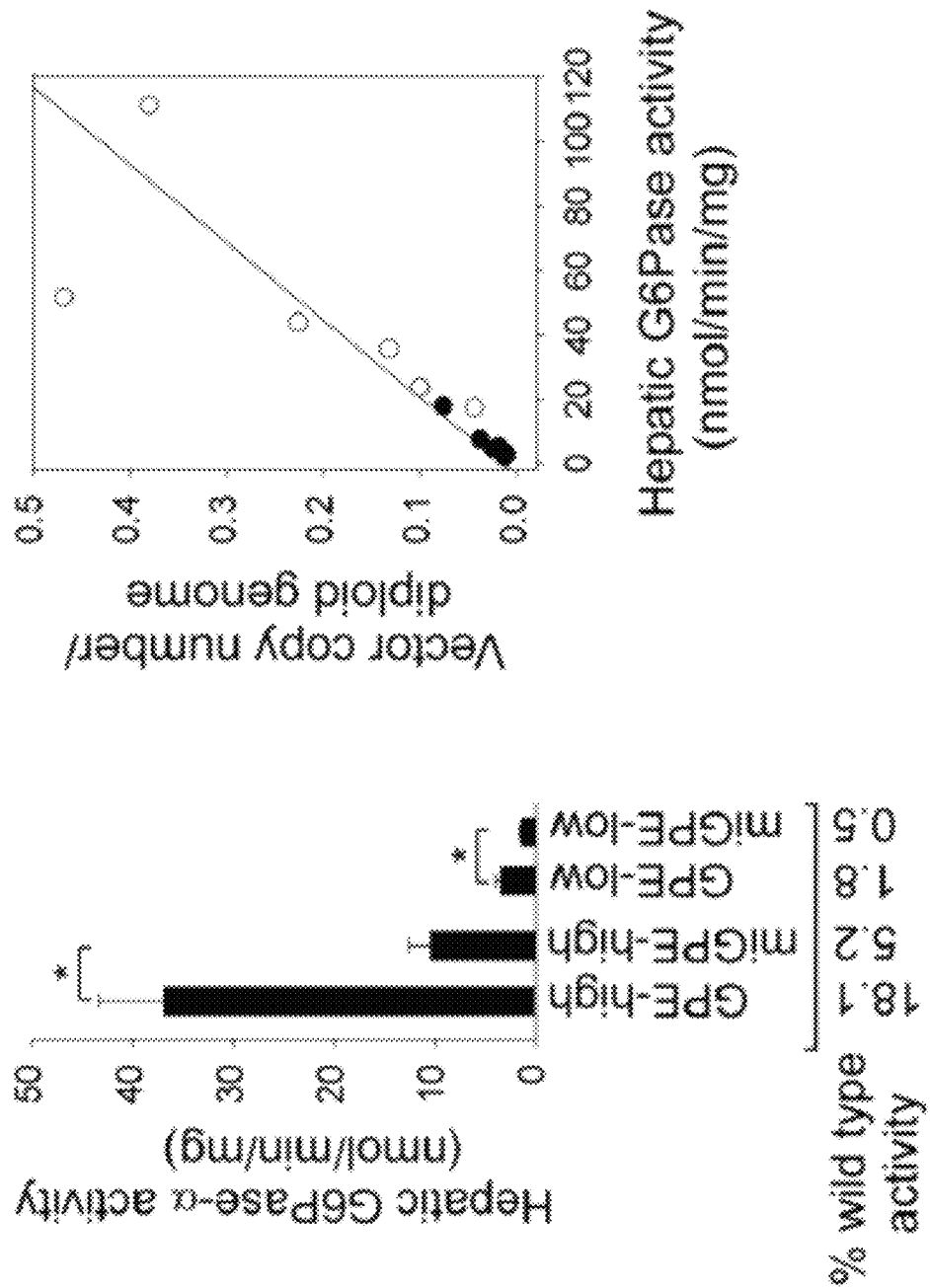
Figure 6D:
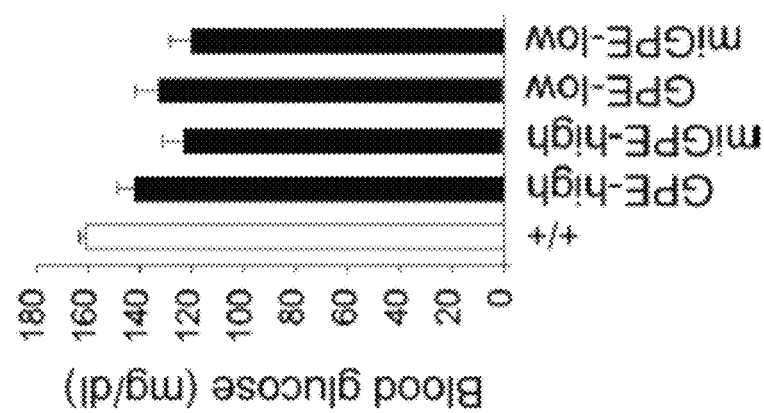

All treated G6pc−/− mice survived to age 12 weeks with no premature deaths at either center. In the liver of 12-week-old wild type mice, microsomal G6Pase-α activity was 203.5±10.3 nmol/min/mg (n=24). The combined data (n=12 per treatment), determined independently at the two centers, showed that at age 12 weeks, the high dose rAAV-GPE therapy reconstituted about 18% of wild type hepatic G6Pase-α activity which was 3.5-fold more activity than rAAV-miGPE, while the low dose rAAV-GPE therapy produced over 3.6 times more activity than rAAV-miGPE (FIG. 6A). The hepatic G6Pase-α activity increased linearly with hepatic vector genome copy number, and the copy numbers in rAAV-GPE-treated G6pc−/− mice (n=6) were significantly higher than the rAAV-miGPE-treated mice (n=6) (FIG. 6A).

Metabolic Profiles of rAAV-GPE- or rAAV-miGPE-Treated G6pc−/− Mice

Figure 6C:
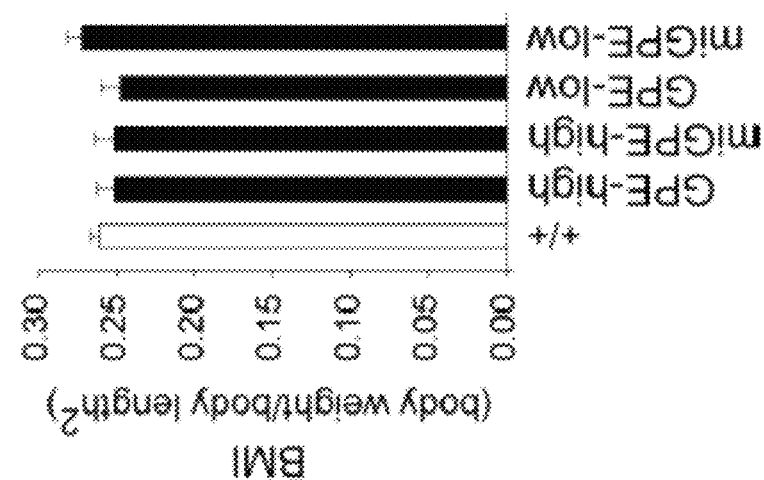
Figure 6B:
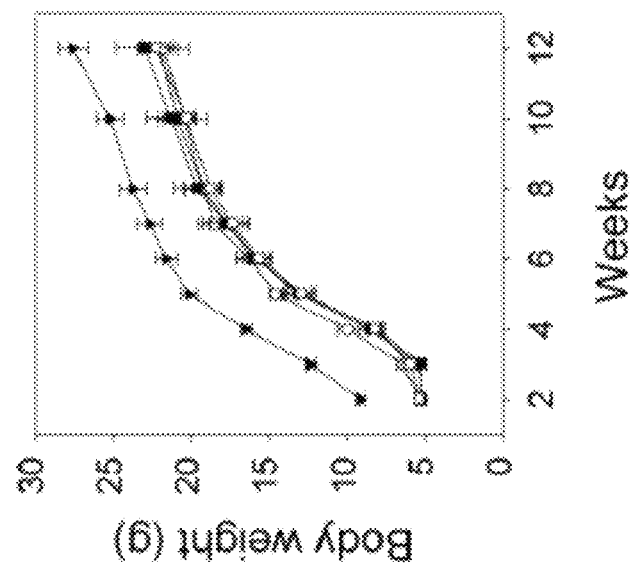

All rAAV-GPE- and rAAV-miGPE-treated G6pc−/− mice exhibited growth curves that paralleled their wild type littermates, albeit at lower weights (FIG. 6B). The body mass index (BMI) values of the treated mice were indistinguishable from those of wild type mice irrespective of the vector or dose level (FIG. 6C). All treated G6pc−/− mice had blood glucose levels consistently lower than wild type controls, but still above the lower end of the normal range (FIG. 6D), and none of the infused animals suffered from the frequent hypoglycemic seizures typical of GSD-Ia (Chou et al., *Curr. Mol. Med.* 2:121-143, 2002; Chou et al., *Nat. Rev. Endocrinol.* 6: 676-688, 2010; Lee et al., *Hepatology* 56:1719-1729, 2012).

The relative weight of the liver to the body, one measure of liver glycogen and/or neutral fat accumulation (Chou et al., *Curr. Mol. Med.* 2:121-143, 2002; Chou et al., *Nat. Rev. Endocrinol.* 6: 676-688, 2010), was higher in all 4 treated G6pc−/− mouse groups than wild type mice, although the high dose rAAV-GPE-treated mice were significantly closer to normal than the other groups (FIG. 7A). Consistent with this, glycogen contents in rAAV-GPE- and rAAV-miGPE-treated G6pc−/− mice were markedly higher than their wild type controls (FIG. 7B) with the higher vector doses lowering glycogen better than the lower vector doses, demonstrating that restoring higher hepatic G6Pase-α expression improves hepatomegaly. However, comparing just high dose therapies, the rAAV-miGPE-treated mice had 43% more glycogen than rAAV-GPE-treated mice. Despite the continued elevation in liver glycogen there were no histological abnormalities observed in the liver tissue sections of any of the rAAV-treated G6pc−/− mice at age 12 weeks. With the exception of rAAV-miGPE-treated mice at a low dose, hepatic triglyceride contents were not statistically different between wild type and the other 3 groups of rAAV-treated G6pc−/− mice (FIG. 7C).

Fasting Glucose and Glucose Tolerance Profiles in rAAV-GPE- or rAAV-miGPE-Treated G6pc−/− Mice For wild type mice (n=24), the mean blood glucose level before fasting was 172.2±2.6 mg/dl (zero time), which decreased to 134.6±3.8 mg/dl after 8 hours of fast (FIG. 8A).

The fasting blood glucose profiles of high dose therapy mice (n=6 per treatment) were significantly better than low dose therapy mice (n=6 per treatment), however, even at high dose, rAAV-GPE-treated mice sustained significantly higher glucose levels that stabilized to wild type levels 6 hours into the fast, while rAAV-miGPE-treated mice plateaued much lower at 60% of wild type levels (FIG. 8A). The high dose rAAV-GPE- and rAAV-miGPE-treated mice could also sustain a 24-hour fast but fasting blood glucose levels were significantly higher in rAAV-GPE-treated mice than rAAV-miGPE-treated mice (FIG. 8B). In summary, the rAAV-GPE-treated G6pc-/- mice were closer to wild type and more capable of tolerating fasting than the rAAV-miGPE-treated G6pc-/- mice.

Blood glucose tolerance profiles of the treated G6pc-/- mice (n=6 per treatment) were monitored following an intraperitoneal glucose injection. In general, the profiles paralleled those of the wild-type mice (FIG. 8C) with the high dose treated mice responding better than the low dose treated mice.

The bio-distribution of the human G6PC transgene in liver, kidney, intestine, brain, testis, and ovary in 12-week-old, high dose rAAV-GPE-treated G6pc-/- mice was analyzed by quantitative PCR (Table 1). In the transduced liver, vector genome copy numbers/µg DNA was 94,440±7,624 (or 0.51±0.04 vector copies/diploid genome). In the transduced kidney and intestine, the numbers were dramatically lower, averaging just 2.57% and 0.64% respectively of liver copy number, showing that the rAAV8 virus did not transduce kidney and intestine efficiently. The genome copy numbers/µg DNA in the brain and testis were even lower at 0.12% and 0.02%, respectively of liver copy number. Only background levels of human G6PC genomes were detected in the ovary.

The rAAV-GPE vector contains a tissue-specific promoter/enhancer element expressed primarily in the liver, proximal tubules in the kidney, and intestine (Chou et al., Curr. Mol. Med. 2:121-143, 2002; Chou et al., Nat. Rev. Endocrinol. 6: 676-688, 2010). Quantitative real-time RT-PCR analysis of human G6PC transcripts showed a correlation between genome copy number and gene expression (Table 3). In the liver, levels of human G6PC mRNA relative to the RpI19 transcript were 0.62740±0.04445. As expected from the genome copy analysis, the kidney expressed only 0.03% of the liver human G6PC mRNA, and only background levels of human G6PC mRNA were detected in the intestine, brain, testis, and ovary.

Example 4

Comparison of AAV Vectors with and without Stuffer Sequences

This example describes the finding that the stuffer nucleotide sequence flanking the intron in G6Pase-α-expressing AAV vectors is important for efficient hepatic transduction.

To evaluate the contribution of the stuffer sequence to transgene delivery and hepatic expression of G6Pase-α, plasmid UF11-K29-G6PC was constructed. UF11-K29-G6PC (SEQ ID NO: 2) differs from UF11-GPE-G6PC (SEQ ID NO: 1) in lacking the stuffer sequence around the intron. The G6PC promoter/enhancer (GPE) and the G6PC coding sequences are identical in each plasmid.

G6pc-/- mice were administered $1 \times 10^{13}$ vp/kg of either recombinant AAV-K29-G6PC or recombinant AAV-GPE-G6PC. The results indicated that AAV-K29-G6PC exhibited markedly reduced hepatic transducing efficiency in GSD-Ia mice, compared to AAV-GPE-G6PC. G6Pase activities in AAV-K29-G6PC- and AAV-GPE-G6PC-transduced liver were 7.3 and 33.0 nmol/min/mg, respectively. These results demonstrate that the stuffer sequence flanking the intron is important for efficient hepatic transduction.

Example 5

Generation of an AAV Vector Encoding Codon-Optimized G6PC

This example describes the construction and characterization of an AAV vector containing codon-optimized G6PC.

The UF11-GPE-co-G6PC plasmid (comprising codon-optimized G6PC; SEQ ID NO: 3) was derived from the UF11-GPE-G6PC plasmid (SEQ ID NO: 1), but the wild type G6Pase coding sequence in AAV-GPE-G6PC was replaced with a synthetic codon-optimized G6Pase (nucleotides 3368-4441 of SEQ ID NO: 3).

Transient in vitro expression assays showed that co-G6Pase exhibited enzyme activity 1.9-fold higher than wild type human G6Pase. In addition, two batches of recombinant AAV-GPE-co-G6PC have been evaluated for in vivo activity and compared to the activity of recombinant AAV-GPE-G6PC in GSD-Ia mice. The first batch of AAV-GPE-co-G6PC was 50% more efficient than AAV-GPE-G6PC in transducing the liver than AAV-GPE-G6PC. The

TABLE 3

Human G6PC genome distribution and mRNA expression in 12-week-old high dose rAAV-GPE-treated G6pc-/- mice

| Tissue | Human G6PC Copy number/µg genomic DNA | Human G6PC mRNA relative to RpI19 mRNA × $10^5$ |
|---|---|---|
| Wild type tissues, no transgene (n = 6) | 8 ± 2 | 8 ± 1 |
| Liver, -/-/rAAV-GPE (n = 6) | 94,440 ± 7,624 (100) | 62740 ± 4445 (100) |
| Kidney, -/-/rAAV-GPE (n = 6) | 2,429 ± 626 (2.57) | 22 ± 5 (0.033) |
| Intestine, -/-/rAAV-GPE (n = 6) | 601 ± 124 (0.64) | 9 ± 1 |
| Brain, -/-/rAAV-GPE (n = 6) | 121 ± 23 (0.12) | 8 ± 1 |
| Testis, -/-/rAAV-GPE (n = 6) | 25 ± 8 (0.02) | 9 ± 1 |
| Ovary, -/-/rAAV-GPE (n = 6) | 7 ± 2 | 9 ± 1 |

Data are means ± SEM.
The values of wild type tissues, which contain no transgene, were the mean ± SEM of liver, kidney, intestine, brain, testis, and ovary.
Numbers in parentheses are % of liver value.

second batch of AAV-GPE-co-G6PC was 2.5-fold more efficient in transducing the liver than recombinant AAV-GPE-G6PC.

These results demonstrate that codon-optimization of G6PC increases the liver transduction capacity of recombinant AAV expressing G6Pase-α.

Example 6

Evaluation of the Efficacy of a Recombinant AAV Vector Expressing Codon-Optimized Human G6Pase The example describes a study to compare the efficacy of gene delivery mediated by rAAV8-GPE-G6Pase and rAAV8-GPE-co-G6Pase in GSD-Ia mice.

The efficacy of gene delivery in GSD-Ia mice was compared using 2-3 independent batches of two AAV vectors: 1) rAAV8-GPE-G6Pase (a rAAV8 vector expressing human G6Pase-α directed by the ~3 kb human G6PC promoter/enhancer (GPE); and 2) rAAV8-GPE-co-G6Pase (a rAAV8 vector expressing a codon-optimized (co) human G6Pase-α directed by the GPE). The results in FIG. 11 show that hepatic G6Pase activities in both 4- and 12-week-old rAAV8-GPE-co-hG6Pase-treated GSD-Ia mice were 1.9-fold higher than the respective activities restored by the rAAV8-GPE-G6Pase vector.

All treated GSD-Ia mice exhibited normal serum profiles of cholesterol, triglyceride, uric acid and lactic acid and normal levels of hepatic fat. In rAAV-infused mice, liver weights were inversely correlated to the hepatic G6Pase activity restored. The rAAV-GPE-G6Pase-treated mice exhibited significantly more severe hepatomegaly as compared to the rAAV-GPE-co-G6Pase-treated mice (FIG. 12).

Functionally, at age 12 weeks, the rAAV8-GPE-co-G6Pase-treated GSD-Ia mice displayed normal glucose tolerance profiles (FIG. 13A) and maintained normoglycemia over a 24-hour fast (FIG. 13B).

Example 7

Treatment of Human GSD-Ia Using AAV-Based Gene Therapy

This example describes an exemplary method for the clinical use of AAV vectors encoding G6PC for the treatment of GSD-Ia.

A patient diagnosed with GSD-Ia is selected for treatment. Typically the patient is at least 18 years old and may or may not have had pre-exposure to immunomodulation. The patient is administered a therapeutically effective amount of a recombinant AAV expressing G6PC, such as AAV-GPE-G6PC or AAV-GPE-co-G6PC as disclosed herein. The recombinant AAV can be administered intravenously. An appropriate therapeutic dose can be selected by a medical practitioner. In some cases, the therapeutically effective dose is in the range of $1 \times 10^{11}$ to $1 \times 10^{14}$ viral particles (vp)/kg, such as about $1 \times 10^{12}$ vp/kg. In most instances, the patient is administered a single dose. In the absence of immunomodulation, the patient is likely to tolerate only a single infusion of rAAV. If the subject has had pre-exposure immunomodulation, two or more doses may be administered. The health of the subject can be monitored over time to determine the effectiveness of the treatment.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A recombinant nucleic acid molecule comprising a G6PC promoter/enhancer, a synthetic intron, and a G6PC coding region, wherein the nucleotide sequence of the recombinant nucleic acid molecule is at least 95% identical to nucleotides 182-4441 of SEQ ID NO: 1, and wherein the recombinant nucleic acid comprises at least one nucleotide substitution in the G6PC coding region that results in a coding change at residue 3, 54, 139, 196, 199, 242, 247, 292, 298, 301, 318, 324, 332, 347, 349, 350 or 353 of the human G6PC protein of SEQ ID NO: 4.

2. The recombinant nucleic acid molecule of claim 1, comprising a nucleotide sequence at least 99% identical to SEQ ID NO: 1.

3. The recombinant nucleic acid molecule of claim 1, further comprising 5' and 3' inverted terminal repeat (ITR) sequences, wherein the recombinant nucleic acid molecule comprises a nucleotide sequence at least 95% identical to nucleotides 17-4819 of SEQ ID NO: 1.

4. The recombinant nucleic acid molecule of claim 3, comprising a nucleotide sequence at least 99% identical to nucleotides 17-4819 of SEQ ID NO: 1.

5. The recombinant nucleic acid molecule of claim 1, comprising a nucleotide sequence at least 95% identical to SEQ ID NO: 1.

6. The recombinant nucleic acid molecule of claim 5, comprising a nucleotide sequence at least 99% identical to SEQ ID NO: 1.

7. The recombinant nucleic acid molecule of claim 1, comprising the nucleotide sequence of SEQ ID NO: 1 with the exception that the recombinant nucleic acid comprises a nucleotide substitution in the G6PC coding region that results in a coding change at residue 298 of the human G6PC protein of SEQ ID NO: 4.

8. A vector comprising the recombinant nucleic acid molecule of claim 1.

9. The vector of claim 8, wherein the vector is an adeno-associated virus (AAV) vector.

10. The vector of claim 9, wherein the AAV vector is an AAV serotype 8 (AAV8) vector.

11. An isolated host cell comprising vector of claim 8.

12. A recombinant AAV (rAAV) comprising the recombinant nucleic acid molecule of claim 1.

13. The rAAV of claim 12, wherein the rAAV is rAAV8.

14. A composition comprising the rAAV of claim 12 in a pharmaceutically acceptable carrier.

15. The composition of claim 14 formulated for intravenous administration.

16. A method of treating a subject diagnosed with a glycogen storage disease, comprising selecting a subject with glycogen storage disease type Ia (GSD-Ia) and administering to the subject a therapeutically effective amount of the rAAV of claim 12.

17. The method of claim 16, wherein the rAAV is administered intravenously.

18. The method of claim 16, wherein the rAAV is administered at a dose of about $1 \times 10^{11}$ to about $1 \times 10^{14}$ viral particles (vp)/kg.

19. The method of claim 16, wherein administering the rAAV comprises administration of a single dose of rAAV.

20. The method of claim 16, wherein administering the rAAV comprises administration of multiple doses of rAAV.

\* \* \* \* \*

SEQUENCE LISTING

```
<160> NUMBER OF SEQ ID NOS: 10

<210> SEQ ID NO 1
<211> LENGTH: 7671
<212> TYPE: DNA
<213> ORGANISM: Artificial Sequence
<220> FEATURE:
<223> OTHER INFORMATION: Synthetic construct (plasmid UF11-GPE-G6PC)
<220> FEATURE:
<221> NAME/KEY: misc_feature
<222> LOCATION: (17)..(163)
<223> OTHER INFORMATION: Inverted terminal repeat
<220> FEATURE:
<221> NAME/KEY: misc_feature
<222> LOCATION: (182)..(3045)
<223> OTHER INFORMATION: G6PC promoter/enhancer
<220> FEATURE:
<221> NAME/KEY: misc_feature
<222> LOCATION: (3051)..(3184)
<223> OTHER INFORMATION: Stuffer sequence
<220> FEATURE:
<221> NAME/KEY: misc_feature
<222> LOCATION: (3185)..(3321)
<223> OTHER INFORMATION: Intron
<220> FEATURE:
<221> NAME/KEY: misc_feature
<222> LOCATION: (3322)..(3367)
<223> OTHER INFORMATION: Stuffer sequence
<220> FEATURE:
<221> NAME/KEY: misc_feature
<222> LOCATION: (3368)..(4441)
<223> OTHER INFORMATION: G6PC coding sequence
```

```
<220> FEATURE:
<221> NAME/KEY: misc_feature
<222> LOCATION: (4674)..(4819)
<223> OTHER INFORMATION: Inverted terminal repeat

<400> SEQUENCE: 1
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctagatctg aattcggtac     180
ccctttgaga atccacggtg tctcgatgca gtcagctttc taacaagctg gggcctcacc     240
tgttttccca cggataaaaa cgtgctggag gaagcagaaa ggggctggca ggtggaaaga     300
tgaggaccag ctcatcgtct catgactatg aggttgctct gatccagagg gtcccctgc     360 ctggtggccc accgccagga agactcccac tgtccctgga tgcccagagt gggatgtcaa     420
ctccatcact tatcaactcc ttatccatag gggtattctt cctgaggcgt ctcagaaaac     480
agggccctcc ccatatgctg accacataat agaaccctc ccaactcaga gcccctggct     540
gctagctgcc ctggcatgac ccagacagtg gcctttgtat atgttttag actcaccttg     600 actcacctct gaccatagaa actctcatcc cagaggtcac tgcaatagtt actccacaac     660
agaggcttat ctgggtagag ggaggctccc tacctatggc ccagcagccc tgacagtgca     720
gatcacatat accccacgcc ccagcactgc ctgccacgca tgggcttact ttacacccac     780
ccacagtcac caacacatta cctgctctcc aaggttaggc gtggcaggag aagtttgctt     840
ggaccagcag aaaccatgca gtcaaggaca actggagtca gcatgggctg ggtgcgagcc     900
cttggtgggg tggggaggag actccaggtc atacctcctg gaggatgttt taatcatttc     960
cagcatggaa tgctgtcaac ttttgccaca gattcattag ctctgagttt cttttttctg    1020
tccccagcta ccccttacat gtcaatatgg acttaatgat gggaaattca ggcaagtttt    1080
taaacatttt attccccctg gctcttatcc tcaaaaaatg catgaatttg gaggcagtgg    1140
ctcatgcctg taatcccaat gctttgctag gttgaggcgg gaggatcact tgaagccagg    1200
aatttgagac cagcctgggc cgcatagtga gaccccgttt ctacaaaaat aaataaataa    1260
ataataaata atagtgatat gaagcatgat taaatagccc tattttttaa aatgcatgag    1320
ttcgttacct gattcattcc ctggttcctt tcacagtcct ccgtgaccca agtgttaggg    1380
ttttggtctc tctactattt gtaggctgat atatagtata cacacacaca cacacacaca    1440
tatacacaca cacagtgtat cttgagcttt cttttgtata tctacacaca tatgtataag    1500
aaagctcaag atatagaagc ccttttttcaa aaataactga aagtttcaaa ctctttaagt    1560
ctccagttac cattttgctg gtattcttat ttggaaccat acattcatca tattgttgca    1620
cagtaagact atacattcat tattttgctt aaacgtatga gttaaaacac ttggccaggc    1680
atggtggttc acacctgtaa tcccagagct ttgggaagcc aagactggca gatctcttga    1740
gctcaggaat tcaagaccag cctgggcaac atggaaaaac cccatctcta caaaagatag    1800
aaaaattagc caggcatggt ggcgtgtgcc tgtggtccca gctactcagg aggctgaggt    1860
gggaggatca cattagccca ggaggttgag gctgcagtga gccgtgatta tgccactgca    1920
ctccagcctg ggagacagag tgagaccctg tttcaaaaaa aagagagaga aaatttaaaa    1980 agaaaacaa caccaagggc tgtaacttta aggtcattaa atgaattaat cactgcattc    2040
aaaaacgatt actttctggc cctaagagac atgaggccaa taccaggaag ggggttgatc    2100
tcccaaacca gaggcagacc ctagactcta atacagttaa ggaaagacca gcaagatgat    2160
```

```
agtccccaat acaatagaag ttactatatt ttatttgttg ttttcttttt gttttgtttt    2220
gttttgtttt gttttgtttt agagactggg gtcttgctcg attgcccagg ctgtagtgca    2280
gcggtgggac aatagctcac tgcagactcc aactcctggg ctcaagcaat cctcctgcct    2340
cagcctcctg aatagctggg actacaaggg tacaccatca cacaccaa aacaatttttt    2400
taaatttttg tgtagaaacg agggtcttgc tttgttgccc aggctggtct ccaactcctg    2460
gcttcaaggg atcctcccac ctcagcctcc caaattgctg ggattacagg tgtgagccac    2520
cacaaccagc cagaacttta ctaattttaa aattaagaac ttaaaacttg aatagctaga    2580
gcaccaagat ttttctttgt ccccaaataa gtgcagttgc aggcatagaa aatctgacat    2640
cttttgcaaga atcatcgtgg atgtagactc tgtcctgtgt ctctggcctg gtttcgggga    2700
ccaggagggc agaccttgc actgccaaga agcatgccaa agttaatcat tggccctgct    2760
gagtacatgg ccgatcaggc tgtttttgtg tgcctgttttt tctattttac gtaaatcacc    2820
ctgaacatgt ttgcatcaac ctactggtga tgcacctttg atcaatacat tttagacaaa    2880
cgtggttttt gagtccaaag atcagggctg ggttgacctg aatactggat acagggcata    2940
taaaacaggg gcaaggcaca gactcatagc agagcaatca ccaccaagcc tggaataact    3000
gcaagggctc tgctgacatc ttcctgaggt gccaaggaaa tgaggtctag agaagcttta    3060
ttgcggtagt ttatcacagt taaattgcta acgcagtcag tgcttctgac acaacagtct    3120
cgaacttaag ctgcagtgac tctcttaagg tagccttgca gaagttggtc gtgaggcact    3180
gggcaggtaa gtatcaaggt tacaagacag gtttaaggag accaatagaa actgggcttg    3240
tcgagacaga gaagactctt gcgtttctga taggcaccta ttggtcttac tgacatccac    3300
tttgcctttc tctccacagg tgtccactcc cagttcaatt acagctctta aggccctgca    3360
ggccaccatg gaggaaggaa tgaatgttct ccatgacttt gggatccagt caacacatta    3420
cctccaggtg aattaccaag actcccagga ctggttcatc ttggtgtccg tgatcgcaga    3480
cctcaggaat gccttctacg tcctcttccc catctggttc catcttcagg aagctgtggg    3540
cattaaactc ctttgggtag ctgtgattgg agactggctc aacctcgtct ttaagtggat    3600
tctctttgga cagcgtccat actggtgggt tttggatact gactactaca gcaacacttc    3660
cgtgcccctg ataaagcagt tccctgtaac ctgtgagact ggaccaggga gcccctctgg    3720
ccatgccatg gcacagcag gtgtatacta cgtgatggtc acatctactc tttccatctt    3780
tcagggaaag ataaagccga cctacagatt tcggtgcttg aatgtcattt tgtggttggg    3840
attctgggct gtgcagctga atgtctgtct gtcacgaatc taccttgctg ctcattttcc    3900
tcatcaagtt gttgctggag tcctgtcagg cattgctgtt gcagaaactt tcagccacat    3960
ccacagcatc tataatgcca gcctcaagaa atattttctc attaccttct tcctgttcag    4020
cttcgccatc ggatttttatc tgctgctcaa gggactgggt gtagacctcc tgtggactct    4080
ggagaaagcc cagaggtggt gcgagcagcc agaatgggtc acattgaca ccacacccctt    4140
tgccagcctc ctcaagaacc tgggcacgct ctttggcctg ggctggctc tcaactccag    4200
catgtacagg gagagctgca agggaaaact cagcaagtgg ctcccattcc gcctcagctc    4260
tattgtagcc tccctcgtcc tcctgcacgt ctttgactcc ttgaaacccc catcccaagt    4320
cgagctggtc ttctacgtct tgtccttctg caagagtgcg gtagtgcccc tggcatccgt    4380
cagtgtcatc ccctactgcc tcgcccaggt cctgggccag ccgcacaaga agtcgttgta    4440
agcggccgcg gggatccaga catgataaga tacattgatg agtttggaca aaccacaact    4500
agaatgcagt gaaaaaaatg ctttatttgt gaaatttgtg atgctattgc tttatttgta    4560
```

```
accattataa gctgcaataa acaagttaac aacaacaatt gcattcattt tatgtttcag    4620 gttcagggggg aggtgtggga ggttttttag tcgaccatgc tggggagaga tctaggaacc   4680
cctagtgatg gagttggcca ctccctctct gcgcgctcgc tcgctcactg aggccgcccg    4740
ggcaaagccc gggcgtcggg cgacctttgg tcgcccggcc tcagtgagcg agcgagcgcg    4800
cagagaggga gtggccaacc ccccccccc ccccctgca gccctgcatt aatgaatcgg      4860
ccaacgcgcg gggagaggcg gtttgcgtat gggcgctct tccgcttcct cgctcactga     4920
ctcgctgcgc tcggtcgttc ggctgcggcg agcggtatca gctcactcaa aggcggtaat   4980
acggttatcc acagaatcag gggataacgc aggaaagaac atgtgagcaa aaggccagca   5040
aaaggccagg aaccgtaaaa aggccgcgtt gctggcgttt ttccataggc tccgcccccc   5100
tgacgagcat cacaaaaatc gacgctcaag tcagaggtgg cgaaacccga caggactata   5160
aagataccag gcgtttcccc ctggaagctc cctcgtgcgc tctcctgttc cgaccctgcc   5220
gcttaccgga tacctgtccg cctttctccc ttcgggaagc gtggcgcttt ctcaatgctc   5280
acgctgtagg tatctcagtt cggtgtaggt cgttcgctcc aagctgggct gtgtgcacga   5340
accccccgtt cagcccgacc gctgcgcctt atccggtaac tatcgtcttg agtccaaccc   5400
ggtaagacac gacttatcgc cactggcagc agccactggt aacaggatta gcagagcgag   5460
gtatgtaggc ggtgctacag agttcttgaa gtggtggcct aactacggct acactagaag   5520
gacagtattt ggtatctgcg ctctgctgaa gccagttacc ttcggaaaaa gagttggtag   5580
ctcttgatcc ggcaaacaaa ccaccgctgg tagcggtggt ttttttgttt gcaagcagca   5640
gattacgcgc agaaaaaaag gatctcaaga agatcctttg atcttttcta cggggtctga   5700
cgctcagtgg aacgaaaact cacgttaagg gattttggtc atgagattat caaaaaggat   5760
cttcacctag atccttttaa attaaaaatg aagttttaaa tcaatctaaa gtatatatga   5820
gtaaacttgg tctgacagtt accaatgctt aatcagtgag gcacctatct cagcgatctg   5880
tctatttcgt tcatccatag ttgcctgact ccccgtcgtg tagataacta cgatacggga   5940
gggcttacca tctggcccca gtgctgcaat gataccgcga gacccacgct caccggctcc   6000
agatttatca gcaataaacc agccagccgg aagggccgag cgcagaagtg gtcctgcaac   6060
tttatccgcc tccatccagt ctattaattg ttgccgggaa gctagagtaa gtagttcgcc   6120
agttaatagt ttgcgcaacg ttgttgccat tgctacaggc atcgtggtgt cacgctcgtc   6180
gtttggtatg gcttcattca gctccggttc ccaacgatca aggcgagtta catgatcccc   6240
catgttgtgc aaaaaagcgg ttagctcctt cggtcctccg atcgttgtca gaagtaagtt   6300
ggccgcagtg ttatcactca tggttatggc agcactgcat aattctctta ctgtcatgcc   6360
atccgtaaga tgcttttctg tgactggtga gtactcaacc aagtcattct gagaatagtg   6420
tatgcggcga ccgagttgct cttgcccggc gtcaatacgg ataataccg cgccacatag    6480 cagaacttta aaagtgctca tcattggaaa acgttcttcg gggcgaaaac tctcaaggat   6540
cttaccgctg ttgagatcca gttcgatgta acccactcgt gcacccaact gatcttcagc   6600
atcttttact ttcaccagcg tttctgggtg agcaaaaaca ggaaggcaaa atgccgcaaa   6660
aaagggaata agggcgacac ggaaatgttg aatactcata ctcttccttt ttcaatatta   6720
ttgaagcatt tatcagggtt attgtctcat gagcggatac atatttgaat gtatttagaa   6780
aaataaacaa atagggggttc cgcgcacatt tccccgaaaa gtgccacctg acgtctaaga   6840
aaccattatt atcatgacat taacctataa aaataggcgt atcacgaggc cctttcgtct   6900
```

| | |
|---|---|
| cgcgcgtttc ggtgatgacg gtgaaaacct ctgacacatg cagctcccgg agacggtcac | 6960 |
| agcttgtctg taagcggatg ccgggagcag acaagcccgt cagggcgcgt cagcgggtgt | 7020 |
| tggcgggtgt cggggctggc ttaactatgc ggcatcagag cagattgtac tgagagtgca | 7080 |
| ccatatgcgg tgtgaaatac cgcacagatg cgtaaggaga aaataccgca tcaggaaatt | 7140 |
| gtaaacgtta atattttgtt aaaattcgcg ttaaattttt gttaaatcag ctcattttttt | 7200 |
| aaccaatagg ccgaaatcgg caaaatccct tataaatcaa agaatagac cgagataggg | 7260 |
| ttgagtgttg ttccagtttg gaacaagagt ccactattaa agaacgtgga ctccaacgtc | 7320 |
| aaagggcgaa aaaccgtcta tcagggcgat ggcccactac gtgaaccatc accctaatca | 7380 |
| agttttttgg ggtcgaggtg ccgtaaagca ctaaatcgga accctaaagg gagcccccga | 7440 |
| tttagagctt gacggggaaa gccggcgaac gtggcgagaa aggaagggaa gaaagcgaaa | 7500 |
| ggagcgggcg ctagggcgct ggcaagtgta gcggtcacgc tgcgcgtaac caccacaccc | 7560 |
| gccgcgctta atgcgccgct acagggcgcg tcgcgccatt cgccattcag gctacgcaac | 7620 |
| tgttgggaag ggcgatcggt gcgggcctct tcgctattac gccaggctgc a | 7671 |

```
<210> SEQ ID NO 2
<211> LENGTH: 7505
<212> TYPE: DNA
<213> ORGANISM: Artificial Sequence
<220> FEATURE:
<223> OTHER INFORMATION: Synthetic construct (plasmid UF11-K29-G6PC)
<220> FEATURE:
<221> NAME/KEY: misc_feature
<222> LOCATION: (17)..(163)
<223> OTHER INFORMATION: Inverted terminal repeat
<220> FEATURE:
<221> NAME/KEY: misc_feature
<222> LOCATION: (182)..(3045)
<223> OTHER INFORMATION: G6PC promoter/enhancer
<220> FEATURE:
<221> NAME/KEY: misc_feature
<222> LOCATION: (3052)..(3188)
<223> OTHER INFORMATION: Intron
<220> FEATURE:
<221> NAME/KEY: misc_feature
<222> LOCATION: (3202)..(4275)
<223> OTHER INFORMATION: G6PC coding sequence
<220> FEATURE:
<221> NAME/KEY: misc_feature
<222> LOCATION: (4508)..(4653)
<223> OTHER INFORMATION: Inverted terminal repeat
```

<400> SEQUENCE: 2

| | |
|---|---|
| gggggggggg ggggggggtt ggccactccc tctctgcgcg ctcgctcgct cactgaggcc | 60 |
| gggcgaccaa aggtcgcccg acgcccgggc tttgcccggg cggcctcagt gagcgagcga | 120 |
| gcgcgcagag agggagtggc caactccatc actaggggtt cctagatctg aattcggtac | 180 |
| cccttttgaga atccacggtg tctcgatgca gtcagctttc taacaagctg gggcctcacc | 240 |
| tgttttccca cggataaaaa cgtgctggag gaagcagaaa ggggctggca ggtgaaaga | 300 |
| tgaggaccag ctcatcgtct catgactatg aggttgctct gatccagagg gtcccctgc | 360 |
| ctggtggccc accgccagga agactcccac tgtccctgga tgcccagagt gggatgtcaa | 420 |
| ctccatcact tatcaactcc ttatccatag gggtattctt cctgaggcgt tcagaaaac | 480 |
| agggccctcc ccatatgctg accacataat agaaccctc ccaactcaga gaccctggct | 540 |
| gctagctgcc ctggcatgac ccagacagtg gcctttgtat atgttttag actcaccttg | 600 |
| actcacctct gaccatagaa actctcatcc cagaggtcac tgcaatagtt actccacaac | 660 |
| agaggcttat ctgggtagag ggaggctccc tacctatggc ccagcagccc tgacagtgca | 720 |

```
gatcacatat accccacgcc ccagcactgc ctgccacgca tgggcttact ttacacccac      780
ccacagtcac caacacatta cctgctctcc aaggttaggc gtggcaggag aagtttgctt      840
ggaccagcag aaaccatgca gtcaaggaca actggagtca gcatgggctg ggtgcgagcc      900
cttggtgggg tggggaggag actccaggtc atacctcctg gaggatgttt taatcatttc      960
cagcatggaa tgctgtcaac ttttgccaca gattcattag ctctgagttt ctttttctg     1020 tccccagcta cccccttacat gtcaatatgg acttaatgat gggaaattca ggcaagtttt    1080
taaacatttt attccccctg gctcttatcc tcaaaaaatg catgaatttg gaggcagtgg     1140
ctcatgcctg taatcccaat gctttgctag gttgaggcgg gaggatcact tgaagccagg     1200
aatttgagac cagcctgggc cgcatagtga ccccgtttc tacaaaaat aaataaataa      1260 ataataaata atagtgatat gaagcatgat taaatagccc tattttttaa aatgcatgag     1320
ttcgttacct gattcattcc ctggttcctt tcacagtcct ccgtgaccca agtgttaggg     1380
ttttggtctc tctactattt gtaggctgat atatagtata cacacacaca cacacacaca    1440
tatacacaca cacagtgtat cttgagcttt cttttgtata tctacacaca tatgtataag    1500
aaagctcaag atatagaagc ccttttttcaa aaataactga aagtttcaaa ctctttaagt    1560
ctccagttac cattttgctg gtattcttat ttggaaccat acattcatca tattgttgca     1620
cagtaagact atacattcat tattttgctt aaacgtatga gttaaaacac ttggccaggc     1680
atggtggttc acacctgtaa tcccagagct ttgggaagcc aagactggca gatctcttga     1740
gctcaggaat tcaagaccag cctgggcaac atggaaaaac cccatctcta caaaagatag     1800
aaaaattagc caggcatggt ggcgtgtgcc tgtggtccca gctactcagg aggctgaggt     1860
gggaggatca cattagccca ggaggttgag gctgcagtga gccgtgatta tgccactgca    1920
ctccagcctg ggagacagag tgagaccctg tttcaaaaaa aagagagaga aaatttaaaa    1980
aagaaaacaa caccaagggc tgtaaacttta aggtcattaa atgaattaat cactgcattc    2040
aaaaacgatt actttctggc cctaagagac atgaggccaa taccaggaag ggggttgatc     2100
tcccaaacca gaggcagacc ctagactcta atacagttaa ggaaagacca gcaagatgat    2160
agtccccaat acaatagaag ttactatatt ttatttgttg ttttttcttt gttttgtttt    2220
gttttgtttt gttttgtttt agagactggg tcttgctcg attgcccagg ctgtagtgca    2280
gcggtgggac aatagctcac tgcagactcc aactcctggg ctcaagcaat cctcctgcct    2340
cagcctcctg aatagctggg actacaaggg tacaccatca cacacaccaa acaattttt    2400 taaattttg tgtagaaacg agggtcttgc tttgttgccc aggctggtct ccaactcctg     2460
gcttcaaggg atcctcccac ctcagcctcc caaattgctg ggattacagg tgtgagccac    2520
cacaaccagc cagaactta ctaattttaa aattaagaac ttaaaacttg aatagctaga    2580
gcaccaagat ttttctttgt ccccaaataa gtgcagttgc aggcatagaa aatctgacat    2640
ctttgcaaga atcatcgtgg atgtagactc tgtcctgtgt ctctggcctg gtttcgggga    2700
ccaggagggc agaccctttgc actgccaaga agcatgccaa agttaatcat tggccctgct    2760
gagtacatgg ccgatcaggc tgttttttgtg tgcctgtttt tctattttac gtaaatcacc    2820
ctgaacatgt ttgcatcaac ctactggtga tgcacctttg atcaatacat tttagacaaa    2880
cgtggttttt gagtccaaag atcagggctg ggttgacctg aatactggat acagggcata    2940
taaaacaggg gcaaggcaca gactcatagc agagcaatca ccaccaagcc tggaataact    3000
gcaagggctc tgctgacatc ttcctgaggt gccaaggaaa tgaggtctag taggtaagta    3060
```

```
tcaaggttac aagacaggtt taaggagacc aatagaaact gggcttgtcg agacagagaa    3120
gactcttgcg tttctgatag gcacctattg gtcttactga catccacttt gcctttctct    3180
ccacaggtcc tgcaggccac catggaggaa ggaatgaatg ttctccatga ctttgggatc    3240
cagtcaacac attacctcca ggtgaattac caagactccc aggactggtt catcttggtg    3300
tccgtgatcg cagacctcag gaatgccttc tacgtcctct tccccatctg gttccatctt    3360
caggaagctg tgggcattaa actcctttgg gtagctgtga ttggagactg gctcaacctc    3420
gtctttaagt ggattctctt tggacagcgt ccatactggt gggttttgga tactgactac    3480
tacagcaaca cttccgtgcc cctgataaag cagttccctg taacctgtga gactggacca    3540
gggagcccct ctggccatgc catgggcaca gcaggtgtat actacgtgat ggtcacatct    3600
actctttcca tctttcaggg aaagataaag ccgacctaca gatttcggtg cttgaatgtc    3660
attttgtggt tgggattctg ggctgtgcag ctgaatgtct gtctgtcacg aatctacctt    3720
gctgctcatt ttcctcatca agttgttgct ggagtcctgt caggcattgc tgttgcagaa    3780
actttcagcc acatccacag catctataat gccagcctca gaaatatttt tctcattacc    3840
ttcttcctgt tcagcttcgc catcggattt tatctgctgc tcaagggact gggtgtagac    3900
ctcctgtgga ctctggagaa agcccagagg tggtgcgagc agccagaatg ggtccacatt    3960
gacaccacac cctttgccag cctcctcaag aacctgggca cgctctttgg cctggggctg    4020
gctctcaact ccagcatgta cagggagagc tgcaagggga aactcagcaa gtggctccca    4080
ttccgcctca gctctattgt agcctccctc gtcctcctgc acgtctttga ctccttgaaa    4140
cccccatccc aagtcgagct ggtcttctac gtcttgtcct tctgcaagag tgcggtagtg    4200
cccctggcat ccgtcagtgt catccctac tgcctcgccc aggtcctggg ccagccgcac    4260
aagaagtcgt tgtaagcggc cgcggggatc cagacatgat aagatacatt gatgagtttg    4320
gacaaaccac aactagaatg cagtgaaaaa aatgctttat ttgtgaaatt tgtgatgcta    4380
ttgctttatt tgtaaccatt ataagctgca ataaacaagt taacaacaac aattgcattc    4440
attttatgtt tcaggttcag gggaggtgt gggaggtttt ttagtcgacc atgctgggga    4500
gagatctagg aaccctagt gatggagttg gccactccct ctctgcgcgc tcgctcgctc    4560
actgaggccg cccgggcaaa gcccgggcgt cgggcgacct ttggtcgccc ggcctcagtg    4620
agcgagcgag cgcgcagaga gggagtggcc aaccccccc ccccccccc tgcagccctg    4680 cattaatgaa tcggccaacg cgcggggaga ggcggtttgc gtattgggcg ctcttccgct    4740
tcctcgctca ctgactcgct gcgctcggtc gttcggctgc ggcgagcggt atcagctcac    4800
tcaaaggcgg taatacggtt atccacagaa tcaggggata acgcaggaaa gaacatgtga    4860
gcaaaaggcc agcaaaaggc caggaaccgt aaaaaggccg cgttgctggc gttttttccat    4920 aggctccgcc ccctgacga gcatcacaaa aatcgacgct caagtcagag gtggcgaaac    4980
ccgacaggac tataaagata ccaggcgttt cccctggaa gctccctcgt gcgctctcct    5040
gttccgaccc tgccgcttac cggatacctg tccgcctttc tcccttcggg aagcgtggcg    5100
ctttctcaat gctcacgctg taggtatctc agttcggtgt aggtcgttcg ctccaagctg    5160
ggctgtgtgc acgaaccccc cgttcagccc gaccgctgcg ccttatccgg taactatcgt    5220
cttgagtcca acccggtaag acacgactta tcgccactgg cagcagccac tggtaacagg    5280
attagcagag cgaggtatgt aggcggtgct acagagttct tgaagtggtg gcctaactac    5340
ggctacacta gaaggacagt atttggtatc tgcgctctgc tgaagccagt taccttcgga    5400
aaaagagttg gtagctcttg atccggcaaa caaaccaccg ctggtagcgg tggtttttttt    5460
```

```
gtttgcaagc agcagattac gcgcagaaaa aaaggatctc aagaagatcc tttgatcttt    5520
tctacggggt ctgacgctca gtggaacgaa aactcacgtt aagggatttt ggtcatgaga    5580
ttatcaaaaa ggatcttcac ctagatcctt taaattaaa aatgaagttt taaatcaatc    5640
taaagtatat atgagtaaac ttggtctgac agttaccaat gcttaatcag tgaggcacct    5700
atctcagcga tctgtctatt tcgttcatcc atagttgcct gactccccgt cgtgtagata    5760
actacgatac gggagggctt accatctggc cccagtgctg caatgatacc gcgagaccca    5820
cgctcaccgg ctccagattt atcagcaata accagccag ccggaagggc cgagcgcaga    5880
agtggtcctg caactttatc cgcctccatc cagtctatta attgttgccg ggaagctaga    5940
gtaagtagtt cgccagttaa tagtttgcgc aacgttgttg ccattgctac aggcatcgtg    6000
gtgtcacgct cgtcgtttgg tatggcttca ttcagctccg gttcccaacg atcaaggcga    6060
gttacatgat cccccatgtt gtgcaaaaaa gcggttagct ccttcggtcc tccgatcgtt    6120
gtcagaagta agttggccgc agtgttatca ctcatggtta tggcagcact gcataattct    6180
cttactgtca tgccatccgt aagatgcttt tctgtgactg gtgagtactc aaccaagtca    6240
ttctgagaat agtgtatgcg gcgaccgagt tgctcttgcc cggcgtcaat acgggataat    6300
accgcgccac atagcagaac tttaaaagtg ctcatcattg gaaaacgttc ttcggggcga    6360
aaactctcaa ggatcttacc gctgttgaga tccagttcga tgtaacccac tcgtgcaccc    6420
aactgatctt cagcatcttt tactttcacc agcgtttctg ggtgagcaaa acaggaagg    6480 caaaatgccg caaaaaaggg aataagggcg acacggaaat gttgaatact catactcttc    6540
ctttttcaat attattgaag catttatcag ggttattgtc tcatgagcgg atacatattt    6600
gaatgtattt agaaaaataa acaaataggg gttccgcgca catttccccg aaaagtgcca    6660
cctgacgtct aagaaaccat tattatcatg acattaacct ataaaaatag gcgtatcacg    6720
aggccctttc gtctcgcgcg tttcggtgat gacggtgaaa acctctgaca catgcagctc    6780
ccggagacgg tcacagcttg tctgtaagcg gatgccggga gcagacaagc ccgtcagggc    6840
gcgtcagcgg gtgttggcgg gtgtcggggc tggcttaact atgcggcatc agagcagatt    6900
gtactgagag tgcaccatat gcggtgtgaa ataccgcaca gatgcgtaag gagaaaatac    6960
cgcatcagga aattgtaaac gttaatattt tgttaaaatt cgcgttaaat ttttgttaaa    7020
tcagctcatt ttttaaccaa taggccgaaa tcggcaaaat cccttataaa tcaaaagaat    7080
agaccgagat agggttgagt gttgttccag tttggaacaa gagtccacta ttaaagaacg    7140
tggactccaa cgtcaaaggg cgaaaaaccg tctatcaggg cgatggccca ctacgtgaac    7200
catcacccta atcaagtttt ttggggtcga ggtgccgtaa agcactaaat cggaacccta    7260
aagggagccc ccgatttaga gcttgacggg gaaagccggc gaacgtggcg agaaaggaag    7320
ggaagaaagc gaaaggagcg ggcgctaggg cgctggcaag tgtagcggtc acgctgcgcg    7380
taaccaccac acccgccgcg cttaatgcgc cgctacaggg cgcgtcgcgc cattcgccat    7440
tcaggctacg caactgttgg aagggcgat cggtgcgggc ctcttcgcta ttacgccagg    7500
ctgca                                                                7505
```

<210> SEQ ID NO 3
<211> LENGTH: 7671
<212> TYPE: DNA
<213> ORGANISM: Artificial Sequence
<220> FEATURE:
<223> OTHER INFORMATION: Synthetic construct (plasmid UF11-GPE-co-G6PC)
<220> FEATURE:

```
<221> NAME/KEY: misc_feature
<222> LOCATION: (17)..(163)
<223> OTHER INFORMATION: Inverted terminal repeat
<220> FEATURE:
<221> NAME/KEY: misc_feature
<222> LOCATION: (182)..(3045)
<223> OTHER INFORMATION: G6PC promoter/enhancer
<220> FEATURE:
<221> NAME/KEY: misc_feature
<222> LOCATION: (3051)..(3184)
<223> OTHER INFORMATION: Stuffer sequence
<220> FEATURE:
<221> NAME/KEY: misc_feature
<222> LOCATION: (3185)..(3321)
<223> OTHER INFORMATION: Intron
<220> FEATURE:
<221> NAME/KEY: misc_feature
<222> LOCATION: (3322)..(3367)
<223> OTHER INFORMATION: Stuffer sequence
<220> FEATURE:
<221> NAME/KEY: misc_feature
<222> LOCATION: (3368)..(4441)
<223> OTHER INFORMATION: Codon optimized G6PC coding sequence
<220> FEATURE:
<221> NAME/KEY: misc_feature
<222> LOCATION: (4674)..(4819)
<223> OTHER INFORMATION: Inverted terminal repeat

<400> SEQUENCE: 3
```

| | | | | | |
|---|---|---|---|---|---|
| gggggggggg | gggggggggtt | ggccactccc | tctctgcgcg | ctcgctcgct | cactgaggcc | 60 |
| gggcgaccaa | aggtcgcccg | acgcccgggc | tttgcccggg | cggcctcagt | gagcgagcga | 120 |
| gcgcgcagag | agggagtggc | caactccatc | actaggggtt | cctagatctg | aattcggtac | 180 |
| cccctttgaga | atccacggtg | tctcgatgca | gtcagctttc | taacaagctg | gggcctcacc | 240 |
| tgttttccca | cggataaaaa | cgtgctggag | gaagcagaaa | ggggctggca | ggtggaaaga | 300 |
| tgaggaccag | ctcatcgtct | catgactatg | aggttgctct | gatccagagg | gtcccctgc | 360 |
| ctggtggccc | accgccagga | agactcccac | tgtccctgga | tgcccagagt | gggatgtcaa | 420 |
| ctccatcact | tatcaactcc | ttatccctag | gggtattctt | cctgaggcgt | ctcagaaaac | 480 |
| agggccctcc | ccatatgctg | accacataat | agaacccctc | ccaactcaga | gaccctggct | 540 |
| gctagctgcc | ctggcatgac | ccagacagtg | gcctttgtat | atgttttag | actcaccttg | 600 |
| actcacctct | gaccatagaa | actctcatcc | cagaggtcac | tgcaatagtt | actccacaac | 660 |
| agaggcttat | ctgggtagag | ggaggctccc | tacctatggc | ccagcagccc | tgacagtgca | 720 |
| gatcacatat | accccacgcc | ccagcactgc | ctgccacgca | tgggcttact | ttacacccac | 780 |
| ccacagtcac | caacacatta | cctgctctcc | aaggttaggc | gtggcaggag | aagtttgctt | 840 |
| ggaccagcag | aaaccatgca | gtcaaggaca | actggagtca | gcatgggctg | ggtgcgagcc | 900 |
| cttggtgggg | tggggaggag | actccaggtc | atacctcctg | gaggatgttt | taatcatttc | 960 |
| cagcatggaa | tgctgtcaac | ttttgccaca | gattcattag | ctctgagttt | cttttttctg | 1020 |
| tccccagcta | ccccttacat | gtcaatatgg | acttaatgat | gggaaattca | ggcaagtttt | 1080 |
| taaacatttt | attcccctg | gctcttatcc | tcaaaaaatg | catgaatttg | gaggcagtgg | 1140 |
| ctcatgcctg | taatcccaat | gctttgctag | gttgaggcgg | gaggatcact | tgaagccagg | 1200 |
| aatttgagac | cagcctgggc | cgcatagtga | gaccccgttt | ctacaaaaat | aaataaataa | 1260 |
| ataataaata | atagtgatat | gaagcatgat | taaatagccc | tatttttaa | aatgcatgag | 1320 |
| ttcgttacct | gattcattcc | ctggttcctt | tcacagtcct | ccgtgaccca | agtgttaggg | 1380 |
| ttttggtctc | tctactattt | gtaggctgat | atatagtata | cacacacaca | cacacacaca | 1440 |
| tatacacaca | cacagtgtat | cttgagcttt | cttttgtata | tctacacaca | tatgtataag | 1500 |

-continued

```
aaagctcaag atatagaagc ccttttcaa aaataactga aagtttcaaa ctctttaagt    1560
ctccagttac cattttgctg gtattcttat ttggaaccat acattcatca tattgttgca    1620
cagtaagact atacattcat tattttgctt aaacgtatga gttaaaacac ttggccaggc    1680
atggtggttc acacctgtaa tcccagagct ttgggaagcc aagactggca gatctcttga    1740
gctcaggaat tcaagaccag cctgggcaac atggaaaaac cccatctcta caaagatag     1800 aaaaattagc caggcatggt ggcgtgtgcc tgtggtccca gctactcagg aggctgaggt    1860
gggaggatca cattagccca ggaggttgag gctgcagtga gccgtgatta tgccactgca    1920
ctccagcctg ggagacagag tgagaccctg tttcaaaaaa aagagagaga aaatttaaaa    1980
aagaaaacaa caccaagggc tgtaaccttta aggtcattaa atgaattaat cactgcattc    2040
aaaaacgatt actttctggc cctaagagac atgaggccaa taccaggaag ggggttgatc    2100
tcccaaacca gaggcagacc ctagactcta atacagttaa ggaaagacca gcaagatgat    2160
agtccccaat acaatagaag ttactatatt ttatttgttg ttttctttt gttttgtttt    2220 gttttgtttt gttttgtttt agagactggg gtcttgctcg attgcccagg ctgtagtgca    2280
gcggtgggac aatagctcac tgcagactcc aactcctggg ctcaagcaat cctcctgcct    2340
cagcctcctg aatagctggg actacaaggg tacaccatca cacaccaa acaattttt     2400 taaatttttg tgtagaaacg agggtcttgc tttgttgccc aggctggtct ccaactcctg    2460
gcttcaaggg atcctcccac ctcagcctcc caaattgctg ggattacagg tgtgagccac    2520
cacaaccagc cagaacttta ctaattttaa aattaagaac ttaaaacttg aatagctaga    2580
gcaccaagat ttttctttgt ccccaaataa gtgcagttgc aggcatagaa atctgacat     2640 ctttgcaaga atcatcgtgg atgtagactc tgtcctgtgt ctctggcctg gtttcgggga    2700
ccaggagggc agacccttgc actgccaaga agcatgccaa agttaatcat tggccctgct    2760
gagtacatgg ccgatcaggc tgttttttgtg tgcctgtttt tctatttac gtaaatcacc     2820 ctgaacatgt ttgcatcaac ctactggtga tgcacctttg atcaatacat tttagacaaa    2880
cgtggttttt gagtccaaag atcagggctg ggttgacctg aatactggat acagggcata    2940
taaaacaggg gcaaggcaca gactcatagc agagcaatca ccaccaagcc tggaataact    3000
gcaagggctc tgctgacatc ttcctgaggt gccaaggaaa tgaggtctag agaagcttta    3060
ttgcggtagt ttatcacagt taaattgcta acgcagtcag tgcttctgac acaacagtct    3120
cgaacttaag ctgcagtgac tctcttaagg tagccttgca gaagttggtc gtgaggcact    3180
gggcaggtaa gtatcaaggt tacaagacag gtttaaggag accaatagaa actgggcttg    3240
tcgagacaga gaagactctt gcgtttctga taggcaccta ttggtcttac tgacatccac    3300 tttgccttc tctccacagg tgtccactcc cagttcaatt acagctctta aggccctgca    3360
ggccaccatg gaagagggca tgaacgtgct gcacgacttc ggcatccaga gcacccacta    3420
tctgcaggtc aactaccagg acagccagga ctggttcatc ctggtgtccg tgatcgccga    3480
cctgcggaac gccttctacg tgctgttccc catctggttc catctgcaag aagccgtcgg    3540
catcaagctg ctgtgggtgg ccgtgatcgg cgattggctg aacctggtgt tcaagtggat    3600
cctgttcggc cagcggccct attggtgggt gctggacacc gactactaca gcaacaccag    3660
cgtgcccctg atcaagcagt tcccgtgac ctgcgagaca ggccctggct ctccttctgg    3720
ccacgccatg ggaacagccg gcgtgtacta cgtgatggtc accagcaccc tgagcatctt    3780
ccagggcaag atcaagccca cctaccggtt ccggtgcctg aacgtgatcc tgtggctggg    3840
```

```
cttctgggcc gtgcagctga acgtgtgcct gagccggatc tacctggccg cccacttccc   3900
acatcaagtg gtggccggcg tgctgagcgg aatcgccgtg gccgagacat tcagccacat   3960
ccacagcatc tacaacgcca gcctgaagaa gtacttcctg atcacattct ttctgttcag   4020
cttcgccatc ggcttctacc tgctgctgaa gggcctgggc gtggacctgc tgtggaccct   4080
ggaaaaggcc cagcggtggt gcgagcagcc cgagtgggtg cacatcgaca ccaccccctt   4140
cgccagcctg ctgaagaacc tgggcaccct gtttggactg ggcctggccc tgaacagcag   4200
catgtacaga gagagctgca agggcaagct gagcaagtgg ctgcccttcc ggctgagcag   4260
catcgtggcc agcctggtgc tgctgcacgt gttcgacagc ctgaagcccc ccagccaggt   4320
ggaactggtg ttttacgtgc tgagcttctg caagagcgcc gtggtgcccc tggcctccgt   4380
gtctgtgatc ccctactgcc tggctcaggt gctgggccag ccccacaaga agtccctctg   4440
agcggccgcg gggatccaga catgataaga tacattgatg agtttggaca aaccacaact   4500
agaatgcagt gaaaaaaatg ctttatttgt gaaatttgtg atgctattgc tttatttgta   4560
accattataa gctgcaataa acaagttaac aacaacaatt gcattcattt tatgtttcag   4620
gttcaggggg aggtgtggga ggttttttag tcgaccatgc tggggagaga tctaggaacc   4680
cctagtgatg gagttggcca ctccctctct gcgcgctcgc tcgctcactg aggccgcccg   4740
ggcaaagccc gggcgtcggg cgacctttgg tcgcccggcc tcagtgagcg agcgagcgcg   4800
cagagaggga gtggccaacc ccccccccc cccccctgca gccctgcatt aatgaatcgg   4860
ccaacgcgcg gggagaggcg gtttgcgtat tgggcgctct tccgcttcct cgctcactga   4920
ctcgctgcgc tcggtcgttc ggctgcggcg agcggtatca gctcactcaa aggcggtaat   4980
acggttatcc acagaatcag gggataacgc aggaaagaac atgtgagcaa aaggccagca   5040
aaaggccagg aaccgtaaaa aggccgcgtt gctggcgttt ttccataggc tccgcccccc   5100
tgacgagcat cacaaaaatc gacgctcaag tcagaggtgg cgaaacccga caggactata   5160
aagataccag gcgtttcccc ctggaagctc cctcgtgcgc tctcctgttc cgaccctgcc   5220
gcttaccgga tacctgtccg cctttctccc ttcgggaagc gtggcgcttt ctcaatgctc   5280
acgctgtagg tatctcagtt cggtgtaggt cgttcgctcc aagctgggct gtgtgcacga   5340
accccccgtt cagcccgacc gctgcgcctt atccggtaac tatcgtcttg agtccaaccc   5400
ggtaagacac gacttatcgc cactggcagc agccactggt aacaggatta gcagagcgag   5460
gtatgtaggc ggtgctacag agttcttgaa gtggtggcct aactacggct acactagaag   5520
gacagtattt ggtatctgcg ctctgctgaa gccagttacc ttcggaaaaa gagttggtag   5580
ctcttgatcc ggcaaacaaa ccaccgctgg tagcggtggt ttttttgttt gcaagcagca   5640
gattacgcgc agaaaaaaag gatctcaaga agatcctttg atcttttcta cggggtctga   5700
cgctcagtgg aacgaaaact cacgttaagg gattttggtc atgagattat caaaaaggat   5760
cttcacctag atccttttaa attaaaaatg aagttttaaa tcaatctaaa gtatatatga   5820
gtaaacttgg tctgacagtt accaatgctt aatcagtgag gcacctatct cagcgatctg   5880
tctatttcgt tcatccatag ttgcctgact ccccgtcgtg tagataacta cgatacggga   5940
gggcttacca tctggcccca gtgctgcaat gataccgcga gacccacgct caccggctcc   6000
agatttatca gcaataaacc agccagccgg aagggccgag cgcagaagtg gtcctgcaac   6060
tttatccgcc tccatccagt ctattaattg ttgccgggaa gctagagtaa gtagttcgcc   6120
agttaatagt ttgcgcaacg ttgttgccat tgctacaggc atcgtggtgt cacgctcgtc   6180
gtttggtatg gcttcattca gctccggttc ccaacgatca aggcgagtta catgatcccc   6240
```

-continued

```
catgttgtgc aaaaaagcgg ttagctcctt cggtcctccg atcgttgtca gaagtaagtt   6300
ggccgcagtg ttatcactca tggttatggc agcactgcat aattctctta ctgtcatgcc   6360
atccgtaaga tgcttttctg tgactggtga gtactcaacc aagtcattct gagaatagtg   6420
tatgcggcga ccgagttgct cttgcccggc gtcaatacgg gataataccg cgccacatag   6480
cagaacttta aaagtgctca tcattggaaa acgttcttcg gggcgaaaac tctcaaggat   6540
cttaccgctg ttgagatcca gttcgatgta acccactcgt gcacccaact gatcttcagc   6600
atcttttact ttcaccagcg tttctgggtg agcaaaaaca ggaaggcaaa atgccgcaaa   6660
aaagggaata agggcgacac ggaaatgttg aatactcata ctcttccttt ttcaatatta   6720
ttgaagcatt tatcagggtt attgtctcat gagcggatac atatttgaat gtatttagaa   6780
aaataaacaa ataggggttc cgcgcacatt tccccgaaaa gtgccacctg acgtctaaga   6840
aaccattatt atcatgacat taacctataa aaataggcgt atcacgaggc cctttcgtct   6900
cgcgcgtttc ggtgatgacg gtgaaaacct ctgacacatg cagctcccgg agacggtcac   6960
agcttgtctg taagcggatg ccgggagcag acaagcccgt cagggcgcgt cagcgggtgt   7020
tggcgggtgt cggggctggc ttaactatgc ggcatcagag cagattgtac tgagagtgca   7080
ccatatgcgg tgtgaaatac cgcacagatg cgtaaggaga aaataccgca tcaggaaatt   7140
gtaaacgtta atattttgtt aaaattcgcg ttaaattttt gttaaatcag ctcatttttt   7200
aaccaatagg ccgaaatcgg caaaatccct tataaatcaa aagaatagac cgagataggg   7260
ttgagtgttg ttccagtttg gaacaagagt ccactattaa agaacgtgga ctccaacgtc   7320
aaagggcgaa aaaccgtcta tcagggcgat ggcccactac gtgaaccatc accctaatca   7380
agttttttgg ggtcgaggtg ccgtaaagca ctaaatcgga accctaaagg gagcccccga   7440
tttagagctt gacggggaaa gccggcgaac gtggcgagaa aggaagggaa gaaagcgaaa   7500
ggagcgggcg ctagggcgct ggcaagtgta gcggtcacgc tgcgcgtaac caccacaccc   7560
gccgcgctta atgcgccgct acagggcgcg tcgcgccatt cgccattcag gctacgcaac   7620
tgttgggaag ggcgatcggt gcgggcctct tcgctattac gccaggctgc a            7671

<210> SEQ ID NO 4
<211> LENGTH: 357
<212> TYPE: PRT
<213> ORGANISM: Homo sapiens

<400> SEQUENCE: 4

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr

```

```
            115                 120                 125
Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
        355

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
cctttgagaa tccacggtgt                                           20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
cctcatttcc ttggcacctc                                           20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide
```

-continued

```
<400> SEQUENCE: 7
aggtaagtat caaggttaca                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
acctgtggag agaaaggcaa                                                    20

<210> SEQ ID NO 9
<211> LENGTH: 1074
<212> TYPE: DNA
<213> ORGANISM: Canis familiaris familiaris

<400> SEQUENCE: 9
atggagaaag gaatggatgt gctccatgac tttggaatcc agtcaacgca ctacctccag        60
gtgaattacc aggactctca ggattggttc atcttggtgt ccgtgattgc agacctcagg       120
aatgccttct atgtcctctt tcccatctgg ttccatctgc gtgaagctgt gggcatcaaa       180
cttctctggg tagctgtgat tggagactgg ctcaacctcg tctttaaatg gattctgttt       240
ggacagcgtc catactggtg ggtcatggac accgactact atagcaacac ctctgtgcca       300
ctgataaagc aatttccagt tacctgtgaa actggaccag ggagtccctc tggtcatgcc       360
atgggtacag caggtgtata ctacgtgatg gtcacatcta ccctttctat ctttcggggg       420 agaaaaggc aacctacag atttcggtgc ttgaatatcc ttctgtggtt gggattctgg         480
gctgtgcagc tgaacgtctg tctgtcccga atctaccttg ctgctcattt cccccatcag       540
gttgttgctg gagtcctgtc aggcattgct gttgctgaaa cttccgccca catccagagc       600
atctacaatg ccagcctcaa gaaatatttt ctcattactt tcttcctgtt cagttttgcc       660
attggatttt acctgctgct caaggggctg gtgtggacc tcctgtggac actggaaaaa       720
gccaggagat ggtgtgagcg gccggaatgg gttcacattg acaccacacc ctttgccagc       780
cttctcaaga acgtggggac cctctttggc ctggggtga ctctcaactc cagcatgtac        840
agggaaagct gcaagggcaa gcttagcaag tggttcccat tccgcctcag ctgcattgtg       900
gtgtctctca tcctcctgca cctctttgac tctttgaaac ccccatccca aactgagctg       960
atcttctaca cctttgtcctt ctgcaagagt gcagcagtgc ccctggcatc tgtcagcctc      1020
atcccctact gccttgcccg ggtcttcgac cagccagaca agaagtcttt gtaa            1074

<210> SEQ ID NO 10
<211> LENGTH: 357
<212> TYPE: PRT
<213> ORGANISM: Canis lupus familiaris

<400> SEQUENCE: 10

Met Glu Lys Gly Met Asp Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Arg Glu Ala Val Gly Ile Lys Leu Leu Trp Val
    50                  55                  60
```

```
Ala Val Ile Gly Asp Trp Leu Asn Leu Val Phe Lys Trp Ile Leu Phe
65                  70              75              80

Gly Gln Arg Pro Tyr Trp Trp Val Met Asp Thr Asp Tyr Tyr Ser Asn
                85              90              95

Thr Ser Val Pro Leu Ile Lys Gln Phe Pro Val Thr Cys Glu Thr Gly
                100             105             110

Pro Gly Ser Pro Ser Gly His Ala Met Gly Thr Ala Gly Val Tyr Tyr
                115             120             125

Val Met Val Thr Ser Thr Leu Ser Ile Phe Arg Gly Arg Lys Arg Pro
130             135             140

Thr Tyr Arg Phe Arg Cys Leu Asn Ile Leu Leu Trp Leu Gly Phe Trp
145             150             155             160

Ala Val Gln Leu Asn Val Cys Leu Ser Arg Ile Tyr Leu Ala Ala His
                165             170             175

Phe Pro His Gln Val Val Ala Gly Val Leu Ser Gly Ile Ala Val Ala
                180             185             190

Glu Thr Phe Arg His Ile Gln Ser Ile Tyr Asn Ala Ser Leu Lys Lys
                195             200             205

Tyr Phe Leu Ile Thr Phe Phe Leu Phe Ser Phe Ala Ile Gly Phe Tyr
210             215             220

Leu Leu Leu Lys Gly Leu Gly Val Asp Leu Leu Trp Thr Leu Glu Lys
225             230             235             240

Ala Arg Arg Trp Cys Glu Arg Pro Glu Trp Val His Ile Asp Thr Thr
                245             250             255

Pro Phe Ala Ser Leu Leu Lys Asn Val Gly Thr Leu Phe Gly Leu Gly
                260             265             270

Val Thr Leu Asn Ser Ser Met Tyr Arg Glu Ser Cys Lys Gly Lys Leu
                275             280             285

Ser Lys Trp Phe Pro Phe Arg Leu Ser Cys Ile Val Val Ser Leu Ile
290             295             300

Leu Leu His Leu Phe Asp Ser Leu Lys Pro Pro Ser Gln Thr Glu Leu
305             310             315             320

Ile Phe Tyr Thr Leu Ser Phe Cys Lys Ser Ala Ala Val Pro Leu Ala
                325             330             335

Ser Val Ser Leu Ile Pro Tyr Cys Leu Ala Arg Val Phe Asp Gln Pro
                340             345             350

Asp Lys Lys Ser Leu
            355
```